(12) United States Patent
Ryals et al.

(10) Patent No.: US 7,781,160 B2
(45) Date of Patent: Aug. 24, 2010

(54) BIOMARKERS RELATED TO METABOLIC AGE AND METHODS USING THE SAME

(75) Inventors: John Ryals, Chapel Hill, NC (US); Mike Milburn, Cary, NC (US); Matthew W. Mitchell, Durham, NC (US); Kay A. Lawton, Raleigh, NC (US)

(73) Assignee: Metabolon, Inc., Durham, NC (US)

( * ) Notice: Subject to any disclaimer, the term of this patent is extended or adjusted under 35 U.S.C. 154(b) by 0 days.

(21) Appl. No.: 11/871,752

(22) Filed: Oct. 12, 2007

(65) Prior Publication Data

US 2008/0124752 A1    May 29, 2008

Related U.S. Application Data

(60) Provisional application No. 60/851,468, filed on Oct. 13, 2006.

(51) Int. Cl.
 *C12Q 1/00* (2006.01)
(52) U.S. Cl. .................. 435/4; 435/6; 435/29
(58) Field of Classification Search ............ 435/4
 See application file for complete search history.

(56) References Cited

U.S. PATENT DOCUMENTS

| 6,569,624 | B1 | 5/2003 | Weindruch et al. | |
| 2003/0082597 | A1* | 5/2003 | Cannon et al. | 435/6 |

| 2006/0068432 | A1 | 3/2006 | Barzilai |

FOREIGN PATENT DOCUMENTS

| CA | 2 527 957 | 1/2005 |

OTHER PUBLICATIONS

International Search Report for International Application No. PCT/US2007/81268; International Filing Date: Oct. 12, 2007; Date of Completion: Sep. 2, 2008; Date of Mailing: Oct. 1, 2008.
Duggirala, R. et al., "Genetic determination of biological age in the mennonites of the midwestern united states", Genetic Epidemiology, 23, 97-109 (2002).
International Preliminary Report on Patentability for International Application No. PCT/US2007/81268; International Filing Date: Oct. 12, 2007; Date of Submission: Jan. 2, 2009; Date of Completion: Feb. 11, 2009.
Supplementay Partial European Search Report for EP Application No. 07 86 8439.
Sell, David R. et al., "Ornithine Is a Novel Amino Acid and a Marker of Arginine Damage by Oxoaldehydes in Senescent Proteins" Annals of the New York Academy of Sciences, 2005, pp. 118-128 XP002566426.

* cited by examiner

*Primary Examiner*—Jon P Weber
*Assistant Examiner*—Tiffany M Gough
(74) *Attorney, Agent, or Firm*—Brinks Hofer Gilson & Lione

(57) ABSTRACT

Biomarkers relating to metabolic age are provided, as well as methods for using such biomarkers as biomarkers for determining metabolic age. In addition, methods for modulating the metabolic age of a subject are also provided. Also provided are suites of small molecule entities as biomarkers for metabolic age.

8 Claims, 13 Drawing Sheets

Figure 3 Age prediction by step-wise regression analysis.
3A. Females
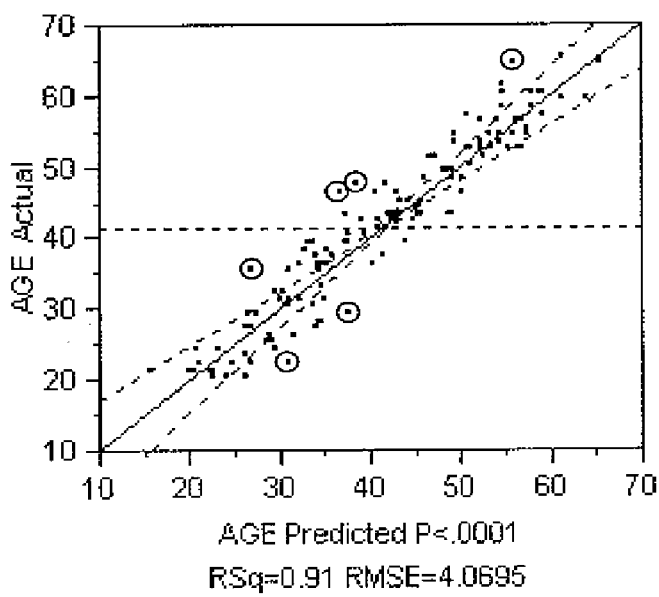
3B. Males
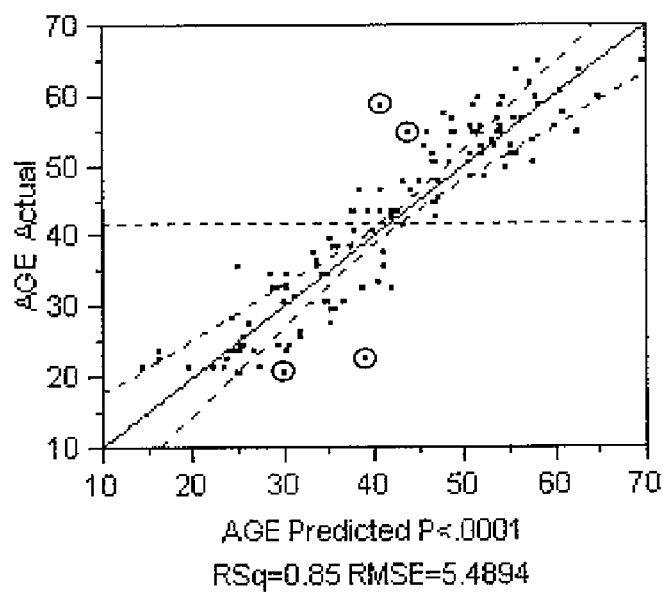

BIOMARKERS RELATED TO METABOLIC AGE AND METHODS USING THE SAME

CROSS-REFERENCE TO RELATED APPLICATIONS

This application claims the benefit of U.S. Provisional Application No. 60/851,468, filed Oct. 13, 2006, the entirety of which is hereby incorporated by reference.

FIELD OF THE INVENTION

This invention relates to biomarkers and methods to determine metabolic age of a subject and methods of using such biomarkers. The invention also relates to biomarkers and methods of using biomarkers relating to gender and race.

BACKGROUND

Interest in metabolomics is growing at a considerable rate. Since 2000, there has been a steady increase in the number of PubMed™ citations per publication year that contain the term "metabolomics" in either the title or abstract fields. Although metabolomics is still an emerging technology, it has already been applied to a diverse set of problems in disparate areas such as pharmaceutical discovery and development, natural products research, and disease diagnosis, just to name a few. (Griffin, J. L., 2006, Philos Trans R Soc Lond B Biol Sci, 361(1465):147-61; Keun, H. C., 2006, Pharmacol Ther, 109 (1-2):92-106; Rochfort, S., J. Nat Prod, 2005. 68(12):1813-2; Kristal, B. S. and Y. I. Shurubor, Sci Aging Knowledge Environ, 2005. 2005(26):pe19; Morris, M. and S. M. Watkins, 2005, Curr Opin Chem Biol 9(4):407-12; Witkamp, R. F., 2005, J Vet Pharmacol Ther, 28(3):235-45; Watkins, S. M. and J. B. German, 2002, Curr Opin Mol Ther, 4(3):224-8; Fiehn, O., 2002, Plant Mol Biol, 48(1-2):155-71).

The metabolism of an individual changes with age. Until recently the ability to monitor metabolite changes has been limited to targeted assays. With the development of metabolomics analysis, changes in metabolites can now be monitored globally in a non-targeted manner. This metabolomic approach allows a metabolic profile to be determined for a group or an individual.

As more information regarding the impact of nutrition on health-related issues becomes available and as the population ages, interest in health and nutrition has increased. The ability to determine the metabolite levels of an individual and classify the resulting metabolic profile as positive or negative and then to provide guidance as to how to improve a negative profile will have beneficial effects on the health of an individual.

SUMMARY

Methods for determining the metabolic age of a subject are provided. In one aspect, the methods comprise the steps of: (a) analyzing a biological sample from a subject to determine the level(s) of one or more biomarkers for metabolic age in the sample, wherein the one or more biomarkers are selected from Tables 2, 7, and/or 8 and combinations thereof; and (b) comparing the level(s) of the one or more biomarkers in the sample to metabolic age reference levels of the one or more biomarkers to determine the subject's metabolic age.

In another aspect, methods for producing a Biochemical Age Index (BAI) are provided. Such methods comprise the steps of: (a) analyzing biological samples from a plurality of subjects to determine the level(s) of one or more first biomarkers that change with age; (b) identifying one or more second biomarkers that correlate with each of the one or more first biomarkers that change with age to generate one or more groups of biomarkers that change with age; and (c) generating a biochemical age index using the levels of each of the one or more groups of biomarkers.

Also provided are methods for modifying the metabolic age of a subject comprising the steps of: (a) analyzing a biological sample from a subject to determine the level(s) of one or more biomarkers for metabolic age in the sample, wherein the one or more biomarkers are selected from Tables 2, 7, and/or 8 and combinations thereof; (b) comparing the level(s) of the one or more biomarkers in the sample to metabolic age reference levels of the one or more biomarkers to determine the subject's metabolic age; and (c) providing recommendations to modify the metabolic age of a subject through changes in diet, nutrition, lifestyle, and/or administration of metabolites.

In another aspect, methods of assessing the efficacy of a composition for modulating metabolic age, comprising: (a) analyzing a first biological sample from a subject having a first metabolic age and currently or previously being treated with a compound or composition to determine the level(s) of one or more biomarkers selected from Tables 2, 7, and/or 8, and (b) comparing the level(s) of the one or more biomarkers in the sample to biomarkers levels selected from the group consisting of (i) level(s) of the one or more biomarkers in a second biological sample from the subject obtained from the subject before being treated with the compound or composition, (ii) metabolic age-positive reference levels of the one or more biomarkers, (iii) metabolic age-negative reference levels of the one or more biomarkers, and (iv) reference levels of the one or more biomarkers for a target metabolic age.

In addition, methods for screening a test compound for activity in modulating the level of one or more biomarkers of metabolic age are provided. Such methods comprise: (a) contacting one or more cells with a test compound; (b) analyzing at least a portion of the one or more cells or a biological sample associated with the cells to determine the level(s) of one or more biomarkers of metabolic age selected from Tables 2, 7, and/or 8; and (c) comparing the level(s) of the one or more biomarkers with predetermined levels for the biomarkers to determine whether the composition modulated the level(s) of the one or more biomarkers.

DESCRIPTION OF FIGURES

FIG. 3 is a stepwise regression plot illustrating the use of age biomarkers to predict the chronological age of a female individual (FIG. 3A) or a male individual (FIG. 3B) based upon the levels of a set of age biomarkers in the sample.

FIG. 5A is alanine; FIG. 5B is glutamine, FIG. 5C is normetanephrine; FIG. 5D is ornithine; FIG. 5E is valine; and FIG. 5F is the Index which is derived from combining the individual compounds versus age. The increase in the level of each of the compounds in this example becomes more pronounced at around age 45, and the variability appears to increase with age.

DETAILED DESCRIPTION

Figure 1:
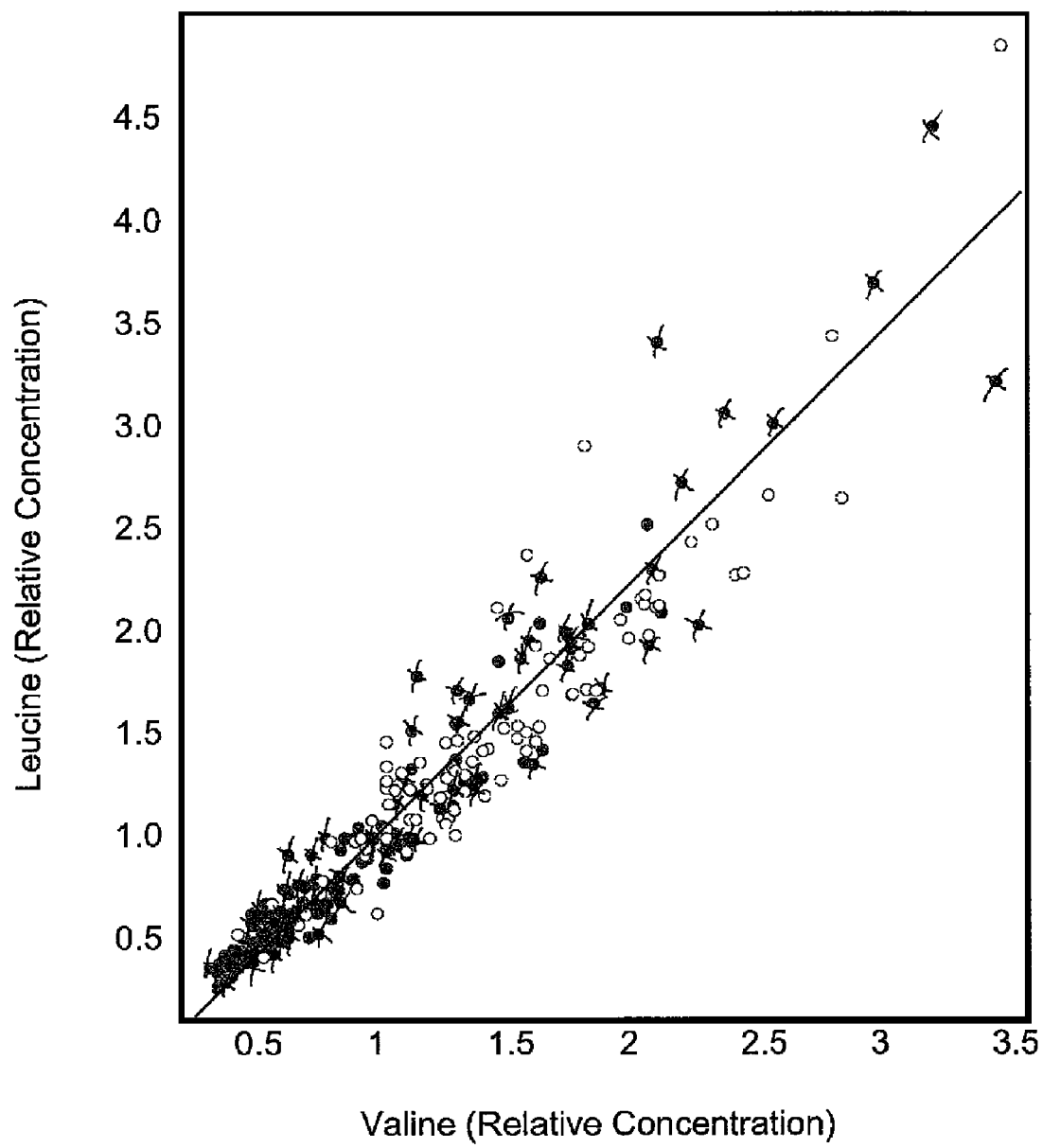
FIG. 1 is a graph showing the correlation between the relative concentrations of leucine vs. valine as a function of age in humans in three difference age groups. Dark circle, ages 21-35; circle with X, ages 36-50; light circle, ages 51-65.

The present invention relates to biomarkers of metabolic age, gender and race; methods for determination of metabolic age, methods of monitoring progression/regression of metabolic aging, methods of assessing efficacy of compositions for increasing or decreasing metabolic age of an individual, methods of screening compositions for activity in modulating biomarkers of age, gender or race, methods of modulating metabolic age, as well as other methods based on biomarkers of age, gender or race.

Prior to describing this invention in further detail, however, the following terms will first be defined. Definitions:

"Biochemical Age Index" (BAT) means the average levels of a group of compounds that change with age and are correlated with one another that can be combined to provide a biochemical age index, BAI. The BAI provides a measure of metabolic age for a population and/or group and/or a plurality of samples that is more robust (i.e. less variable, explains more of the individual variation) than can be obtained with individual compounds alone.

"Biomarker" means a compound, preferably a metabolite, that is differentially present (i.e., increased or decreased) in a biological sample from a subject or a group of subjects having a first phenotype (e.g., having a particular metabolic age, being within a particular metabolic age range, or having a disease) as compared to a biological sample from a subject or group of subjects having a second phenotype (e.g., having a different metabolic age, being within a different metabolic age range, or not having the disease). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (i.e., a p-value less than 0.05 and/or a q-value of less than 0.10 as determined using either Welch's T-test or Wilcoxon's rank-sum Test).

The "level" of one or more biomarkers means the absolute or relative amount or concentration of the biomarker in the sample.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, blood, blood plasma, urine, cerebral spinal fluid (CSF), crevicular fluid, saliva or breath condensate.

"Subject" means any animal, but is preferably a mammal, such as, for example, a human, monkey, non-human primate, rat, mouse, dog, cat, horse or rabbit.

A "reference level" of a biomarker means a level of the biomarker that is indicative of a particular age, particular age range, disease state, phenotype, or lack thereof, as well as combinations of disease states, phenotypes, or lack thereof. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular metabolic age, age ranges, disease or illness state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Reference levels may also be tailored to specific populations of subjects, including gender populations, race populations, or combinations thereof (e.g. black males, black females, white males, white females, Hispanic males, or Hispanic females). Such reference levels may also be tailored to specific techniques that are used to measure levels of biomarkers in biological samples (e.g., LC-MS, GC-MS, etc.), where the levels of biomarkers may differ based on the specific technique that is used.

"Metabolite", or "small molecule", means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell.

"Metabolic profile", or "small molecule profile", or "metabolite profile", means a complete or partial inventory of small molecules within a targeted cell, tissue, organ, organism, or fraction thereof (e.g., cellular compartment). The inventory may include the quantity and/or type of small molecules present. The "small molecule profile" may be determined using a single technique or multiple different techniques. The inventory may include any number of small molecules, for example, 1, 2, 3, 4, 5, 6, 7, 8, 9, 10, 15, 20, or more small molecules within a targeted cell, tissue, organ, organism, or fraction thereof.

"Non-biomarker compound" means a compound that is not differentially present in a biological sample from a subject or a group of subjects having a first phenotype (e.g., having a particular age, or within a particular age range, or gender or race) as compared to a biological sample from a subject or group of subjects having a second phenotype (e.g., having a different age, or within a different age range, or gender or race). Such non-biomarker compounds may, however, be biomarkers in a biological sample from a subject or a group of subjects having a third phenotype (e.g., having yet a different age or being within a different age range, or race) as compared to the first phenotype (e.g., having the first age, age range, gender or race) or the second phenotype (e.g., having a different age, age range, gender or race). Further, these compounds may be useful in determining a BAI.

"Metabolome" means all of the small molecules present in a given organism. The metabolome includes both metabolites and products of catabolism.

Figure 2:
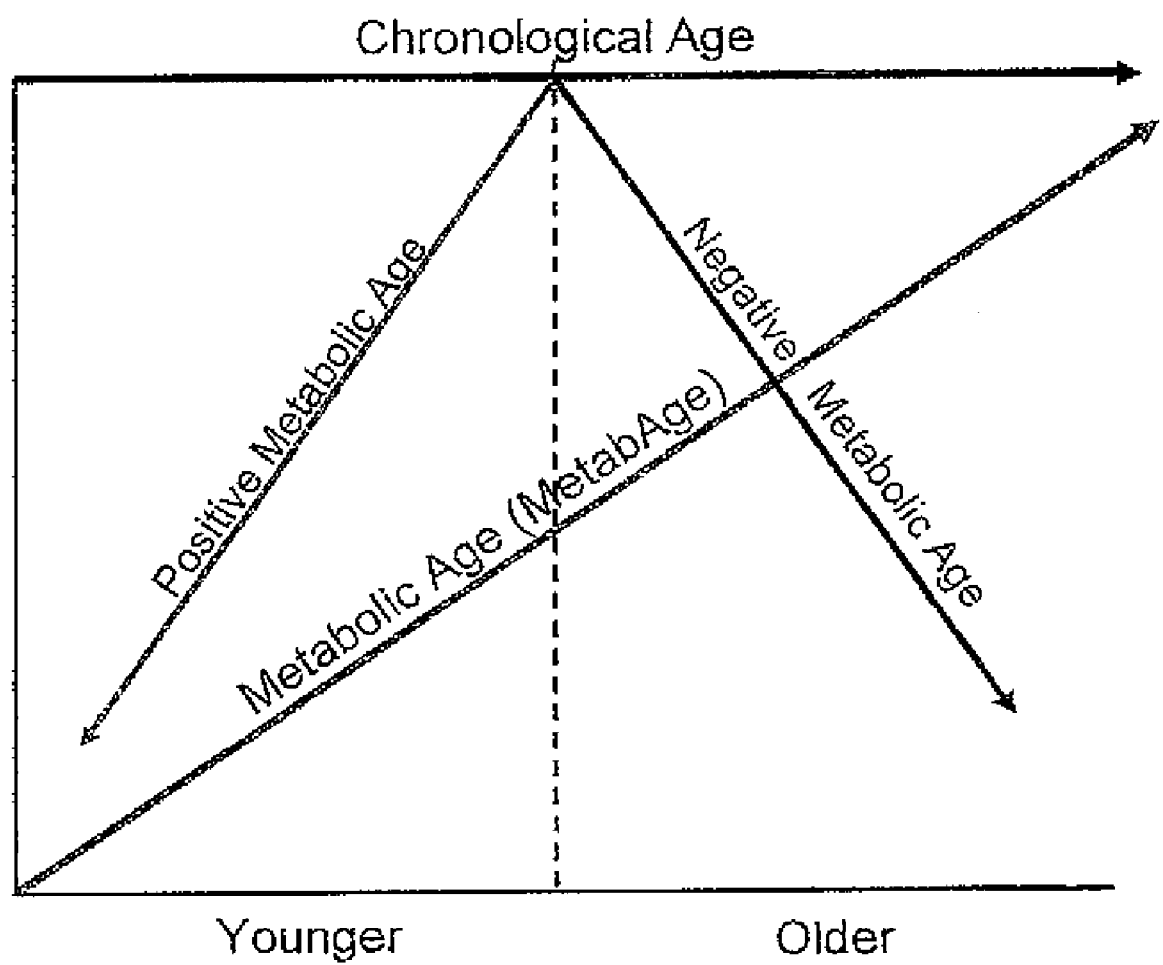
FIG. 2 is a chart illustrating the concept of a metabolic age and the association between metabolic age and chronological age. Changes in metabolic age (MetaboAge) are associated with aging or influence of dietary or lifestyle changes.

"Metabolic age" ("MetaboAge" or "MetabAge") means the age of a subject as determined by the composition of metabolites in cells, tissue and/or fluids. The metabolic age of a subject is determined by comparing the metabolic profile of the subject with metabolic profiles characteristic of various age groups (e.g. <25, 25-35, 36-50, 51-65, >65) (see FIG. 2). The metabolic age may also be determined by comparison of a subject's metabolic profile to a biochemical age index. If the subject profile resembles the profile characteristic of individuals of an age or age group younger than the subject's chronological age, the subject's metabolic age is "positive" while if the profile resembles the profile characteristic of an age group older than the subject's chronological, the subject's metabolic age is "negative".

"MetaboScore" means the calculated value using the Biochemical Age Index (BAI) that represents the difference between the metabolic age (MetaboAge) and the chronological age of a subject. A negative MetaboScore indicates the subject is younger biochemically than chronologically, while a positive MetaboScore indicates the subject is biochemically older than the chronological age.

"Xenobiotic" means "a chemical which is found in an organism but which is not normally produced or expected to be present in it. A xenobiotic is a compound that is foreign to a living organism. Principle xenobiotics include drugs, carcinogens, and various compounds that have been introduced into the environment by artificial means." IUPAC Compendium on Chemical Terminology 2003. (available on the worldwide web at iupac.org). Metabolites that are produced by the organism from the xenobiotic may also be considered to be xenobiotics.

"Xenobiotic Score" means the calculated value that represents the difference between the level(s) of one or more xenobiotics and the reference level(s) of one or more xenobiotics as determined by a Xenobiotic Age Index (XAI). A negative Xenobiotic Score indicates the subject has lower levels of a xenobiotic than the reference level for their chronological age, while a positive Xenobiotic Score indicates the subject has a higher level of a xenobiotic than the reference level for their chronological age.

Metabolomic studies allow identification of metabolic profiles associated with aging. Metabolomic analysis of a large cohort of individuals has demonstrated that one or more biomarkers may be present in an organism, cell, tissue, or portion thereof at different levels that correlate with the age of the organism, cell, tissue, or portion thereof. The levels change over time according to the age of the organism, cell, tissue, or portion thereof. Metabolic profiles may be determined that are associated with specific ages or age groups. The metabolic profile for an individual subject can be obtained using metabolomics and by comparison with the characteristic age-related metabolic profiles the metabolic age of the individual can be determined. Based upon the metabolic profile nutritional and/or lifestyle recommendations can be made to improve the metabolic profile of the individual. In addition to determining the MetaboAge and/or MetaboScore of the individual, the metabolic profile may be evaluated further to identify changes in specific metabolites and the associated biochemical pathways. The disclosed methods may be targeted to selected populations of subjects depending on biomarker differences within the selected population, for example, between race populations, gender populations or combinations of race and gender populations.

Metabolic or biochemical changes correlated with aging may be identified by the biomarkers and methods disclosed herein and may be used to distinguish groups of individuals according to age. Thus, the metabolic age or status of a subject can be determined by comparing the metabolic profile of a subject with the metabolic profile of specific age or age groups. Such profiles may be based on gender or race specific profiles. With this information recommendations can be made (e.g. by a physician, a physician's assistant, a nutritionist, etc.) to the subject that will enable the subject to alter his/her metabolic age through therapeutic agents, nutritional supplements and/or diet. The present invention also describes methods to develop a Biochemical Age Index for determining the metabolic age of a subject and to calculate a MetaboScore value that is the difference between the subject's chronological age and metabolic age.

When such a method is used to aid in determining the subject's metabolic age, the results of the method may be used along with other methods (or the results thereof) useful in the clinical determination, for example, for: 1) determining fitness for surgery, chemotherapy, physical therapy, or other medical treatments; 2) determining dosage for anesthesia; 3)

determining requirement for additional diagnostic assays; and/or 4) determining potential drug treatments, regimens and/or dosages. The metabolic age analysis is also useful for determining risk factors for illness and/or disease.

The present disclosure provides an understanding of the number and identity of small molecule compounds that are present in biological fluids (e.g. human plasma), along with the distribution of their relative concentrations.

Additionally, the present invention provides an understanding of the influence of age, gender, and race on the relative levels of observed compounds. Besides understanding the effects of these factors on the small-molecule complement of human plasma, and/or other biological samples (e.g. tissue, saliva, urine, plasma, etc.) such knowledge would also permit us to compare and contrast an efficient, metabolomics-based measurement process with more traditional clinical measurement determinations.

I. Biomarkers

Metabolic age biomarkers described herein were discovered using metabolic profiling techniques. Such metabolomic profiling techniques are described in more detail in the Examples set forth below as well as in U.S. Pat. No. 7,005,255 and U.S. patent application Ser. Nos. 11/357,732, 10/695,265 (Publication No. 2005/0014132), 11/301,077 (Publication No. 2006/0134676), 11/301,078 (Publication No. 2006/0134677), 11/301,079 (Publication No. 2006/0134678), and 11/405,033, the entire contents of which are hereby incorporated herein by reference.

Generally, metabolic profiles were determined for biological samples from human subjects from various age groups (e.g. <25, 25-35, 36-50, 51-65, >65). The metabolic age of an individual is determined by comparing the metabolic profile with metabolic profiles characteristic of various age groups (e.g. <25, 25-35, 36-50, 51-65, >65) (see FIG. 2). If the individual profile resembles the profile characteristic of individuals in an age group younger than the individual's chronological age, the individual's metabolic age is "positive" while if the profile resembles the profile characteristic of an age group older than the individual's chronological, the individual's metabolic age is "negative". MetaboAge is inversely correlated with the MetaboScore, i.e., a younger MetaboAge will result from a negative MetaboScore and an older MetaboAge will result from a positive MetaboScore.

Those molecules differentially present, including those molecules differentially present at a level that is statistically significant, in the metabolic profile of samples from subjects from various age, race, and/or gender groups as compared to another group (e.g., subjects from a different age, race, and/or gender group) were identified as biomarkers to distinguish those groups.

Biomarkers for use in methods relating to distinguishing metabolic age include those listed in Tables 2, 4, 5, 7, and/or 8, and combinations thereof. Biomarkers for use in methods relating to distinguishing gender include those listed in Table 4; biomarkers for use in methods relating to distinguishing race include those listed in Table 5; biomarkers that increase with age include those listed in Tables 2, 7, and/or 8 and combinations thereof; and biomarkers that decrease with age include those listed in Table 2, 7, and/or 8, and combinations thereof; and biomarkers that change with age include those listed in Tables 2, 7, and/or 8, and combinations thereof.

Non-biomarker compounds associated with the compared groups may also be identified.

Although the identities of some of the biomarkers and non-biomarker compounds are not known at this time, such identities are not necessary for the identification of the biomarkers or non-biomarker compounds in biological samples from subjects, as the "unnamed" compounds have been sufficiently characterized by analytical techniques to allow such identification. The analytical characterization of all such "unnamed" compounds is listed in the Examples. Such "unnamed" biomarkers and non-biomarker compounds are designated herein using the nomenclature "Metabolite" followed by a specific metabolite number.

Xenobiotics, such as, for example, tartaric acid and benzoic acid may also be measured. Xenobiotic compounds from individuals are measured and used to determine a correlation between xenobiotic compounds and age. Measurement of such xenobiotic compounds is used to calculate a xenobiotic score to determine dietary differences between individuals and a reference level according to age. Xenobiotic levels can also be used to make recommendations to changes in diet, lifestyle or medication.

II. Analyzing Metabolic Age

Methods for determining a subject's metabolic age may be performed using one or more of the biomarkers identified in the respective Tables provided herein. For example, a method for determining the metabolic age of a subject comprises the steps of: (1) analyzing a biological sample from a subject to determine the level(s) of one or more metabolic age biomarkers in the sample, and (2) comparing the level(s) of the one or more metabolic age biomarkers in the sample to metabolic age reference levels of the one or more biomarkers in order to determine the subject's metabolic age. The level(s) of the one or more biomarkers may be compared to a biochemical age index (BAI) to determine the subject's metabolic age. The one or more biomarkers that are used are selected from Tables 2, 4, 5, 7, and/or 8 and combinations thereof.

Any suitable method may be used to analyze the biological sample in order to determine the level(s) of the one or more biomarkers in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured.

The levels of one or more of the biomarkers of Tables 2, 4, 5, 7, and/or 8, may be determined in the methods for determining the metabolic age of a subject and methods of aiding in analyzing a metabolic profile. For example, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, fifteen or more biomarkers, etc., including a combination of all of the biomarkers in Tables 2, 4, 5, 7, and/or 8 or any fraction thereof, may be determined and used in such methods. Determining levels of combinations of the biomarkers allow greater sensitivity and specificity in analyzing a metabolic profile and aiding in the determining metabolic age, and may allow better differentiation of a metabolic age from other metabolic variations or disorders that may have similar or overlapping biomarkers to metabolic age.

Furthermore, ratios of the levels of certain biomarkers (M1/M2) (and non-biomarker compounds) in biological samples may allow greater sensitivity and specificity in determining metabolic age or diagnosis of metabolic disorder, and may allow better differentiation of metabolic age from other metabolic variations or disorders that may have similar or overlapping biomarkers. Also, ratios of xenobiotics (X1/X2) in biological samples are also used to measure differences in metabolic profiles of subjects. These ratios may allow better specificity and differentiation in measuring metabolic differences. Further, ratios of certain biomarkers and xenobiotics (M1/X1) also can be used to provide greater sensitivity and specificity in analyzing metabolic profiles of subjects.

After the level(s) of the one or more biomarkers in the sample are determined, the level(s) are compared to metabolic age reference levels to aid in analyzing the metabolic profile of an individual to determine the subject's metabolic age. Levels of the one or more biomarkers in a sample matching particular metabolic age reference levels (e.g., levels that are the same as the reference levels, substantially the same as the reference levels, above and/or below the minimum and/or maximum of the reference levels, and/or within the range of the reference levels) are indicative of the metabolic age of the subject. Levels of the one or more biomarkers in a sample not matching the metabolic age reference levels (e.g., levels that are the same as the reference levels, substantially the same as the reference levels, above and/or below the minimum and/or maximum of the reference levels, and/or within the range of the reference levels) are indicative of that an individual does not fit within a particular metabolic age. In some instances, the reference levels used for such comparisons may be based on gender and/or race differences in biomarker reference levels within a selected population (for example reference levels of biomarkers for black male or hispanic female populations). Such biomarkers that may be used to distinguish gender and/or race differences include those identified Tables 4 and/or 5 and combinations thereof.

The level(s) of the one or more biomarkers may be compared to the metabolic age reference levels using various techniques, including a simple comparison (e.g., a manual comparison) of the level(s) of the one or more biomarkers in the biological sample to the level in a different metabolic age reference level. The level(s) of the one or more biomarkers in the biological sample may also be compared to the metabolic age reference levels using one or more statistical analyses (e.g., t-test, Welch's T-test, Wilcoxon's rank sum test, random forest).

In addition, the biological samples may be analyzed to determine the level(s) of one or more non-biomarker compounds. The level(s) of such non-biomarker compounds may also allow differentiation of metabolic age or a metabolic disorder from other metabolic ages or metabolic variations or disorders that may have similar or overlapping biomarkers to a particular metabolic age. For example, a known non-biomarker compound present in biological samples of subjects of a particular metabolic age and subjects of a different metabolic age could be monitored to verify the estimate of a particular metabolic age as compared to another metabolic age when biological samples from subjects having the other metabolic ages do not have the non-biomarker compound.

III. Methods for Monitoring the Increasing or Decreasing of Metabolic Age

The identification of biomarkers for metabolic age also allows for monitoring the increasing or decreasing of metabolic age in a subject. A method of monitoring the increasing or decreasing of metabolic age of a subject comprises the steps of: (1) analyzing a first biological sample from a subject to determine the level(s) of one or more biomarkers for metabolic age selected from Tables 2, 7, and/or 8, the first sample obtained from the subject at a first time point, (2) analyzing a second biological sample from a subject to determine the level(s) of the one or more biomarkers, the second sample obtained from the subject at a second time point, and (3) comparing the level(s) of one or more biomarkers in the first sample to the level(s) of the one or more biomarkers in the second sample in order to monitor the increase or decrease of metabolic age of the subject. The level(s) of the one or more biomarkers may also be compared to a biochemical age index (BAI) to monitor the increase or decrease of metabolic age of the subject. The results of the method are indicative of the metabolic age difference or MetaboScore (i.e., increase or decrease, if any change) in the subject. The change (if any) in the level(s) of the one or more biomarkers over time may be indicative of increase or decrease in the metabolic age in the subject.

In order to characterize the course of metabolic age in the subject, the level(s) of the one or more biomarkers in the first sample, the level(s) of the one or more biomarkers in the second sample, and/or the results of the comparison of the levels of the biomarkers in the first and second samples may be compared to metabolic age reference levels of the one or more biomarkers. If the comparisons indicate that the level(s) of the one or more biomarkers are increasing or decreasing over time (e.g., in the second sample as compared to the first sample) to become more similar to an older metabolic age reference level (or less similar to a relatively younger metabolic age reference level), then the results are indicative of an increase in metabolic age. If the comparisons indicate that the level(s) of the one or more biomarkers are increasing or decreasing over time to become more similar to a younger metabolic age reference level (or less similar to an older metabolic age reference level), then the results are indicative of decreasing metabolic age.

As with the other methods described herein, the comparisons made in the methods of monitoring increasing/decreasing of metabolic age in a subject may be carried out using various techniques, including simple comparisons, one or more statistical analyses, and combinations thereof.

The results of the method may be used along with other methods (or the results thereof) useful in the clinical monitoring of increasing/decreasing of metabolic age in a subject. For example, the monitoring of metabolic age can be combined with a lifestyle assessment questionnaire to make recommendations for diet improvements and/or modifications; vitamin, mineral and/or other dietary supplements; and/or lifestyle modifications (e.g. quit smoking, drinking less alcohol, increasing exercise). Further, the measurement of metabolic age and/or monitoring increase/decrease in metabolic age can be combined with a lifestyle assessment questionnaire to determine risk factors for poor health and reduced longevity.

IV. Methods of Assessing Efficacy of Compositions for Modulating Metabolic Age

The identification of biomarkers for metabolic age also allows for assessment of the efficacy of a composition for modulating (e.g. increasing or decreasing) the metabolic age of a subject, as well as the assessment of the relative efficacy of two or more compounds or compositions for modulating the metabolic age of a subject. Such assessments may be used, for example, in efficacy studies as well as in lead selection of compounds or compositions for modulating metabolic age.

A method of assessing the efficacy of a composition for modulating metabolic age, comprises the steps of: (1) analyzing, from a subject having a first metabolic age, and currently or previously being treated with a compound or composition, a biological sample to determine the level(s) of one or more biomarkers selected from Tables 2, 7, and/or 8, and (2) comparing the level(s) of the one or more biomarkers in the sample to (a) level(s) of the one or more biomarkers in a previously-taken biological sample from the subject, wherein the previously-taken biological sample was obtained from the subject before being treated with the compound or composition, (b) metabolic age-positive reference levels of the one or more biomarkers, (c) metabolic age-negative reference levels of the one or more biomarkers, and/or (d) a target metabolic age reference level. The results of the comparison are indicative of the efficacy of the composition for modulating metabolic age.

Thus, in order to characterize the efficacy of the composition for modulating metabolic age, the level(s) of the one or more biomarkers in the biological sample are compared to (1) metabolic age-positive reference levels, (2) metabolic age-negative reference levels, (3) previous levels of the one or more biomarkers in the subject before treatment with the composition, and/or (d) a target metabolic age reference level.

When comparing the level(s) of the one or more biomarkers in the biological sample (from a subject having a particular metabolic age, and currently or previously being treated with a composition) to metabolic age-positive reference levels and/or metabolic age-negative reference levels and/or target metabolic age reference levels, level(s) in the sample matching the metabolic age-negative reference levels and/or target metabolic age reference levels (e.g., levels that are the same as the reference levels, substantially the same as the reference levels, above and/or below the minimum and/or maximum of the reference levels, and/or within the range of the reference levels) are indicative of the composition having efficacy for modulating metabolic age. Levels of the one or more biomarkers in the sample matching the metabolic age-positive reference levels (e.g., levels that are the same as the reference levels, substantially the same as the reference levels, above and/or below the minimum and/or maximum of the reference levels, and/or within the range of the reference levels) are indicative of the composition not having efficacy for modulating metabolic age. The comparisons may also indicate degrees of efficacy for modulating metabolic age, based on the level(s) of the one or more biomarkers.

When the level(s) of the one or more biomarkers in the biological sample (from a subject having a particular metabolic age and currently or previously being treated with a composition) are compared to level(s) of the one or more biomarkers in a previously-taken biological sample from the subject before treatment with the composition, any changes in the level(s) of the one or more biomarkers are indicative of the efficacy of the composition for modulating metabolic age. That is, if the comparisons indicate that the level(s) of the one or more biomarkers have increased or decreased after treatment with the composition to become more similar to the metabolic age-negative reference levels and/or target metabolic age reference levels (or less similar to the age-positive reference levels), then the results are indicative of the composition having efficacy for modulating metabolic age. If the comparisons indicate that the level(s) of the one or more biomarkers have not increased or decreased after treatment with the composition to become more similar to the metabolic age-negative reference levels and/or target metabolic age reference levels (or less similar to the metabolic age-positive reference levels), then the results are indicative of the composition not having efficacy for modulating metabolic age. The comparisons may also indicate degrees of efficacy for modulating metabolic age, based on the amount of changes observed in the level(s) of the one or more biomarkers after treatment. In order to help characterize such a comparison, the changes in the level(s) of the one or more biomarkers, the level(s) of the one or more biomarkers before treatment, and/or the level(s) of the one or more biomarkers in the subject currently or previously being treated with the composition may be compared to the metabolic age-positive and/or the metabolic age-negative reference levels and/or target metabolic age reference levels of the one or more biomarkers.

Another method for assessing the efficacy of a composition in modulating metabolic age, comprises the steps of: (1) analyzing a first biological sample from a subject to determine the level(s) of one or more biomarkers selected from Tables 2, 7, and/or 8, the first sample obtained from the subject at a first time point, (2) administering the composition to the subject, (3) analyzing a second biological sample from a subject to determine the level(s) of the one or more biomarkers, the second sample obtained from the subject at a second time point after administration of the composition, and (4) comparing the level(s) of one or more biomarkers in the first sample to the level(s) of the one or more biomarkers in the second sample in order to assess the efficacy of the composition for modulating metabolic age. As indicated above, if the comparison of the samples indicates that the level(s) of the one or more biomarkers have increased or decreased after administration of the composition to become more similar to the metabolic age-negative reference levels and/or target metabolic age reference levels (or less similar to the metabolic age-positive reference levels), then the results are indicative of the composition having efficacy for modulating metabolic age. If the comparison indicates that the level(s) of the one or more biomarkers have not increased or decreased after administration of the composition to become more similar to the metabolic age-negative reference levels and/or target metabolic age reference levels (or less similar to the metabolic age-positive reference levels), then the results are indicative of the composition not having efficacy for modulating metabolic age. The comparison may also indicate a degree of efficacy for modulating metabolic age, based on the amount of changes observed in the level(s) of the one or more biomarkers after administration of the composition. In order to help characterize such a comparison, the changes in the level(s) of the one or more biomarkers, the level(s) of the one or more biomarkers before administration of the composition, and/or the level(s) of the one or more biomarkers after administration of the composition may be compared to the metabolic age-positive and/or metabolic age—negative and/or target metabolic age reference levels of the one or more biomarkers of the two compositions.

A method of assessing the relative efficacy of two or more compositions for modulating metabolic age comprises the steps of: (1) analyzing, from a first subject having a particular metabolic score, and currently or previously being treated with a first composition, a first biological sample to determine the level(s) of one or more biomarkers selected from Tables 2, 7, and/or 8, (2) analyzing, from a second subject having the same or similar metabolic score, and currently or previously being treated with a second composition, a second biological sample to determine the level(s) of the one or more biomarkers, and (3) comparing the level(s) of one or more biomarkers in the first sample to the level(s) of the one or more biomarkers in the second sample in order to assess the relative efficacy of the first and second compositions for modulating metabolic age. The results are indicative of the relative efficacy of the two compositions, and the results (or the levels of the one or more biomarkers in the first sample and/or the level(s) of the one or more biomarkers in the second sample) may be compared to metabolic age-positive or metabolic age-negative or target metabolic age reference levels to aid in characterizing the relative efficacy.

Each of the methods of assessing efficacy may be conducted on one or more subjects or one or more groups of subjects (e.g., a first group being treated with a first composition and a second group being treated with a second composition).

As with the other methods described herein, the comparisons made in the methods of assessing efficacy (or relative efficacy) of compounds or compositions for modulating metabolic age, are carried out using various techniques, including simple comparisons, one or more statistical analyses, and combinations thereof. Any suitable method is used to analyze the biological samples in order to determine the level(s) of the one or more biomarkers in the samples. In addition, the level(s) of one or more biomarkers, including a combination of all of the biomarkers in Tables 2, 7, and/or 8 or any fraction thereof or using an index derived from all or some of the biomarkers in Tables 2, 7, and/or 8 may be determined and used in methods of assessing efficacy (or relative efficacy) of compositions for modulating metabolic age.

Finally, the methods of assessing efficacy (or relative efficacy) of one or more compounds or compositions for modulating metabolic age, may further comprise analyzing the biological sample to determine the level(s) of one or more non-biomarker compounds. The non-biomarker compounds may then be compared to reference levels of non-biomarker compounds for subjects having (or not having) the target metabolic age.

V. Methods of Screening a Composition for Activity in Modulating Biomarkers Associated with Metabolic Age The identification of biomarkers for metabolic age also allows for the screening of compositions for activity in modulating biomarkers associated with age which may be useful in modulating (increasing or decreasing) metabolic age of a subject. Methods of screening compositions useful for increasing or decreasing a subject's metabolic age comprises assaying test compositions for activity in modulating the levels of one or more metabolic age biomarkers in Tables 2, 4, 5, 7, and/or 8. Such screening assays may be conducted in vitro and/or in vivo, and may be in any form known in the art useful for assaying modulation of such metabolic age biomarkers in the presence of a test composition such as, for example, cell culture assays, organ culture assays, and in vivo assays (e.g., assays involving animal models).

In one embodiment, a method for screening a composition for activity in modulating one or more biomarkers of metabolic age comprises the steps of: (1) contacting one or more cells with a composition, (2) analyzing at least a portion of the one or more cells or a biological sample associated with the cells to determine the level(s) of one or more biomarkers of metabolic age selected from Tables 2, 4, 5, 7, and/or 8; and (3) comparing the level(s) of the one or more biomarkers with predetermined standard levels for the one or more biomarkers to determine whether the composition modulated the level(s) of the one or more biomarkers. As discussed above, the cells may be contacted with the composition in vitro and/or in vivo. The predetermined standard levels for the one or more biomarkers may be the levels of the one or more biomarkers in the one or more cells in the absence of the composition. The predetermined standard levels for the one or more biomarkers may also be the level(s) of the one or more biomarkers in control cells not contacted with the composition.

In addition, the methods may further comprise analyzing at least a portion of the one or more cells or a biological sample associated with the cells to determine the level(s) of one or more non-biomarker compounds of age. The levels of the non-biomarker compounds may then be compared to predetermined standard levels of the one or more non-biomarker compounds.

Any suitable method may be used to analyze at least a portion of the one or more cells or a biological sample associated with the cells in order to determine the level(s) of the one or more biomarkers (or levels of non-biomarker compounds). Suitable methods include chromatography (e.g., HPLC, gas chromatograph, liquid chromatography), mass spectrometry (e.g., MS, MS-MS), ELISA, antibody linkage, other immunochemical techniques, and combinations thereof. Further, the level(s) of the one or more biomarkers (or levels of non-biomarker compounds) may be measured indirectly, for example, by using an assay that measures the level of a compound (or compounds) that correlates with the level of the biomarker(s) (or non-biomarker compounds) that are desired to be measured.

VI. Method of Identifying Potential Drug Targets

The identification of biomarkers for metabolic age also allows for the identification of potential drug targets for metabolic aging. A method for identifying a potential drug target for metabolic aging comprises the steps of: (1) identifying one or more biochemical pathways associated with one or more metabolic age biomarkers selected from Tables 2, 4, 5, 7, and/or 8 and (2) identifying a protein (e.g., an enzyme) affecting at least one of the one or more identified biochemical pathways, the protein being a potential drug target for metabolic aging.

Another method for identifying a potential drug target for metabolic aging comprises the steps of: (1) identifying one or more biochemical pathways associated with one or more biomarkers for metabolic aging selected from Tables 2, 4, 5, 7, and/or 8 and one or more non-biomarker compounds of metabolic aging selected from Tables 2, 4, 5, 7, and/or 8; and (2) identifying a protein affecting at least one of the one or more identified biochemical pathways, the protein being a potential drug target for metabolic aging.

One or more biochemical pathways (e.g., biosynthetic and/or metabolic (catabolic) pathway) are identified that are associated with one or more biomarkers (or non-biomarker compounds). After the biochemical pathways are identified, one or more proteins affecting at least one of the pathways are identified. Preferably, those proteins affecting more than one of the pathways are identified. Examples of biochemical pathways are, but not limited to, glycolysis, the tricarboxylic acid cycle (TCA Cycle/Krebs Cycle/Citric Acid Cycle), the phosphogluconate pathway, oxidation-reduction and electron transport, oxidative phosphorylation and respiratory metabolism (respiration), fatty acid biosynthesis and oxidation (B-oxidation), amino acid biosynthesis and oxidative degradation, carbohydrate biosynthesis, gluconeogenesis, lipid biosynthesis, the HMG-CoA reductase pathway, the pentose phosphate pathway, the porphyrin synthesis pathway (heme synthesis), nitrogen metabolism (urea cycle), nucleotide biosynthesis, and DNA replication, transcription, and translation.

A build-up of one metabolite (e.g., a pathway intermediate) may indicate the presence of a 'block' downstream of the metabolite and the block may result in a low/absent level of a downstream metabolite (e.g. product of a biosynthetic pathway). In a similar manner, the absence of a metabolite could indicate the presence of a 'block' in the pathway upstream of the metabolite resulting from inactive or non-functional enzyme(s) or from unavailability of biochemical intermediates that are required substrates to produce the product. Alternatively, an increase in the level of a metabolite could indicate a genetic mutation that produces an aberrant protein which results in the over-production and/or accumulation of a metabolite which then leads to an alteration of other related biochemical pathways and result in dysregulation of the normal flux through the pathway; further, the build-up of the biochemical intermediate metabolite may be toxic or may compromise the production of a necessary intermediate for a related pathway. It is possible that the relationship between pathways is currently unknown and this data could reveal such a relationship.

The proteins identified as potential drug targets may then be used to identify compositions that may be potential candidates for treating metabolic aging including compositions for gene therapy.

VII. Methods of Treating a Subject Having a Positive Metabolic Score

The identification of biomarkers for metabolic age also allows for treatment of a subject having a positive metabolic score (or a negative metabolic age). For example, in order to treat a subject having a positive metabolic score, an effective amount of one or more metabolic age biomarkers that are at lower levels in an individual with a neutral metabolic score (a metabolic score that is not positive or negative) may be administered to the subject. The biomarkers that may be administered may comprise one or more of the biomarkers in Tables 2, 4, 5, 7, and/or 8, that are decreased in metabolic aging. Such biomarkers could be isolated based on the analytical characterizations for the biomarkers listed in Tables 2, 4, 5, 7, and/or 8. In some embodiments, the biomarkers that are administered are one or more biomarkers listed in Tables 2, 4, 5, 7, and/or 8, in particular Tables 2, 4, 5, 7, and/or 8, that are decreased in aging, and that have a p-value less than 0.05 and/or a q-value of less than 0.10.

In other embodiments, the biomarkers that are administered are one or biomarkers listed in Tables 2, 4, 5, 7, and/or 8, in particular Table 2 that are at decreased levels in aging, by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent).

VIII. Methods for Producing a Biochemical Age Index

The study of metabolomics and metabolic age can be used to determine a subject's fitness for a medical procedure or treatment. For example, one method for producing a Biochemical Age Index (BAI) comprises the steps of: (a) analyzing biological samples from a plurality of subjects to determine the level(s) of one or more biomarkers that change with age; (b) identifying one or more other biomarkers that correlate with each of the one or more initial biomarkers that change with age to generate one or more groups of biomarkers that change with age; and (c) generating a biochemical age index using the levels of each of the one or more groups of biomarkers. One example of a method of producing a BAI may be based on the determining the level(s) of one or more biomarkers listed in Tables 2, 4, 5, 7, and/or 8.

The samples used for producing a BAI may be based on any number of subjects, including 2, 3, 4, 5, 6, 7, 8, 9, 10, 15, 20, 25, 30, 35, 40, 45, 50, or 100 or more subjects.

The index may be produced by any method available for generating an index. In one aspect, the index is generated by plotting the level(s) of the one or more biomarkers, for example in a scatter plot. Such a scatter plot may then be fitted with a quadratic curve line.

In addition, the index may be tailored for a selected population, for example, populations based on gender or race or combinations of gender and race (e.g. black males, black females, white males, white females, Hispanic males, or Hispanic females).

IX. Methods of Using the Metabolic Age Biomarkers for Other Age Related Diseases It is believed that some of the biomarkers for metabolic aging described herein may also be biomarkers for other age related diseases in general. Therefore, it is believed that at least some of the aging biomarkers may be used in the methods described herein for aging related diseases in general. That is, the methods described herein with respect to aging may also be used for diagnosing (or aiding in the diagnosis of) an aging related disease, methods of monitoring progression/regression of an aging related disease, methods of assessing efficacy of compositions for treating an age related disease, methods of screening a composition for activity in modulating biomarkers associated with an aging related disease, methods of identifying potential drug targets for aging related diseases, and methods of treating an aging related disease. Such methods could be conducted as described herein with respect to metabolic aging.

X. Methods of Reporting and Making Recommendations

Following the metabolomic analysis, the resulting metabolic profile of the individual may be compared with metabolic profiles characteristic of different age groups to determine the metabolic age (MetabAge) or MetaboScore of the individual. Such comparisons may allow for the modification of the metabolic age of the subject. In one aspect, methods for the modification of the metabolic age of a subject comprise: (a) analyzing a biological sample from a subject to determine the level(s) of one or more biomarkers associated with metabolic age in the sample; (b) comparing the level(s) of the one or more biomarkers in the sample to metabolic age reference levels to determine the subject's metabolic age; and (c) providing recommendations to modify the metabolic age of the subject. In one aspect, the one or more biomarkers that are used are selected from Tables 2, 4, 5, 7, and/or 8 and combinations thereof.

A report may be provided that summarizes the results and provides recommendations directed to improving the metabolic age status of the individual. The final report includes, but is not limited to, the metabolic age (MetaboAge); the difference between an individual's chronological age and metabolic age (MetaboScore); a list of affected biochemical pathways (changed positively or negatively), nutritional recommendations (improve if not favorable or maintain if favorable), and therapeutic agents that may be useful in modifying the subject's metabolic age.

The metabolic age analysis methods can be combined with lifestyle assessment questionnaires to make recommendations for diet improvements and/or modifications; vitamin, mineral and/or other dietary supplements; and lifestyle modifications (e.g. quit smoking, drinking less alcohol, increasing exercise). Further, the methods and questionnaires can be combined to determine risk factors for poor health and reduced longevity.

XI. Method for Determining a Subject's Fitness for Medical Procedures or Treatments The study of metabolomics and metabolic age can be used to determine a subject's fitness for a medical procedure or treatment. For example, analyzing metabolic age is useful for, but not limited to, determining fitness for surgery, chemotherapy, physical therapy, or other medical treatments; determining dosage for anesthesia; determining requirement for additional diagnostic test; and determining drug treatments, regimens and/or dosages. The present invention relates to a method for determining a subject's fitness for medical procedures, surgery or treatments comprising the steps of:
- a) determining the metabolic age or profile or level of one or more age related biomarkers in a sample from the subject using the methods described in the present application;
- b) comparing the subject's metabolic age or profile or level to reference level(s) of one or more age related biomarkers or Biochemical Age Index (BAI); and
- c) determining the difference between the subject's metabolic age and chronological age to determine fitness for a medical procedure, surgery or treatment.

The present invention also relates to a method for determining a subject's fitness for anesthesia comprising the steps of:
- a) determining the metabolic age or profile or level of one or more age related biomarkers in a sample from the subject using the methods described in the present application;
- b) comparing the subject's metabolic age or profile or level to reference level(s) of one or more age related biomarkers or Biochemical Age Index (BAI); and
- c) determining the difference between the subject's metabolic age and chronological age to determine fitness for anesthesia.

XII. Method for Determining Risk Factors for Illness and/or Disease

Analyzing a subject's metabolic age is also useful for determining a subject's risk factors for illness and/or disease. The present invention relates to a method for determining a subject's risk factors for illness and/or disease comprising the steps of:
- a) determining the metabolic age or profile or level of one or more age related biomarkers in a sample from the subject using the methods described in the present application;
- b) comparing the subject's metabolic age or profile or level to reference level(s) of one or more age related biomarkers or Biochemical Age Index (BAI); and
- c) determining the difference between the subject's metabolic age and chronological age to determine risk factors for illness and/or disease.

XIII. Methods for Analyzing Xenobiotics and Xenobiotic Score

Xenobiotics are also present in samples from subjects and can be analyzed with relation to age of subjects just as metabolites. A method to determine a Xenobiotic Score for a subject comprises the steps of: a) analyzing a biological sample from a subject to determine the level(s) of one or more xenobiotics in the sample; b) comparing the level(s) of the one or more xenobiotics in the sample to a xenobiotic reference levels of the one or more xenobiotics in order to determine the subject's xenobiotic level; and c) calculating the difference between the subject's xenobiotic level and the xenobiotic reference level to determine the xenobiotic score.

The Xenobiotic Score can be used to provide recommendations on dietary improvements or modifications, lifestyle changes (e.g. quit smoking, drink less alcohol, increase exercise) and/or vitamins, minerals and/or dietary supplements. Further, lifestyle assessment questionnaires can also be combined with the xenobiotic analysis and score to make recommendations to improve health and xenobiotic levels.

EXAMPLES

The invention will be further explained by the following illustrative examples that are intended to be non-limiting.

Example 1

Identification of Metabolic Age Biomarkers

This example describes determination of metabolites that vary in level with age, gender and race of humans.

Sample Preparation

Human plasma samples shown in Table 1 were obtained from Bioreclamation, Inc. (East Meadow, N.Y.). The sample preparation process was carried out using the automated MicroLab STAR® liquid-handling system from Hamilton Company. Recovery standards were added prior to the first step in the extraction process for Quality Control (QC) purposes. Sample preparation was conducted using a proprietary series of organic and aqueous extractions to remove sample proteins, while maximizing the recovery of small molecules. The resulting extract was divided into two fractions, one for analysis by polar liquid chromatography (LC), and the other for analysis by gas chromatography (GC). A TurboVap® (Zymark) was used to remove the organic solvent. Each sample was then frozen and dried under vacuum. Samples were then prepared for the appropriate analysis system, either LC/MS or GC/MS.

TABLE 1

Composition of subjects by age group, gender, and self-reported race.

| Gender | Age 25-35 | Age 36-50 | Age 51-65 | Total |
|---|---|---|---|---|
| Male | 47 | 34 | 49 | 130 |
| Female | 43 | 56 | 41 | 140 |
| Race | Male/Female | Male/Female | Male/Female | |
| Asian | 0/0 | 1/0 | 0/0 | 1 |
| Black | 28/25 (53) | 15/27 (42) | 22/15 (37) | 132 |
| Hispanic | 9/8 (17) | 13/13 (26) | 21/11 (32) | 75 |
| White | 10/10 (20) | 5/16 (21) | 6/15 (21) | 62 |
| Total | 47/43 (90) | 34/56 (90) | 49/41 (90) | 270 |

Liquid Chromatography/Mass Spectrometry (LC/MS)

The LC/MS system consisted of a Surveyor HPLC (Thermo-Electron, Waltham, Mass.) and a LTQ linear ion-trap mass spectrometer (Thermo-Electron, Waltham, Mass.). Compounds were eluted via an aqueous/organic solvent gradient and ionized via electrospray ionization (ESI). Continuous, alternating polarity switching was employed so as to be able to generate both positive and negative ions consecutively.

The vacuum-dried sample was dissolved in 100 µl of an injection solvent that contained five or more injection standards at fixed concentrations. The chromatographic system used a binary solvent system, which was delivered as a gradient, where solvent A was water and solvent B was methanol. Both were high purity grade and contained 0.1% formic acid as a pH stabilizer. The HPLC column was a Thermo AquaSil C-18 (100 mm L×2.1 mm ID). Metabolites that were identified using LC-MS are denoted by the number 35 in the "Library" column in Tables 2-12.

Gas Chromatography/Mass Spectrometry (GC/MS)

The CC samples were dried under vacuum for a minimum of 24 hours prior to being derivatized under dried nitrogen using bistrimethyl-silyl-triflouroacetamide (BSTFA). The CC column (Restek, Bellefonte, Pa.) was 5% phenyl. Elution was effected by a temperature ramp from 40° C. to 300° C. in a 16 minute period. The mass spectrometer consisted of a TraceDSQ (Thermo-Electron, Waltham, Mass.) single-quadrupole mass spectrometer. Ionization was accomplished via electron impact (EI). Metabolites that were identified using GC-MS are denoted by the number 50 in the "Library" column in Tables 2-11.

Data Processing

Data processing was performed using Metabolon's custom developed informatics platform, which consisted of four major components, the Metabolon Laboratory Information Management System (MLIMS), the data extraction and peak-identification software, data processing tools for QC and compound identification, and a collection of information interpretation and visualization tools for use by data analysts.

Compound Identification

Compounds were identified by comparison to library entries of purified standards or recurrent, unnamed entities. Identification of known chemical entities was based on comparison to metabolomic library entries of purified standards purchased from a variety of vendors.

Statistical Calculations

Statistical analysis of the data was performed using JMP (SAS, available on the worldwide web at jmp.com), a commercial software package, and "R" (available on the worldwide web at r-project.org), which is a freely available open-source, software package.

Table 1 contains the data describing the cohort by age, race and gender for the 270 samples used in this study.

For statistical analysis, ANOVA was performed on the full factorial. A log transform was applied to the observed relative concentrations for each compound because, in general, the variance increased as a function of a compound's average response. Some compounds, especially xenobiotics, have "sparse" responses, where many samples will not have a reported value. In order to be included in the statistical analysis, a compound had to have a response for at least 80% of the samples in one of age, race and gender combinations shown in Table 1. In cases where a response was missing, we assumed that the value was missing because the compound was below the limit of detection. For these cases, a value was imputed with the minimum response for that compound, which is conservative for estimating the mean. Finally, in order to limit false discoveries, we computed q-values (Benjamini, Y. and Y. Hochberg, 1995, Journal of the Royal Statistical Society, Series B, 57.289-300). In addition to looking for differences by age, race and gender, we also looked for interactions between these factors. For the most part, no strong interactions were observed. However, we did observe that urea levels might be influenced both by age and gender.

Listed in Table 2 are the named and unnamed metabolites that were detected in the plasma collected from the individuals described in Table 1 and analyzed based upon age groupings. The "Library" column indicates whether the compound was detected using GC-MS or LC-MS. CC-MS metabolites are indicated by "50" while "35" indicates LC-MS metabolites. The mean level for each compound for each age group is indicated in the columns by age group (25-35, 36-50, 51-65). Statistical significance is indicated by the p-value and the false discovery rate is indicated by the q-value. The "Comp ID" column refers to the internal database tracking number for that compound in our chemical library.

TABLE 2

Compounds that change with age.

| COMP ID | COMPOUND | Library | p-value | q-value | 20-35 years | 36-50 years | 51-65 years | Change with age (youngest to oldest) |
|---|---|---|---|---|---|---|---|---|
| 16511 | Metabolite - 4274 | 50 | 2.06E−22 | 2.09E−20 | 0.65 | 1.03 | 1.62 | Increase |
| 9313 | Metabolite - 2172 | 35 | 1.35E−20 | 5.18E−19 | 0.23 | 0.50 | 1.37 | Increase |
| 12769 | Metabolite - 3089 | 50 | 1.77E−20 | 5.18E−19 | 0.27 | 0.55 | 1.20 | Increase |
| 1493 | ornithine | 50 | 2.04E−20 | 5.18E−19 | 0.56 | 1.10 | 1.73 | Increase |
| 12767 | Metabolite - 3087 | 50 | 9.85E−20 | 2.00E−18 | 0.65 | 1.00 | 1.46 | Increase |
| 12593 | Metabolite - 2973 | 50 | 9.56E−19 | 1.39E−17 | 0.70 | 0.97 | 1.31 | Increase |
| 16332 | Metabolite - 4164 | 35 | 3.26E−18 | 4.14E−17 | 0.79 | 0.96 | 1.21 | Increase |
| 12790 | Metabolite - 3108 | 50 | 5.17E−16 | 5.26E−15 | 0.82 | 1.00 | 1.23 | Increase |
| 57 | glutamic acid | 50 | 6.21E−16 | 5.74E−15 | 0.53 | 1.08 | 1.47 | Increase |
| 11777 | glycine | 50 | 2.56E−15 | 2.17E−14 | 0.67 | 1.02 | 1.47 | Increase |
| 21025 | iminodiacetic acid | 50 | 3.10E−15 | 2.42E−14 | 0.22 | 0.64 | 4.39 | Increase |
| 1126 | alanine | 50 | 3.40E−15 | 2.47E−14 | 0.72 | 1.03 | 1.42 | Increase |
| 12770 | Metabolite - 3090 | 50 | 1.95E−14 | 1.32E−13 | 0.22 | 0.66 | 2.47 | Increase |
| 19934 | inositol | 50 | 3.06E−14 | 1.94E−13 | 0.83 | 1.09 | 1.18 | Increase |
| 60 | leucine | 50 | 4.66E−14 | 2.79E−13 | 0.71 | 1.07 | 1.40 | Increase |
| 1649 | valine | 50 | 5.20E−14 | 2.94E−13 | 0.70 | 1.01 | 1.33 | Increase |
| 1301 | lysine | 50 | 7.10E−13 | 3.80E−12 | 0.64 | 1.07 | 1.53 | Increase |
| 12669 | Metabolite - 3036 | 50 | 8.86E−13 | 4.50E−12 | 0.58 | 0.80 | 1.24 | Increase |
| 10461 | Metabolite - 2313 | 35 | 3.20E−12 | 1.55E−11 | 0.78 | 1.04 | 1.56 | Increase |
| 13257 | Metabolite - 3218 | 35 | 3.49E−12 | 1.61E−11 | 0.83 | 1.00 | 1.14 | Increase |
| 12784 | Metabolite - 3102 | 50 | 1.01E−11 | 4.46E−11 | 0.89 | 0.99 | 1.20 | Increase |
| 15063 | Metabolite - 3772 | 35 | 2.58E−11 | 1.09E−10 | 0.64 | 1.16 | 1.46 | Increase |
| 1125 | isoleucine | 50 | 3.74E−11 | 1.52E−10 | 0.72 | 1.03 | 1.35 | Increase |
| 594 | niacinamide | 35 | 4.32E−11 | 1.69E−10 | 0.52 | 0.81 | 1.05 | Increase |
| 11323 | Metabolite - 2711 | 35 | 9.42E−11 | 3.42E−10 | 0.68 | 1.10 | 1.45 | Increase |
| 1648 | serine | 50 | 1.10E−10 | 3.86E−10 | 0.75 | 1.04 | 1.30 | Increase |
| 20699 | meso-erythritol | 50 | 2.56E−10 | 8.67E−10 | 0.93 | 0.98 | 1.24 | Increase |

TABLE 2-continued

Compounds that change with age.

| COMP ID | COMPOUND | Library | p-value | q-value | 20-35 years | 36-50 years | 51-65 years | Change with age (youngest to oldest) |
|---|---|---|---|---|---|---|---|---|
| 3147 | xanthine | 35 | 4.91E−10 | 1.61E−09 | 0.58 | 0.76 | 1.27 | Increase |
| 1647 | glutamine | 50 | 5.73E−10 | 1.82E−09 | 0.75 | 0.92 | 1.49 | Increase |
| 527 | lactate | 50 | 1.05E−09 | 3.23E−09 | 0.73 | 1.05 | 1.23 | Increase |
| 1303 | malic acid | 50 | 3.15E−09 | 9.15E−09 | 0.79 | 1.11 | 1.31 | Increase |
| 12644 | Metabolite - 3016 | 50 | 4.41E−08 | 1.18E−07 | 0.87 | 0.99 | 1.10 | Increase |
| 1284 | threonine | 50 | 1.03E−07 | 2.68E−07 | 0.82 | 1.04 | 1.28 | Increase |
| 59 | histidine | 50 | 1.09E−07 | 2.77E−07 | 0.77 | 1.09 | 1.18 | Increase |
| 12774 | Metabolite - 3094 | 50 | 1.20E−07 | 2.98E−07 | 0.85 | 0.99 | 1.13 | Increase |
| 3127 | hypoxanthine | 35 | 3.63E−07 | 8.58E−07 | 0.41 | 0.84 | 1.36 | Increase |
| 569 | caffeine | 35 | 4.23E−07 | 9.77E−07 | 0.28 | 0.70 | 1.16 | Increase |
| 16135 | Metabolite - 4077 | 50 | 5.39E−07 | 1.22E−06 | 0.67 | 0.89 | 1.19 | Increase |
| 1437 | succinate | 50 | 5.51E−07 | 1.22E−06 | 0.76 | 1.08 | 1.09 | Increase |
| 1113 | isocitrate | 35 | 1.67E−06 | 3.46E−06 | 0.76 | 1.02 | 1.26 | Increase |
| 12795 | Metabolite - 3113 | 50 | 1.87E−06 | 3.80E−06 | 0.61 | 0.89 | 1.17 | Increase |
| 1584 | Metabolite - 1003 | 35 | 2.16E−06 | 4.31E−06 | 0.78 | 0.93 | 1.05 | Increase |
| 16070 | Metabolite - 4019 | 50 | 2.46E−06 | 4.81E−06 | 0.85 | 0.94 | 1.12 | Increase |
| 1107 | allantoin | 50 | 3.79E−06 | 7.13E−06 | 0.64 | 0.93 | 1.15 | Increase |
| 1508 | pantothenic acid | 35 | 3.91E−06 | 7.23E−06 | 0.84 | 1.05 | 1.25 | Increase |
| 12783 | Metabolite - 3101 | 50 | 3.99E−06 | 7.24E−06 | 0.84 | 0.97 | 1.12 | Increase |
| 606 | uridine | 35 | 4.90E−06 | 8.74E−06 | 0.89 | 0.98 | 1.18 | Increase |
| 5803 | Metabolite - 1190 | 35 | 5.09E−06 | 8.92E−06 | 0.38 | 0.85 | 0.88 | Increase |
| 1494 | 5-oxoproline | 50 | 8.40E−06 | 1.43E−05 | 0.87 | 1.05 | 1.13 | Increase |
| 11438 | phosphate | 50 | 8.46E−06 | 1.43E−05 | 0.90 | 0.97 | 1.06 | Increase |
| 10347 | Metabolite - 2285 | 35 | 1.13E−05 | 1.88E−05 | 0.67 | 0.87 | 1.16 | Increase |
| 15529 | Metabolite - 3951 | 35 | 1.15E−05 | 1.89E−05 | 0.92 | 0.99 | 1.13 | Increase |
| 15140 | L-kynurenine | 35 | 1.48E−05 | 2.39E−05 | 0.98 | 0.95 | 1.16 | Increase |
| 6413 | Metabolite - 1342-possible-phenylacetylglutamine | 35 | 2.20E−05 | 3.44E−05 | 0.65 | 1.05 | 1.16 | Increase |
| 18254 | paraxanthine | 35 | 4.01E−05 | 1.00E−04 | 0.32 | 0.69 | 0.81 | Increase |
| 13296 | Metabolite - 3230 | 35 | 1.00E−04 | 1.00E−04 | 0.96 | 1.02 | 1.12 | Increase |
| 14837 | Metabolite - 3707 | 35 | 1.00E−04 | 1.00E−04 | 0.66 | 0.88 | 1.28 | Increase |
| 15234 | Metabolite - 3821 | 35 | 1.00E−04 | 1.00E−04 | 0.75 | 0.81 | 0.96 | Increase |
| 7359 | Metabolite - 1713 | 35 | 1.00E−04 | 2.00E−04 | 0.67 | 1.03 | 1.17 | Increase |
| 5800 | Metabolite - 1188 | 35 | 2.00E−04 | 3.00E−04 | 0.31 | 0.75 | 0.71 | Increase |
| 9130 | Metabolite - 2139 | 35 | 2.00E−04 | 3.00E−04 | 0.90 | 1.02 | 1.16 | Increase |
| 1519 | sucrose | 50 | 3.00E−04 | 5.00E−04 | 0.36 | 0.61 | 0.91 | Increase |
| 16067 | Metabolite - 4017 | 50 | 4.00E−04 | 5.00E−04 | 0.90 | 0.95 | 1.10 | Increase |
| 1670 | urea | 50 | 4.00E−04 | 5.00E−04 | 0.88 | 1.04 | 1.19 | Increase |
| 1358 | octadecanoic acid | 50 | 4.00E−04 | 6.00E−04 | 0.93 | 1.03 | 1.08 | Increase |
| 7029 | Metabolite - 1597 | 35 | 5.00E−04 | 6.00E−04 | 0.92 | 1.03 | 1.03 | Increase |
| 10154 | Metabolite - 2258- | 35 | 5.00E−04 | 7.00E−04 | 0.78 | 0.98 | 1.11 | Increase |
| 1574 | histamine | 35 | 6.00E−04 | 7.00E−04 | 0.95 | 0.99 | 1.14 | Increase |
| 5689 | Metabolite - 1111 | 35 | 7.00E−04 | 8.00E−04 | 0.96 | 0.93 | 1.13 | Increase |
| 528 | alpha-keto-glutarate | 35 | 7.00E−04 | 9.00E−04 | 0.64 | 1.07 | 1.00 | Increase |
| 11222 | Metabolite - 2688 | 35 | 7.00E−04 | 9.00E−04 | 0.57 | 0.89 | 0.85 | Increase |
| 6424 | Metabolite - 1346 | 35 | 8.00E−04 | 0.001 | 0.93 | 0.99 | 1.08 | Increase |
| 6130 | Metabolite - 1208 | 35 | 9.00E−04 | 0.001 | 0.43 | 0.74 | 0.86 | Increase |
| 5580 | Metabolite - 1067 | 35 | 0.0011 | 0.0012 | 0.80 | 1.31 | 1.45 | Increase |
| 12864 | Metabolite - 3124 | 35 | 0.0011 | 0.0013 | 0.80 | 0.94 | 1.02 | Increase |
| 6136 | Metabolite - 1211-IHWESASLLR | 35 | 0.0013 | 0.0014 | 0.38 | 0.91 | 0.83 | Increase |
| 12720 | Metabolite - 3056 | 35 | 0.0014 | 0.0015 | 0.86 | 0.96 | 1.07 | Increase |
| 16496 | Metabolite - 4251 | 50 | 0.0015 | 0.0016 | 0.72 | 0.95 | 1.11 | Increase |
| 1444 | Isobar-56: DL-pipecolic acid/1-amino-cyclopentanecarboxylic acid | 35 | 0.0021 | 0.0021 | 0.98 | 1.32 | 1.19 | Increase |
| 6122 | Metabolite - 1206 | 35 | 0.0021 | 0.0021 | 0.40 | 0.76 | 0.59 | Increase |
| 5664 | Metabolite - 1215 | 35 | 0.0021 | 0.0021 | 0.48 | 1.11 | 0.98 | Increase |
| 12785 | Metabolite - 3103 | 50 | 0.0021 | 0.0021 | 0.25 | 0.49 | 0.75 | Increase |
| 15753 | hippuric acid | 35 | 0.0022 | 0.0021 | 0.81 | 1.14 | 1.23 | Increase |
| 10921 | Metabolite - 2558 | 35 | 0.0023 | 0.0022 | 0.30 | 0.21 | 0.58 | Increase |
| 10672 | Metabolite - 2390 | 35 | 0.0032 | 0.0031 | 0.87 | 0.98 | 1.12 | Increase |
| 6362 | Metabolite - 1323-possible-p-cresol-sulfate | 35 | 0.0043 | 0.004 | 0.58 | 0.81 | 1.05 | Increase |
| 1123 | inosine | 35 | 0.0047 | 0.0044 | 0.62 | 0.92 | 1.05 | Increase |
| 6236 | Metabolite - 1983 | 35 | 0.0052 | 0.0048 | 0.36 | 0.68 | 0.63 | Increase |
| 12352 | Metabolite - 2871 | 35 | 0.0053 | 0.0048 | 0.70 | 0.92 | 0.98 | Increase |
| 6215 | Metabolite - 1261 | 35 | 0.0059 | 0.0052 | 0.48 | 0.91 | 0.83 | Increase |
| 12754 | Metabolite - 3075 | 50 | 0.0072 | 0.0063 | 0.75 | 0.94 | 0.93 | Increase |
| 15663 | Metabolite - 1000 | 35 | 0.0078 | 0.0068 | 0.64 | 1.00 | 0.86 | Increase |

TABLE 2-continued

Compounds that change with age.

| COMP ID | COMPOUND | Library | p-value | q-value | 20-35 years | 36-50 years | 51-65 years | Change with age (youngest to oldest) |
|---|---|---|---|---|---|---|---|---|
| 6138 | Metabolite - 1213 | 35 | 0.008 | 0.0069 | 0.56 | 0.90 | 1.02 | Increase |
| 7933 | Metabolite - 1911 | 35 | 0.0088 | 0.0074 | 0.51 | 0.84 | 0.90 | Increase |
| 6112 | Metabolite - 1203-HXGXA | 35 | 0.0089 | 0.0074 | 0.30 | 0.75 | 0.64 | Increase |
| 15681 | 4-Guanidinobutanoic acid | 35 | 0.0092 | 0.0075 | 0.95 | 1.00 | 1.06 | Increase |
| 13744 | Metabolite - 3364 | 35 | 0.01 | 0.008 | 0.63 | 0.83 | 1.03 | Increase |
| 8336 | Metabolite - 2005 | 35 | 0.0104 | 0.0083 | 0.90 | 0.91 | 1.12 | Increase |
| 5687 | Metabolite - 1110 | 35 | 0.0118 | 0.0093 | 0.71 | 0.91 | 1.11 | Increase |
| 10245 | Metabolite - 2269 | 35 | 0.0135 | 0.0105 | 0.72 | 0.89 | 1.10 | Increase |
| 6204 | Metabolite - 1252 | 35 | 0.0136 | 0.0105 | 0.35 | 0.71 | 0.47 | Increase |
| 12626 | Metabolite - 3003 | 50 | 0.0136 | 0.0105 | 0.96 | 1.02 | 1.07 | Increase |
| 10785 | Metabolite - 2506 | 35 | 0.0137 | 0.0105 | 0.71 | 1.01 | 1.15 | Increase |
| 12777 | Metabolite - 3097 | 50 | 0.0177 | 0.0134 | 0.86 | 1.09 | 1.13 | Increase |
| 27718 | creatine | 35 | 0.0178 | 0.0134 | 0.87 | 1.02 | 1.11 | Increase |
| 6239 | Metabolite - 1264 | 35 | 0.0187 | 0.0139 | 0.43 | 0.90 | 0.67 | Increase |
| 10309 | Metabolite - 2277 | 35 | 0.0189 | 0.0139 | 0.66 | 1.01 | 0.79 | Increase |
| 15991 | L-alpha-glycerophosphorylcholine | 35 | 0.0191 | 0.014 | 0.70 | 0.93 | 0.97 | Increase |
| 7424 | Metabolite - 1718 | 35 | 0.0192 | 0.014 | 0.26 | 0.63 | 0.37 | Increase |
| 6231 | Metabolite - 1262 | 35 | 0.0209 | 0.0151 | 0.40 | 0.83 | 0.56 | Increase |
| 5798 | Metabolite - 1187 | 35 | 0.0217 | 0.0155 | 0.32 | 0.62 | 0.47 | Increase |
| 7644 | Metabolite - 1831 | 35 | 0.0238 | 0.0168 | 0.84 | 0.95 | 1.02 | Increase |
| 27741 | cis/trans-aconitic acid | 35 | 0.0281 | 0.0195 | 0.99 | 1.06 | 1.24 | Increase |
| 1561 | alpha-tocopherol | 50 | 0.0289 | 0.02 | 0.91 | 0.95 | 1.11 | Increase |
| 11111 | Metabolite - 2592 | 35 | 0.0294 | 0.0202 | 0.89 | 1.40 | 1.00 | Increase |
| 6296 | Metabolite - 1303-SHAXQXNNR | 35 | 0.031 | 0.0212 | 0.48 | 0.80 | 0.59 | Increase |
| 12646 | Metabolite - 3018 | 50 | 0.0323 | 0.0218 | 0.92 | 1.01 | 0.99 | Increase |
| 64 | phenylalanine | 35 | 0.0323 | 0.0218 | 0.96 | 1.02 | 1.05 | Increase |
| 1431 | p-hydroxyphenyllactic acid | 35 | 0.0327 | 0.0219 | 0.77 | 0.93 | 0.92 | Increase |
| 22130 | DL-phenyllactic acid | 35 | 0.0331 | 0.022 | 0.87 | 1.05 | 1.11 | Increase |
| 6208 | Metabolite - 1254 | 35 | 0.0342 | 0.0226 | 0.62 | 1.09 | 1.14 | Increase |
| 12751 | Metabolite - 3073 | 50 | 0.0364 | 0.0237 | 0.89 | 1.09 | 0.98 | Increase |
| 5724 | Metabolite - 1125 | 35 | 0.0369 | 0.0239 | 0.55 | 0.77 | 0.56 | Increase |
| 15506 | choline | 35 | 0.0381 | 0.0245 | 0.99 | 1.02 | 1.11 | Increase |
| 16138 | Metabolite - 4080 | 50 | 0.041 | 0.0261 | 0.89 | 1.08 | 0.92 | Increase |
| 1105 | linoleic acid | 50 | 0.0415 | 0.0262 | 0.93 | 1.06 | 1.07 | Increase |
| 15677 | 3-methyl-L-histidine/1-methyl-L-histidine | 35 | 0.0457 | 0.0284 | 0.53 | 0.72 | 0.82 | Increase |
| 10092 | Metabolite - 2250 | 35 | 0.0493 | 0.0302 | 0.41 | 0.55 | 0.68 | Increase |
| 54 | tryptophan | 35 | 0.0506 | 0.0308 | 1.00 | 0.95 | 1.03 | Increase |
| 10083 | Metabolite - 2248 | 35 | 0.0528 | 0.032 | 0.49 | 0.71 | 0.79 | Increase |
| 5733 | Metabolite - 1127 | 35 | 0.0599 | 0.0358 | 0.90 | 1.06 | 0.93 | Increase |
| 5577 | Metabolite - 1065 | 35 | 0.0617 | 0.0362 | 0.69 | 1.31 | 0.99 | Increase |
| 15769 | carnitine | 35 | 0.062 | 0.0362 | 0.92 | 0.96 | 1.03 | Increase |
| 18392 | theobromine | 35 | 0.0665 | 0.0381 | 0.69 | 0.73 | 1.00 | Increase |
| 5669 | Metabolite - 1104 | 35 | 0.0669 | 0.0381 | 0.92 | 1.04 | 1.04 | Increase |
| 63 | cholesterol | 50 | 0.069 | 0.039 | 0.92 | 0.95 | 1.12 | Increase |
| 6787 | Metabolite - 1465 | 35 | 0.074 | 0.0411 | 0.90 | 1.04 | 0.99 | Increase |
| 21044 | 2-hydroxybutyric acid | 50 | 0.0752 | 0.0415 | 0.90 | 1.07 | 1.08 | Increase |
| 10304 | Metabolite - 2276 | 35 | 0.0841 | 0.0459 | 0.67 | 1.00 | 0.77 | Increase |
| 14933 | Metabolite - 3739 | 35 | 0.0879 | 0.0478 | 0.65 | 0.59 | 0.85 | Increase |
| 10478 | Metabolite - 2317 | 35 | 0.0915 | 0.0493 | 0.51 | 0.77 | 0.63 | Increase |
| 16091 | Metabolite - 4031 | 35 | 0.0916 | 0.0493 | 0.89 | 0.98 | 1.01 | Increase |
| 12710 | Metabolite - 3052 | 35 | 0.0921 | 0.0493 | 0.90 | 1.03 | 0.93 | Increase |
| 16518 | Metabolite - 4276 | 50 | 0.095 | 0.0506 | 0.78 | 0.97 | 0.90 | Increase |
| 15596 | Metabolite - 3962 | 35 | 0.0973 | 0.0514 | 1.03 | 1.15 | 1.16 | Increase |
| 15683 | 4-methyl-2-oxopentanoate | 50 | 0.0976 | 0.0514 | 0.93 | 1.05 | 1.02 | Increase |
| 12759 | Metabolite - 3080 | 50 | 0.0982 | 0.0515 | 0.98 | 1.09 | 1.09 | Increase |
| 10317 | Metabolite - 2279 | 35 | 0.1032 | 0.0535 | 0.55 | 0.67 | 0.71 | Increase |
| 10296 | Metabolite - 2273 | 35 | 0.1041 | 0.0535 | 0.48 | 0.65 | 0.71 | Increase |
| 1604 | uric acid | 35 | 0.1062 | 0.0542 | 0.97 | 1.00 | 1.02 | Increase |
| 1299 | tyrosine | 35 | 0.1122 | 0.0567 | 0.97 | 1.00 | 1.06 | Increase |
| 12856 | Metabolite - 3123 | 35 | 0.1285 | 0.064 | 0.75 | 1.05 | 0.79 | Increase |
| 12791 | Metabolite - 3109 | 50 | 0.1318 | 0.0653 | 0.92 | 0.82 | 1.00 | Increase |
| 1591 | N-acetyl-L-valine | 35 | 0.1459 | 0.0716 | 0.83 | 0.87 | 0.92 | Increase |
| 1336 | n-hexadecanoic acid | 50 | 0.1482 | 0.0721 | 0.98 | 1.09 | 1.07 | Increase |
| 1359 | oleic acid | 50 | 0.1517 | 0.0734 | 0.89 | 1.05 | 1.03 | Increase |
| 6398 | Metabolite - 1335 | 35 | 0.1602 | 0.0768 | 0.91 | 0.96 | 1.09 | Increase |
| 5809 | 3-indoxyl-sulfate | 35 | 0.1642 | 0.0784 | 0.93 | 0.92 | 1.10 | Increase |

TABLE 2-continued

Compounds that change with age.

| COMP ID | COMPOUND | Library | p-value | q-value | 20-35 years | 36-50 years | 51-65 years | Change with age (youngest to oldest) |
|---|---|---|---|---|---|---|---|---|
| 14785 | Isobar-glycochenodeoxycholic acid-glycodeoxycholic acid | 35 | 0.1738 | 0.0826 | 0.70 | 0.98 | 0.81 | Increase |
| 542 | 3-hydroxybutanoic acid | 50 | 0.1793 | 0.0844 | 1.02 | 1.38 | 1.29 | Increase |
| 14239 | Metabolite - 3474 | 35 | 0.1853 | 0.0868 | 0.83 | 0.95 | 0.83 | Increase |
| 10424 | Metabolite - 2292 | 35 | 0.1877 | 0.0875 | 0.64 | 0.55 | 0.75 | Increase |
| 1110 | arachidonic acid | 50 | 0.19 | 0.0882 | 0.92 | 0.97 | 1.02 | Increase |
| 5609 | Metabolite - 1083 | 35 | 0.1989 | 0.0918 | 0.12 | 0.26 | 0.17 | Increase |
| 18349 | DL-indole-3-lactic acid | 35 | 0.2003 | 0.0918 | 0.95 | 0.91 | 1.04 | Increase |
| 12781 | Metabolite - 3099 | 50 | 0.2005 | 0.0918 | 0.91 | 1.05 | 1.06 | Increase |
| 10087 | Metabolite - 2249 | 35 | 0.2088 | 0.0939 | 1.01 | 0.94 | 1.05 | Increase |
| 15128 | Metabolite - 1002 | 35 | 0.2126 | 0.0952 | 0.99 | 1.17 | 1.05 | Increase |
| 6402 | Metabolite - 3832 | 35 | 0.2216 | 0.0984 | 1.09 | 1.10 | 1.32 | Increase |
| 12924 | Metabolite - 3131 | 35 | 0.2245 | 0.0992 | 0.89 | 1.06 | 0.99 | Increase |
| 9561 | Metabolite - 2193 | 35 | 0.2255 | 0.0992 | 0.50 | 0.74 | 0.64 | Increase |
| 10782 | Metabolite - 2486 | 35 | 0.2511 | 0.1091 | 0.88 | 1.05 | 1.01 | Increase |
| 1121 | heptadecanoic acid | 50 | 0.2651 | 0.1147 | 0.95 | 0.98 | 1.04 | Increase |
| 16055 | Metabolite - 4012 | 50 | 0.2678 | 0.1153 | 0.89 | 0.93 | 1.00 | Increase |
| 11499 | Metabolite - 2753 | 35 | 0.2829 | 0.1214 | 0.95 | 1.03 | 0.99 | Increase |
| 10715 | Metabolite - 2395 | 35 | 0.3021 | 0.1274 | 0.81 | 1.04 | 0.83 | Increase |
| 8091 | glycocholic acid | 35 | 0.3105 | 0.1304 | 0.71 | 0.93 | 0.87 | Increase |
| 10570 | Metabolite - 2366 | 35 | 0.3118 | 0.1304 | 0.86 | 0.96 | 1.02 | Increase |
| 16071 | Metabolite - 4020 | 50 | 0.3139 | 0.1308 | 0.88 | 0.87 | 0.98 | Increase |
| 13605 | Metabolite - 4868 | 35 | 0.3197 | 0.1326 | 0.53 | 0.77 | 0.60 | Increase |
| 10774 | Metabolite - 2466 | 35 | 0.3641 | 0.1491 | 0.50 | 0.72 | 0.66 | Increase |
| 14755 | Metabolite - 3664 | 35 | 0.3653 | 0.1491 | 0.69 | 0.83 | 0.80 | Increase |
| 9491 | Metabolite - 2185 | 35 | 0.3925 | 0.1589 | 0.94 | 0.97 | 1.04 | Increase |
| 15122 | glycerol | 50 | 0.3955 | 0.1596 | 1.00 | 1.04 | 1.09 | Increase |
| 10781 | Metabolite - 2469 | 35 | 0.4135 | 0.1662 | 0.85 | 1.00 | 0.93 | Increase |
| 10414 | Metabolite - 2291 | 35 | 0.4238 | 0.1685 | 0.64 | 0.67 | 0.80 | Increase |
| 15328 | azelaic acid | 35 | 0.4242 | 0.1685 | 0.97 | 1.04 | 1.01 | Increase |
| 15278 | Metabolite - 3843 | 35 | 0.426 | 0.1685 | 0.97 | 0.92 | 0.99 | Increase |
| 10667 | Metabolite - 2389 | 35 | 0.4367 | 0.172 | 0.94 | 0.94 | 1.01 | Increase |
| 6254 | Metabolite - 1284 | 35 | 0.4709 | 0.1841 | 1.04 | 1.14 | 1.05 | Increase |
| 22133 | DL-hexanoyl-carnitine | 35 | 0.4843 | 0.1879 | 0.97 | 0.98 | 1.05 | Increase |
| 15220 | Metabolite - 3813 | 35 | 0.4935 | 0.1907 | 0.87 | 0.94 | 0.94 | Increase |
| 27728 | glycerol-2-phosphate | 50 | 0.5162 | 0.198 | 0.79 | 0.86 | 0.87 | Increase |
| 10945 | Metabolite - 2560 | 35 | 0.5351 | 0.2037 | 0.98 | 0.96 | 1.00 | Increase |
| 10629 | Metabolite - 2386 | 35 | 0.5582 | 0.2109 | 0.81 | 0.93 | 0.84 | Increase |
| 10492 | Metabolite - 2320 | 35 | 0.5731 | 0.2157 | 0.85 | 0.84 | 0.94 | Increase |
| 14715 | Metabolite - 3653 | 35 | 0.5829 | 0.2186 | 0.99 | 0.94 | 1.18 | Increase |
| 15129 | Metabolite - 1001 | 35 | 0.5888 | 0.22 | 0.71 | 0.78 | 0.82 | Increase |
| 16186 | gamma-glu-gly-leu- | 35 | 0.6239 | 0.2296 | 0.71 | 0.80 | 0.79 | Increase |
| 1898 | proline | 35 | 0.627 | 0.2296 | 1.01 | 1.05 | 1.05 | Increase |
| 1365 | tetradecanoic acid | 50 | 0.6299 | 0.2296 | 1.00 | 1.07 | 1.06 | Increase |
| 1507 | palmitoleic acid | 50 | 0.6301 | 0.2296 | 0.88 | 1.01 | 0.95 | Increase |
| 7002 | Metabolite - 1576 | 35 | 0.6402 | 0.2308 | 0.93 | 0.94 | 0.97 | Increase |
| 6439 | Metabolite - 1350 | 35 | 0.6454 | 0.2318 | 0.54 | 0.53 | 0.65 | Increase |
| 13142 | Metabolite - 3165 | 35 | 0.6695 | 0.2388 | 0.94 | 0.99 | 0.97 | Increase |
| 8300 | Metabolite - 1988 | 35 | 0.7145 | 0.2507 | 0.99 | 1.07 | 1.00 | Increase |
| 12109 | Metabolite - 2853 | 35 | 0.7191 | 0.2509 | 0.63 | 0.66 | 0.70 | Increase |
| 11292 | Metabolite - 2703 | 35 | 0.7719 | 0.2678 | 0.93 | 0.98 | 0.95 | Increase |
| 14639 | Metabolite - 3603 | 35 | 0.7933 | 0.2739 | 0.69 | 0.76 | 0.70 | Increase |
| 10501 | Metabolite - 2321 | 35 | 0.7968 | 0.2739 | 0.94 | 1.00 | 1.03 | Increase |
| 13038 | Metabolite - 3143 | 35 | 0.8101 | 0.2767 | 0.91 | 0.97 | 0.91 | Increase |
| 513 | creatinine | 35 | 0.8586 | 0.289 | 0.97 | 0.97 | 0.98 | Increase |
| 5727 | Metabolite - 1126 | 35 | 0.881 | 0.2946 | 0.74 | 0.79 | 0.77 | Increase |
| 12625 | Metabolite - 3002 | 50 | 0.9626 | 0.3151 | 0.99 | 0.98 | 1.00 | Increase |
| 10551 | Metabolite - 2347 | 35 | 0.964 | 0.3151 | 0.93 | 0.92 | 0.96 | Increase |
| 5652 | Metabolite - 1090 | 35 | 0.9896 | 0.3205 | 0.28 | 0.29 | 0.30 | Increase |
| 13200 | Metabolite - 3180 | 35 | 0.9939 | 0.3207 | 0.82 | 0.82 | 0.82 | Increase |
| 7177 | Metabolite - 1656 | 35 | 2.58E−19 | 4.37E−18 | 1.27 | 0.80 | 0.42 | Decrease |
| 15113 | Metabolite - 3783 | 35 | 1.81E−16 | 2.04E−15 | 1.20 | 0.99 | 0.75 | Decrease |
| 16002 | Metabolite - 3992 | 35 | 7.75E−11 | 2.92E−10 | 1.14 | 0.99 | 0.80 | Decrease |
| 5587 | dehydroepiandrosterone-sulfate- | 35 | 1.40E−09 | 4.19E−09 | 1.38 | 0.97 | 0.59 | Decrease |
| 10252 | Metabolite - 2271 | 35 | 3.96E−09 | 1.12E−08 | 1.31 | 1.01 | 0.74 | Decrease |
| 12763 | Metabolite - 3083 | 50 | 9.48E−09 | 2.60E−08 | 1.09 | 0.83 | 0.64 | Decrease |
| 10156 | Metabolite - 2259 | 35 | 1.73E−07 | 4.19E−07 | 1.30 | 1.15 | 0.68 | Decrease |
| 13545 | Metabolite - 3322 | 35 | 8.43E−07 | 1.82E−06 | 1.14 | 1.02 | 0.54 | Decrease |
| 12768 | Metabolite - 3088 | 50 | 1.29E−06 | 2.73E−06 | 1.05 | 0.86 | 0.71 | Decrease |

TABLE 2-continued

Compounds that change with age.

| COMP ID | COMPOUND | Library | p-value | q-value | 20-35 years | 36-50 years | 51-65 years | Change with age (youngest to oldest) |
|---|---|---|---|---|---|---|---|---|
| 11053 | Metabolite - 2567 | 35 | 3.74E−06 | 7.13E−06 | 1.10 | 1.00 | 0.81 | Decrease |
| 5647 | Metabolite - 1088 | 35 | 1.93E−05 | 3.06E−05 | 1.40 | 0.94 | 0.81 | Decrease |
| 13589 | Metabolite - 3327 | 35 | 1.00E−04 | 1.00E−04 | 0.96 | 1.10 | 0.60 | Decrease |
| 13214 | Metabolite - 3183-possible-gamma-L-glutamyl-L-phenylalanine-or-aspartame | 35 | 4.00E−04 | 5.00E−04 | 1.03 | 0.86 | 0.75 | Decrease |
| 15686 | beta-hydroxypyruvic acid | 35 | 5.00E−04 | 6.00E−04 | 1.08 | 0.99 | 0.91 | Decrease |
| 12666 | Metabolite - 3033 | 50 | 5.00E−04 | 6.00E−04 | 1.07 | 0.93 | 0.87 | Decrease |
| 16506 | Metabolite - 4271 | 50 | 5.00E−04 | 6.00E−04 | 0.84 | 1.07 | 0.62 | Decrease |
| 6421 | Metabolite - 1345 | 35 | 0.001 | 0.0012 | 1.43 | 0.92 | 0.78 | Decrease |
| 16509 | Metabolite - 4273 | 50 | 0.0011 | 0.0012 | 0.78 | 0.49 | 0.49 | Decrease |
| 12726 | Metabolite - 3058 | 50 | 0.0014 | 0.0015 | 1.04 | 0.92 | 0.84 | Decrease |
| 10727 | Metabolite - 2398 | 35 | 0.0016 | 0.0017 | 1.07 | 0.98 | 0.90 | Decrease |
| 2761 | thyroxine | 35 | 0.0022 | 0.0022 | 1.07 | 0.88 | 0.96 | Decrease |
| 16512 | Metabolite - 4275 | 50 | 0.0029 | 0.0028 | 1.08 | 0.78 | 0.79 | Decrease |
| 12663 | Metabolite - 3030 | 50 | 0.0049 | 0.0045 | 1.05 | 0.95 | 0.89 | Decrease |
| 16508 | Metabolite - 4272 | 50 | 0.005 | 0.0046 | 1.03 | 0.96 | 0.87 | Decrease |
| 10438 | gamma-glu-leu | 35 | 0.0055 | 0.0049 | 1.02 | 0.96 | 0.85 | Decrease |
| 6499 | Metabolite - 1376 | 35 | 0.0082 | 0.007 | 0.93 | 0.83 | 0.54 | Decrease |
| 7650 | Metabolite - 1834 | 35 | 0.0086 | 0.0073 | 0.69 | 0.93 | 0.52 | Decrease |
| 6266 | Metabolite - 1286 | 35 | 0.009 | 0.0074 | 1.03 | 0.98 | 0.93 | Decrease |
| 12645 | Metabolite - 3017 | 50 | 0.01 | 0.008 | 1.09 | 0.95 | 0.87 | Decrease |
| 12757 | Metabolite - 3078 | 50 | 0.011 | 0.0088 | 1.03 | 0.73 | 0.76 | Decrease |
| 12639 | Metabolite - 3012 | 50 | 0.0187 | 0.0139 | 1.05 | 0.94 | 0.91 | Decrease |
| 13487 | Metabolite - 3310-probable-cotinine | 35 | 0.0236 | 0.0168 | 0.34 | 0.58 | 0.33 | Decrease |
| 6374 | Metabolite - 1327 | 35 | 0.0243 | 0.017 | 1.30 | 0.83 | 0.81 | Decrease |
| 6108 | Metabolite - 1202 | 35 | 0.0363 | 0.0237 | 0.79 | 0.94 | 0.53 | Decrease |
| 12609 | Metabolite - 2986 | 50 | 0.0384 | 0.0245 | 1.02 | 0.97 | 0.92 | Decrease |
| 12601 | Metabolite - 2978 | 50 | 0.0419 | 0.0263 | 1.04 | 0.86 | 0.79 | Decrease |
| 6137 | Metabolite - 1212 | 35 | 0.0457 | 0.0284 | 1.09 | 0.84 | 0.68 | Decrease |
| 16229 | Isobar-2: arabitol/adonitol/xylitol | 35 | 0.0481 | 0.0296 | 1.02 | 1.07 | 0.80 | Decrease |
| 5765 | Metabolite - 1142 | 35 | 0.0594 | 0.0357 | 0.89 | 1.09 | 0.84 | Decrease |
| 2129 | oxitryptan | 35 | 0.0605 | 0.0359 | 0.98 | 0.87 | 0.81 | Decrease |
| 12647 | Metabolite - 3019 | 50 | 0.062 | 0.0362 | 1.02 | 0.96 | 0.92 | Decrease |
| 15609 | Metabolite - 3969 | 35 | 0.0646 | 0.0375 | 1.01 | 1.03 | 0.94 | Decrease |
| 15365 | sn-Glycerol-3-phosphate | 50 | 0.0664 | 0.0381 | 0.96 | 1.12 | 0.93 | Decrease |
| 2730 | gamma-L-glutamyl-L-glutamine | 35 | 0.0671 | 0.0381 | 0.84 | 0.76 | 0.66 | Decrease |
| 12670 | Metabolite - 3037 | 50 | 0.07 | 0.0393 | 0.97 | 1.14 | 0.95 | Decrease |
| 10700 | Metabolite - 2393 | 35 | 0.0721 | 0.0403 | 1.03 | 0.99 | 0.93 | Decrease |
| 6579 | Metabolite - 1398- | 35 | 0.08 | 0.044 | 1.08 | 1.03 | 0.96 | Decrease |
| 12658 | Metabolite - 3026 | 50 | 0.1006 | 0.0524 | 1.00 | 0.93 | 0.90 | Decrease |
| 584 | mannose | 50 | 0.104 | 0.0535 | 1.02 | 1.06 | 0.91 | Decrease |
| 10148 | Metabolite - 2257 | 35 | 0.1067 | 0.0542 | 1.05 | 0.74 | 0.71 | Decrease |
| 12074 | glucose | 50 | 0.1234 | 0.0621 | 0.96 | 0.82 | 0.86 | Decrease |
| 12912 | Metabolite - 3129 | 35 | 0.1245 | 0.0623 | 0.98 | 0.92 | 0.85 | Decrease |
| 13104 | Metabolite - 3160 | 35 | 0.1359 | 0.0671 | 0.97 | 1.00 | 0.91 | Decrease |
| 12650 | Metabolite - 3022 | 50 | 0.148 | 0.0721 | 1.08 | 1.03 | 0.97 | Decrease |
| 6852 | Metabolite - 1498 | 35 | 0.1547 | 0.0745 | 0.95 | 0.87 | 0.78 | Decrease |
| 10047 | Metabolite - 2237 | 35 | 0.1773 | 0.0839 | 0.59 | 0.72 | 0.41 | Decrease |
| 10145 | Metabolite - 2256 | 35 | 0.2033 | 0.0927 | 0.57 | 0.66 | 0.44 | Decrease |
| 7096 | Metabolite - 1612 | 35 | 0.2067 | 0.0938 | 0.89 | 0.76 | 0.74 | Decrease |
| 2734 | gamma-L-glutamyl-L-tyrosine | 35 | 0.2086 | 0.0939 | 0.90 | 0.83 | 0.77 | Decrease |
| 10544 | Metabolite - 2329 | 35 | 0.2172 | 0.0969 | 0.92 | 0.70 | 0.64 | Decrease |
| 10655 | Metabolite - 2388 | 35 | 0.2283 | 0.1 | 0.93 | 0.86 | 0.85 | Decrease |
| 12771 | Metabolite - 3091 | 50 | 0.2439 | 0.1064 | 0.89 | 0.96 | 0.80 | Decrease |
| 12756 | Metabolite - 3077 | 50 | 0.2853 | 0.1219 | 1.01 | 0.99 | 0.94 | Decrease |
| 20675 | 1,5-anhydro-D-glucitol | 50 | 0.2903 | 0.1235 | 0.90 | 0.93 | 0.81 | Decrease |
| 15626 | Metabolite - 3977 | 35 | 0.302 | 0.1274 | 1.03 | 1.04 | 0.96 | Decrease |
| 12780 | Metabolite - 3098 | 50 | 0.3295 | 0.1362 | 0.89 | 0.81 | 0.73 | Decrease |
| 12656 | Metabolite - 3025 | 50 | 0.3608 | 0.1485 | 1.00 | 0.99 | 0.94 | Decrease |
| 9905 | Metabolite - 2231 | 35 | 0.3841 | 0.1562 | 0.83 | 0.76 | 0.77 | Decrease |
| 10604 | Metabolite - 2370 | 35 | 0.4185 | 0.1675 | 0.98 | 1.07 | 0.95 | Decrease |
| 1564 | citric acid | 35 | 0.4593 | 0.1803 | 1.13 | 1.01 | 1.09 | Decrease |
| 10476 | Metabolite - 2316 | 35 | 0.4842 | 0.1879 | 0.84 | 0.98 | 0.83 | Decrease |
| 27738 | threonic acid | 50 | 0.5085 | 0.1958 | 0.97 | 0.85 | 0.90 | Decrease |
| 10378 | Metabolite - 2287 | 35 | 0.5284 | 0.2019 | 0.66 | 0.55 | 0.62 | Decrease |
| 10143 | Metabolite - 2255 | 35 | 0.5426 | 0.2058 | 0.69 | 0.85 | 0.65 | Decrease |

TABLE 2-continued

Compounds that change with age.

| COMP ID | COMPOUND | Library | p-value | q-value | 20-35 years | 36-50 years | 51-65 years | Change with age (youngest to oldest) |
|---|---|---|---|---|---|---|---|---|
| 8796 | Metabolite - 2074 | 35 | 0.597 | 0.2223 | 0.64 | 0.77 | 0.64 | Decrease |
| 1366 | trans-4-hydroxyproline | 35 | 0.6026 | 0.2236 | 0.59 | 0.63 | 0.54 | Decrease |
| 10825 | Metabolite - 2546 | 35 | 0.6117 | 0.2261 | 1.01 | 0.91 | 1.01 | Decrease |
| 9748 | Metabolite - 2212 | 35 | 0.6327 | 0.2297 | 0.94 | 1.01 | 0.94 | Decrease |
| 16037 | Metabolite - 4003 | 35 | 0.6375 | 0.2306 | 0.63 | 0.55 | 0.61 | Decrease |
| 5618 | Metabolite - 1085 | 35 | 0.6565 | 0.235 | 0.99 | 1.00 | 0.95 | Decrease |
| 14753 | Metabolite - 3663 | 35 | 0.6744 | 0.2397 | 0.67 | 0.68 | 0.62 | Decrease |
| 15612 | Metabolite - 3972 | 35 | 0.709 | 0.2507 | 0.81 | 0.76 | 0.77 | Decrease |
| 5628 | Metabolite - 1086 | 35 | 0.7103 | 0.2507 | 0.86 | 0.94 | 0.84 | Decrease |
| 14759 | Metabolite - 3667 | 35 | 0.7151 | 0.2507 | 0.58 | 0.62 | 0.54 | Decrease |
| 6270 | Metabolite - 1288 | 35 | 0.7207 | 0.2509 | 0.80 | 0.82 | 0.74 | Decrease |
| 11604 | Metabolite - 2774 | 35 | 0.7976 | 0.2739 | 0.92 | 0.85 | 0.88 | Decrease |
| 1572 | glyceric acid | 50 | 0.8112 | 0.2767 | 1.04 | 0.99 | 1.02 | Decrease |
| 13372 | Metabolite - 3249 | 35 | 0.8153 | 0.2772 | 0.99 | 0.97 | 0.97 | Decrease |
| 6278 | Metabolite - 1289 | 35 | 0.827 | 0.2802 | 0.82 | 0.76 | 0.79 | Decrease |
| 12099 | Metabolite - 2850 | 35 | 0.8505 | 0.2872 | 0.86 | 0.83 | 0.81 | Decrease |
| 12533 | Metabolite - 2915 | 50 | 0.868 | 0.2912 | 1.00 | 1.01 | 0.99 | Decrease |
| 2137 | biliverdin | 35 | 0.8905 | 0.2968 | 1.07 | 1.06 | 1.02 | Decrease |
| 1480 | Metabolite - 1005 | 35 | 0.9189 | 0.3053 | 0.49 | 0.46 | 0.47 | Decrease |
| 12673 | Metabolite - 3040 | 50 | 0.9401 | 0.3113 | 0.99 | 0.96 | 0.96 | Decrease |
| 14840 | Metabolite - 3708 | 35 | 0.9492 | 0.3133 | 0.96 | 0.96 | 0.94 | Decrease |
| 5670 | Metabolite - 1105 | 35 | 0.9547 | 0.3141 | 0.81 | 0.82 | 0.77 | Decrease |
| 1302 | methionine | 35 | 0.9834 | 0.3204 | 1.01 | 1.00 | 1.00 | Decrease |
| 577 | fructose | 50 | 0.9899 | 0.3205 | 0.63 | 0.62 | 0.62 | Decrease |
| 13775 | Metabolite - 3370 | 35 | 0.9974 | 0.3209 | 0.93 | 0.93 | 0.92 | Decrease |

Table 3 contains a list of the biochemical pathways that showed differences either by age, gender or race based upon the changes in metabolites that comprise the pathway.

TABLE 3

Numbers of biomarker compounds showing statistically significant differences per biochemical pathway by age, race and gender.

| Pathway | Age | Race | Gender |
|---|---|---|---|
| Arginine and proline metabolism | 11 | 5 | 2 |
| ABC transporters | 12 | 2 | 1 |
| Urea cycle and metabolism of amino groups | 8 | 5 | 1 |
| Aminoacyl-tRNA biosynthesis | 8 | 2 | |
| Purine metabolism | 5 | 3 | 2 |
| Alanine and aspartate metabolism | 6 | | 2 |
| Lysine degradation | 5 | 2 | 1 |
| Pyrimidine metabolism | 7 | 1 | |
| Citrate cycle (TCA cycle) | 4 | | 3 |
| Glycine, serine and threonine metabolism | 6 | 1 | |
| Neuroactive ligand-receptor interaction | 5 | 1 | 1 |
| beta-Alanine metabolism | 6 | | |
| Histidine metabolism | 4 | 1 | 1 |
| Tryptophan metabolism | 5 | 1 | |
| Tyrosine metabolism | 5 | | 1 |
| Valine, leucine and isoleucine degradation | 4 | | 2 |
| Glutamate metabolism | 4 | | 1 |
| Porphyrin and chlorophyll metabolism | 3 | 1 | 1 |
| Carbon fixation | 3 | 1 | |

Age Associated Changes

The majority of compounds that were different between the age groups showed an increase with age. Compounds with levels that showed significant differences with age are shown in Table 2. One interesting observation in this table is the large number of amino acids that increase with age. In a study of pediatric subjects published by Lepage and coworkers, it was shown that amino acid levels increase steadily after the first year of life (Lepage, N., et al., 1997, Clin Chem. 43(12):2397-402). Although this study only monitored subjects until age 18, its trend is consistent with the data in our study. Also, we frequently see that amino acid levels within subjects are highly correlated. In FIG. 1, one can see that leucine and valine levels are highly correlated.

Several compounds show statistically significant changes in level but no clear upward or downward trend with age (Table 2). Fourteen compounds show highest abundance in subjects aged 36-50. Thirteen compounds with this pattern are unnamed. These are Metabolite—4271, Metabolite—1129, Metabolite—2894, Metabolite—1834, Metabolite—3310, Metabolite—2810, Metabolite—1142, Metabolite—3018, Metabolite—1183, Metabolite—3487, Metabolite—1262, Metabolite—1264, Metabolite—1187, and Metabolite—1718. The only named compound in this group is glycerol-3-phosphate. Four compounds are lowest in the middle age group with two unnamed compounds (Metabolite—2558, Metabolite—3830) and two named compounds. The named compounds are trans-2-3-4-trimethoxycinnamic acid and tryptophan.

A search of the literature and the Geigy Tables (*Physical Chemistry, Composition of Blood, Hematology, Somatometric Data*, 8 ed., 1984, Geigy Scientific Tables, ed. C. Lentner. Vol. 3, Ciba-Geigy Ltd., Basle, Switzerland) was carried out to determine if the changes in levels of the 75 named metabolites that were measured in this study are consistent with previous reports. The Geigy Tables were a useful source of information, with plasma levels of 32 of the 75 compounds listed. The trends for 23 of the 32 reported compounds were in agreement with the Geigy Tables; however, five of 32 showed differing trends. Some of this disparity is due to the fact that not all of the reports were broken out by the same age categories used in our demographic study. If ages were reported, most of the age groups were in the broad categories of newborn, children, adults.

Literature searches were less informative in terms of age-related changes in the levels of these metabolites. While many of the compounds were studied in the literature, often, the changes with age were not reported, although many compounds were associated with age-related diseases such as Alzheimer's Disease (AD). One exception is unknown metabolite 1069 which is listed as a possible DHEA-S, a major secretory product of the human adrenal gland. This compound has been reported to gradually decrease with age (Birkenhager-Gillesse, E. G., J. Derksen, and A. M. Lagaay, 1994, Ann. NY Acad Sci, 719(1):543-552). Interestingly, this compound is shown to be increased in AD relative to control subjects. However, the report stated that a significant correlation between DHEAS levels and AD was not observed.

Results and Discussion

In this example it was demonstrated that metabolic profiles change with age. Thus, characteristic metabolic profiles related to the biochemical or physiological age ("Metabolic Age" or MetaboAge) can be determined using metabolomics.

Gender-Associated Changes

Table 4 sets forth the metabolites that showed different levels between male and female individuals.

TABLE 4

Compounds that vary based on gender.

Metabolites higher in females than males

| COMP ID | COMPOUND | Library | p-value | q-value | FEMALE | MALE | Female/Male |
|---|---|---|---|---|---|---|---|
| 11438 | phosphate | 50 | 7.00E−04 | 0.0048 | 1.02 | 0.93 | 1.10 |
| 1507 | palmitoleic acid | 50 | 0.0015 | 0.0092 | 1.13 | 0.79 | 1.42 |
| 15122 | glycerol | 50 | 0.0016 | 0.0092 | 1.13 | 0.96 | 1.18 |
| 6108 | Metabolite - 1202 | 35 | 0.0017 | 0.0092 | 0.98 | 0.55 | 1.79 |
| 10424 | Metabolite - 2292 | 35 | 0.0021 | 0.0096 | 0.79 | 0.52 | 1.52 |
| 15328 | azelaic acid | 35 | 0.0026 | 0.0115 | 1.07 | 0.95 | 1.12 |
| 12609 | Metabolite - 2986 | 50 | 0.0027 | 0.0117 | 1.02 | 0.92 | 1.11 |
| 12912 | Metabolite - 3129 | 35 | 0.0035 | 0.0139 | 1.00 | 0.84 | 1.19 |
| 15626 | Metabolite - 3977 | 35 | 0.0043 | 0.0156 | 1.08 | 0.94 | 1.14 |
| 27718 | creatine | 35 | 0.0047 | 0.0164 | 1.10 | 0.90 | 1.22 |
| 16002 | Metabolite - 3992 | 35 | 0.005 | 0.017 | 1.03 | 0.91 | 1.13 |
| 12774 | Metabolite - 3094 | 50 | 0.0059 | 0.0198 | 1.04 | 0.93 | 1.12 |
| 12759 | Metabolite - 3080 | 50 | 0.0072 | 0.0229 | 1.12 | 0.98 | 1.14 |
| 11111 | Metabolite - 2592 | 35 | 0.0146 | 0.038 | 1.28 | 0.90 | 1.41 |
| 7650 | Metabolite - 1834 | 35 | 0.0207 | 0.0494 | 0.83 | 0.58 | 1.42 |
| 10667 | Metabolite - 2389 | 35 | 0.0219 | 0.0507 | 1.02 | 0.91 | 1.12 |
| 6278 | Metabolite - 1289 | 35 | 0.0247 | 0.0565 | 0.88 | 0.71 | 1.24 |
| 13372 | Metabolite - 3249 | 35 | 0.031 | 0.0677 | 1.01 | 0.94 | 1.07 |
| 16518 | Metabolite - 4276 | 50 | 0.0319 | 0.0687 | 0.96 | 0.80 | 1.20 |
| 6852 | Metabolite - 1498 | 35 | 0.0332 | 0.0705 | 0.94 | 0.79 | 1.19 |
| 1365 | tetradecanoic acid | 50 | 0.0537 | 0.0987 | 1.10 | 0.99 | 1.12 |
| 542 | 3-hydroxybutanoic acid | 50 | 0.0542 | 0.0987 | 1.40 | 1.06 | 1.31 |
| 15612 | Metabolite - 3972 | 35 | 0.0565 | 0.1011 | 0.83 | 0.73 | 1.14 |
| 10047 | Metabolite - 2237 | 35 | 0.0573 | 0.1011 | 0.71 | 0.44 | 1.59 |
| 10154 | Metabolite - 2258- | 35 | 0.0649 | 0.1068 | 1.02 | 0.88 | 1.15 |
| 13487 | Metabolite - 3310-probable-cotinine | 35 | 0.0758 | 0.1184 | 0.47 | 0.34 | 1.39 |
| 11292 | Metabolite - 2703 | 35 | 0.0781 | 0.1207 | 1.00 | 0.91 | 1.09 |
| 16508 | Metabolite - 4272 | 50 | 0.0881 | 0.1334 | 0.99 | 0.92 | 1.08 |
| 1561 | alpha-tocopherol | 50 | 0.093 | 0.1369 | 1.04 | 0.94 | 1.11 |
| 1359 | oleic acid | 50 | 0.0956 | 0.1394 | 1.05 | 0.92 | 1.14 |
| 11604 | Metabolite - 2774 | 35 | 0.1023 | 0.1442 | 0.95 | 0.82 | 1.17 |
| 12781 | Metabolite - 3099 | 50 | 0.1435 | 0.1815 | 1.06 | 0.95 | 1.12 |
| 6137 | Metabolite - 1212 | 35 | 0.1578 | 0.1916 | 0.95 | 0.76 | 1.25 |
| 5618 | Metabolite - 1085 | 35 | 0.1646 | 0.1968 | 1.01 | 0.95 | 1.07 |
| 7424 | Metabolite - 1718 | 35 | 0.176 | 0.204 | 0.47 | 0.33 | 1.41 |
| 14639 | Metabolite - 3603 | 35 | 0.1875 | 0.2126 | 0.78 | 0.67 | 1.17 |
| 1336 | n-hexadecanoic acid | 50 | 0.1938 | 0.2152 | 1.08 | 1.01 | 1.06 |
| 2761 | thyroxine | 35 | 0.1979 | 0.2179 | 1.00 | 0.94 | 1.06 |
| 1105 | linoleic acid | 50 | 0.2016 | 0.2203 | 1.05 | 0.99 | 1.07 |
| 15529 | Metabolite - 3951 | 35 | 0.2111 | 0.2266 | 1.03 | 0.99 | 1.05 |
| 6215 | Metabolite - 1261 | 35 | 0.2115 | 0.2266 | 0.80 | 0.64 | 1.24 |
| 6204 | Metabolite - 1252 | 35 | 0.2117 | 0.2266 | 0.55 | 0.43 | 1.27 |
| 10700 | Metabolite - 2393 | 35 | 0.2198 | 0.2336 | 1.01 | 0.96 | 1.05 |
| 12785 | Metabolite - 3103 | 50 | 0.2306 | 0.2401 | 0.53 | 0.38 | 1.37 |
| 12074 | glucose | 50 | 0.2376 | 0.2431 | 0.91 | 0.84 | 1.08 |
| 6787 | Metabolite - 1465 | 35 | 0.2383 | 0.2431 | 1.01 | 0.95 | 1.06 |
| 584 | mannose | 50 | 0.2428 | 0.246 | 1.03 | 0.96 | 1.07 |
| 12783 | Metabolite - 3101 | 50 | 0.2445 | 0.2462 | 1.00 | 0.95 | 1.06 |
| 63 | cholesterol | 50 | 0.2745 | 0.2621 | 1.04 | 0.95 | 1.09 |
| 6254 | Metabolite - 1284 | 35 | 0.2789 | 0.2621 | 1.11 | 1.04 | 1.07 |
| 12663 | Metabolite - 3030 | 50 | 0.2792 | 0.2621 | 0.98 | 0.94 | 1.05 |
| 15129 | Metabolite - 1001 | 35 | 0.3014 | 0.2761 | 0.82 | 0.72 | 1.13 |
| 12673 | Metabolite - 3040 | 50 | 0.3051 | 0.2779 | 1.01 | 0.94 | 1.08 |

TABLE 4-continued

Compounds that vary based on gender.

| | | | | | | |
|---|---|---|---|---|---|---|
| 22133 | DL-hexanoyl-carnitine | 35 | 0.3075 | 0.2783 | 1.03 | 0.97 | 1.06 |
| 6266 | Metabolite - 1286 | 35 | 0.3092 | 0.2783 | 0.99 | 0.97 | 1.03 |
| 5724 | Metabolite - 1125 | 35 | 0.3226 | 0.2837 | 0.66 | 0.58 | 1.13 |
| 6439 | Metabolite - 1350 | 35 | 0.3301 | 0.2876 | 0.63 | 0.52 | 1.21 |
| 5800 | Metabolite - 1188 | 35 | 0.3501 | 0.2993 | 0.60 | 0.50 | 1.20 |
| 7177 | Metabolite - 1656 | 35 | 0.3681 | 0.3097 | 0.78 | 0.72 | 1.09 |
| 16138 | Metabolite - 4080 | 50 | 0.3899 | 0.3218 | 0.99 | 0.93 | 1.06 |
| 6296 | Metabolite - 1303-SHAXQXNNR | 35 | 0.4569 | 0.3549 | 0.65 | 0.57 | 1.12 |
| 12771 | Metabolite - 3091 | 50 | 0.462 | 0.357 | 0.91 | 0.85 | 1.07 |
| 12777 | Metabolite - 3097 | 50 | 0.4828 | 0.3639 | 1.05 | 0.99 | 1.06 |
| 12352 | Metabolite - 2871 | 35 | 0.4906 | 0.3644 | 0.89 | 0.83 | 1.06 |
| 10782 | Metabolite - 2486 | 35 | 0.4971 | 0.3675 | 1.01 | 0.95 | 1.06 |
| 569 | caffeine | 35 | 0.5074 | 0.3697 | 0.65 | 0.57 | 1.15 |
| 5609 | Metabolite - 1083 | 35 | 0.5081 | 0.3697 | 0.20 | 0.16 | 1.25 |
| 10304 | Metabolite - 2276 | 35 | 0.5179 | 0.3721 | 0.84 | 0.76 | 1.10 |
| 1121 | heptadecanoic acid | 50 | 0.5243 | 0.3723 | 1.00 | 0.97 | 1.03 |
| 14753 | Metabolite - 3663 | 35 | 0.5399 | 0.3789 | 0.67 | 0.63 | 1.06 |
| 9561 | Metabolite - 2193 | 35 | 0.5461 | 0.3816 | 0.66 | 0.59 | 1.12 |
| 13605 | Metabolite - 4868 | 35 | 0.5922 | 0.4042 | 0.66 | 0.59 | 1.11 |
| 6239 | Metabolite - 1264 | 35 | 0.5946 | 0.4042 | 0.67 | 0.60 | 1.12 |
| 1584 | Metabolite - 1003 | 35 | 0.5985 | 0.4042 | 0.92 | 0.90 | 1.03 |
| 10309 | Metabolite - 2277 | 35 | 0.6028 | 0.4042 | 0.83 | 0.78 | 1.06 |
| 15686 | beta-hydroxypyruvic acid | 35 | 0.6034 | 0.4042 | 1.00 | 0.98 | 1.02 |
| 6236 | Metabolite - 1983 | 35 | 0.6161 | 0.4066 | 0.56 | 0.51 | 1.09 |
| 1110 | arachidonic acid | 50 | 0.6196 | 0.4069 | 0.98 | 0.96 | 1.02 |
| 10655 | Metabolite - 2388 | 35 | 0.6335 | 0.4092 | 0.89 | 0.87 | 1.02 |
| 5803 | Metabolite - 1190 | 35 | 0.6417 | 0.4126 | 0.68 | 0.64 | 1.07 |
| 18254 | paraxanthine | 35 | 0.6485 | 0.4152 | 0.59 | 0.54 | 1.08 |
| 14755 | Metabolite - 3664 | 35 | 0.6626 | 0.4162 | 0.79 | 0.75 | 1.05 |
| 14759 | Metabolite - 3667 | 35 | 0.6643 | 0.4162 | 0.60 | 0.57 | 1.06 |
| 9905 | Metabolite - 2231 | 35 | 0.6705 | 0.4162 | 0.79 | 0.77 | 1.03 |
| 15596 | Metabolite - 3962 | 35 | 0.6735 | 0.4162 | 1.12 | 1.10 | 1.02 |
| 8796 | Metabolite - 2074 | 35 | 0.6875 | 0.4191 | 0.70 | 0.65 | 1.07 |
| 1366 | trans-4-hydroxyproline | 35 | 0.6967 | 0.42 | 0.60 | 0.57 | 1.05 |
| 16186 | gamma-glu-gly-leu- | 35 | 0.7018 | 0.42 | 0.78 | 0.75 | 1.04 |
| 10727 | Metabolite - 2398 | 35 | 0.7114 | 0.4216 | 0.99 | 0.97 | 1.02 |
| 1572 | glyceric acid | 50 | 0.7366 | 0.4251 | 1.03 | 1.01 | 1.02 |
| 10570 | Metabolite - 2366 | 35 | 0.7453 | 0.4251 | 0.96 | 0.93 | 1.03 |
| 16512 | Metabolite - 4275 | 50 | 0.7453 | 0.4251 | 0.88 | 0.86 | 1.03 |
| 10945 | Metabolite - 2560 | 35 | 0.7624 | 0.4251 | 0.99 | 0.98 | 1.01 |
| 13296 | Metabolite - 3230 | 35 | 0.7664 | 0.4251 | 1.04 | 1.03 | 1.01 |
| 27738 | threonic acid | 50 | 0.7737 | 0.4251 | 0.92 | 0.89 | 1.03 |
| 12601 | Metabolite - 2978 | 50 | 0.7757 | 0.4251 | 0.90 | 0.88 | 1.03 |
| 16509 | Metabolite - 4273 | 50 | 0.7813 | 0.4251 | 0.58 | 0.56 | 1.03 |
| 12669 | Metabolite - 3036 | 50 | 0.7834 | 0.4251 | 0.84 | 0.82 | 1.02 |
| 12533 | Metabolite - 2915 | 50 | 0.8191 | 0.4339 | 1.00 | 0.99 | 1.01 |
| 10145 | Metabolite - 2256 | 35 | 0.8194 | 0.4339 | 0.56 | 0.54 | 1.04 |
| 10774 | Metabolite - 2466 | 35 | 0.8418 | 0.4437 | 0.64 | 0.61 | 1.04 |
| 10414 | Metabolite - 2291 | 35 | 0.8463 | 0.4437 | 0.71 | 0.69 | 1.03 |
| 6499 | Metabolite - 1376 | 35 | 0.8573 | 0.4452 | 0.76 | 0.74 | 1.03 |
| 15113 | Metabolite - 3783 | 35 | 0.8583 | 0.4452 | 0.97 | 0.96 | 1.01 |
| 12757 | Metabolite - 3078 | 50 | 0.87 | 0.4466 | 0.84 | 0.82 | 1.02 |
| 1358 | octadecanoic acid | 50 | 0.871 | 0.4466 | 1.02 | 1.01 | 1.01 |
| 21044 | 2-hydroxybutyric acid | 50 | 0.8821 | 0.4477 | 1.02 | 1.01 | 1.01 |
| 6112 | Metabolite - 1203-HXGXA | 35 | 0.8844 | 0.4477 | 0.53 | 0.51 | 1.04 |
| 10715 | Metabolite - 2395 | 35 | 0.9178 | 0.4555 | 0.90 | 0.88 | 1.01 |
| 10629 | Metabolite - 2386 | 35 | 0.9198 | 0.4555 | 0.86 | 0.86 | 1.01 |
| 12710 | Metabolite - 3052 | 35 | 0.9199 | 0.4555 | 0.95 | 0.95 | 1.01 |
| 5798 | Metabolite - 1187 | 35 | 0.9388 | 0.4634 | 0.46 | 0.45 | 1.02 |
| 6136 | Metabolite - 1211-IHWESASLLR | 35 | 0.964 | 0.4721 | 0.66 | 0.66 | 1.01 |
| 5577 | Metabolite - 1065 | 35 | 0.9931 | 0.4809 | 0.96 | 0.96 | 1.00 |

TABLE 4-continued

Compounds that vary based on gender.

Metabolites higher in males than females

| COMP ID | COMPOUND | LIB_ID | pvalue | qvalue | FEMALE | MALE | Female/Male |
|---|---|---|---|---|---|---|---|
| 10252 | Metabolite - 2271 | 35 | 2.06E−18 | 3.15E−16 | 0.70 | 1.40 | 0.50 |
| 513 | creatinine | 35 | 3.80E−17 | 2.91E−15 | 0.86 | 1.10 | 0.79 |
| 10825 | Metabolite - 2546 | 35 | 1.68E−15 | 8.57E−14 | 0.66 | 1.44 | 0.46 |
| 15683 | 4-methyl-2-oxopentanoate | 50 | 1.14E−08 | 3.70E−07 | 0.87 | 1.15 | 0.76 |
| 5647 | Metabolite - 1088 | 35 | 1.21E−08 | 3.70E−07 | 0.76 | 1.37 | 0.56 |
| 15278 | Metabolite - 3843 | 35 | 2.31E−08 | 5.89E−07 | 0.85 | 1.09 | 0.77 |
| 1604 | uric acid | 35 | 4.27E−07 | 9.33E−06 | 0.95 | 1.04 | 0.92 |
| 15681 | 4-Guanidinobutanoic acid | 35 | 2.42E−06 | 4.63E−05 | 0.93 | 1.08 | 0.87 |
| 6421 | Metabolite - 1345 | 35 | 3.29E−06 | 1.00E−04 | 0.73 | 1.40 | 0.52 |
| 7644 | Metabolite - 1831 | 35 | 3.37E−06 | 1.00E−04 | 0.81 | 1.08 | 0.75 |
| 5587 | dehydroepiandrosterone-sulfate- | 35 | 1.46E−05 | 2.00E−04 | 0.73 | 1.17 | 0.62 |
| 12626 | Metabolite - 3003 | 50 | 3.09E−05 | 4.00E−04 | 0.95 | 1.08 | 0.88 |
| 13038 | Metabolite - 3143 | 35 | 3.82E−05 | 4.00E−04 | 0.77 | 1.13 | 0.68 |
| 54 | tryptophan | 35 | 4.06E−05 | 4.00E−04 | 0.94 | 1.05 | 0.90 |
| 1302 | methionine | 35 | 1.00E−04 | 0.0011 | 0.94 | 1.07 | 0.87 |
| 16055 | Metabolite - 4012 | 50 | 1.00E−04 | 0.0012 | 0.84 | 1.05 | 0.80 |
| 9130 | Metabolite - 2139 | 35 | 1.00E−04 | 0.0013 | 0.92 | 1.13 | 0.82 |
| 10347 | Metabolite - 2285 | 35 | 2.00E−04 | 0.0013 | 0.73 | 1.05 | 0.70 |
| 9491 | Metabolite - 2185 | 35 | 2.00E−04 | 0.0015 | 0.86 | 1.12 | 0.77 |
| 2137 | biliverdin | 35 | 5.00E−04 | 0.0037 | 0.91 | 1.21 | 0.76 |
| 10378 | Metabolite - 2287 | 35 | 8.00E−04 | 0.0059 | 0.48 | 0.76 | 0.63 |
| 12726 | Metabolite - 3058 | 50 | 0.0011 | 0.0073 | 0.86 | 1.00 | 0.85 |
| 10921 | Metabolite - 2558 | 35 | 0.0013 | 0.0083 | 0.22 | 0.49 | 0.46 |
| 6398 | Metabolite - 1335 | 35 | 0.0016 | 0.0092 | 0.87 | 1.12 | 0.77 |
| 16070 | Metabolite - 4019 | 50 | 0.0017 | 0.0092 | 0.90 | 1.03 | 0.87 |
| 16067 | Metabolite - 4017 | 50 | 0.0019 | 0.0096 | 0.91 | 1.05 | 0.87 |
| 1303 | malic acid | 50 | 0.002 | 0.0096 | 0.95 | 1.16 | 0.81 |
| 12924 | Metabolite - 3131 | 35 | 0.0021 | 0.0096 | 0.86 | 1.11 | 0.77 |
| 27741 | cis/trans-aconitic acid | 35 | 0.0029 | 0.0123 | 0.98 | 1.22 | 0.81 |
| 5733 | Metabolite - 1127 | 35 | 0.003 | 0.0126 | 0.88 | 1.05 | 0.84 |
| 3147 | xanthine | 35 | 0.0035 | 0.0139 | 0.71 | 0.95 | 0.75 |
| 6374 | Metabolite - 1327 | 35 | 0.004 | 0.0151 | 0.76 | 1.20 | 0.63 |
| 16332 | Metabolite - 4164 | 35 | 0.0041 | 0.0154 | 0.92 | 1.03 | 0.90 |
| 606 | uridine | 35 | 0.0044 | 0.0156 | 0.94 | 1.08 | 0.87 |
| 10148 | Metabolite - 2257 | 35 | 0.0065 | 0.0211 | 0.65 | 1.03 | 0.64 |
| 6424 | Metabolite - 1346 | 35 | 0.0094 | 0.0293 | 0.96 | 1.04 | 0.92 |
| 1564 | citric acid | 35 | 0.0106 | 0.0323 | 0.98 | 1.18 | 0.83 |
| 18349 | DL-indole-3-lactic acid | 35 | 0.0111 | 0.0329 | 0.90 | 1.04 | 0.86 |
| 528 | alpha-keto-glutarate | 35 | 0.0113 | 0.0329 | 0.76 | 1.02 | 0.74 |
| 5670 | Metabolite - 1105 | 35 | 0.0114 | 0.0329 | 0.63 | 1.01 | 0.63 |
| 1444 | Isobar-56: DL-pipecolic acid/1-amino-cyclopentanecarboxylic acid | 35 | 0.0121 | 0.0344 | 1.06 | 1.26 | 0.84 |
| 64 | phenylalanine | 35 | 0.0128 | 0.0356 | 0.97 | 1.04 | 0.93 |
| 3127 | hypoxanthine | 35 | 0.0134 | 0.0365 | 0.62 | 0.97 | 0.64 |
| 1113 | isocitrate | 35 | 0.0137 | 0.0365 | 0.90 | 1.10 | 0.82 |
| 5689 | Metabolite - 1111 | 35 | 0.0138 | 0.0365 | 0.95 | 1.06 | 0.89 |
| 13257 | Metabolite - 3218 | 35 | 0.0162 | 0.0414 | 0.94 | 1.02 | 0.92 |
| 1431 | p-hydroxyphenyllactic acid | 35 | 0.0175 | 0.0439 | 0.80 | 0.94 | 0.86 |
| 8300 | Metabolite - 1988 | 35 | 0.0178 | 0.0439 | 0.93 | 1.12 | 0.83 |
| 12656 | Metabolite - 3025 | 50 | 0.0188 | 0.0456 | 0.93 | 1.02 | 0.92 |
| 57 | glutamic acid | 50 | 0.0212 | 0.0498 | 0.85 | 1.06 | 0.80 |
| 1494 | 5-oxoproline | 50 | 0.0271 | 0.0609 | 0.96 | 1.06 | 0.90 |
| 8091 | glycocholic acid | 35 | 0.0304 | 0.0674 | 0.71 | 0.98 | 0.72 |
| 15769 | carnitine | 35 | 0.034 | 0.0712 | 0.93 | 1.01 | 0.92 |
| 15663 | Metabolite - 1000 | 35 | 0.0346 | 0.0716 | 0.73 | 0.93 | 0.78 |
| 12791 | Metabolite - 3109 | 50 | 0.0358 | 0.073 | 0.84 | 0.99 | 0.84 |
| 10672 | Metabolite - 2390 | 35 | 0.0368 | 0.0742 | 0.92 | 1.05 | 0.88 |
| 13104 | Metabolite - 3160 | 35 | 0.0386 | 0.0766 | 0.92 | 1.00 | 0.93 |
| 1480 | Metabolite - 1005 | 35 | 0.0391 | 0.0767 | 0.41 | 0.55 | 0.75 |
| 11222 | Metabolite - 2688 | 35 | 0.0407 | 0.0788 | 0.68 | 0.85 | 0.81 |

TABLE 4-continued

Compounds that vary based on gender.

| | | | | | | | |
|---|---|---|---|---|---|---|---|
| 16037 | Metabolite - 4003 | 35 | 0.0455 | 0.0871 | 0.53 | 0.67 | 0.78 |
| 60 | leucine | 50 | 0.0465 | 0.0879 | 0.95 | 1.09 | 0.87 |
| 5765 | Metabolite - 1142 | 35 | 0.0514 | 0.0959 | 0.85 | 1.02 | 0.83 |
| 1437 | succinate | 50 | 0.0575 | 0.1011 | 0.91 | 1.02 | 0.89 |
| 13589 | Metabolite - 3327 | 35 | 0.0595 | 0.1035 | 0.76 | 0.96 | 0.80 |
| 13214 | Metabolite - 3183-possible-gamma-L-glutamyl-L-phenylalanine-or-aspartame | 35 | 0.0602 | 0.1035 | 0.82 | 0.93 | 0.89 |
| 14785 | Isobar-glycochenodeoxycholic acid-glycodeoxycholic acid | 35 | 0.0625 | 0.1058 | 0.72 | 0.94 | 0.77 |
| 16506 | Metabolite - 4271 | 50 | 0.0629 | 0.1058 | 0.74 | 0.91 | 0.81 |
| 15140 | L-kynurenine | 35 | 0.0641 | 0.1065 | 0.99 | 1.06 | 0.93 |
| 1126 | alanine | 50 | 0.0692 | 0.1127 | 0.96 | 1.08 | 0.89 |
| 5809 | 3-indoxyl-sulfate | 35 | 0.0717 | 0.1155 | 0.90 | 1.06 | 0.85 |
| 15753 | hippuric acid | 35 | 0.0734 | 0.117 | 0.95 | 1.14 | 0.83 |
| 10604 | Metabolite - 2370 | 35 | 0.0747 | 0.1179 | 0.94 | 1.07 | 0.88 |
| 15220 | Metabolite - 3813 | 35 | 0.0877 | 0.1334 | 0.87 | 0.97 | 0.90 |
| 22130 | DL-phenyllactic acid | 35 | 0.0908 | 0.1362 | 0.94 | 1.07 | 0.87 |
| 10781 | Metabolite - 2469 | 35 | 0.0929 | 0.1369 | 0.85 | 1.01 | 0.85 |
| 12593 | Metabolite - 2973 | 50 | 0.0973 | 0.1405 | 0.92 | 1.01 | 0.92 |
| 12646 | Metabolite - 3018 | 50 | 0.1004 | 0.1436 | 0.95 | 1.00 | 0.95 |
| 1125 | isoleucine | 50 | 0.1027 | 0.1442 | 0.94 | 1.06 | 0.89 |
| 12751 | Metabolite - 3073 | 50 | 0.104 | 0.1447 | 0.93 | 1.04 | 0.90 |
| 594 | niacinamide | 35 | 0.1068 | 0.1472 | 0.71 | 0.81 | 0.88 |
| 12756 | Metabolite - 3077 | 50 | 0.1155 | 0.1578 | 0.95 | 1.01 | 0.94 |
| 10438 | gamma-glu-leu | 35 | 0.1182 | 0.1601 | 0.91 | 0.98 | 0.93 |
| 6402 | Metabolite - 3832 | 35 | 0.1228 | 0.1648 | 1.08 | 1.26 | 0.85 |
| 16511 | Metabolite - 4274 | 50 | 0.124 | 0.1649 | 0.97 | 1.08 | 0.90 |
| 8336 | Metabolite - 2005 | 35 | 0.1255 | 0.1655 | 0.92 | 1.02 | 0.90 |
| 1107 | allantoin | 50 | 0.1287 | 0.1683 | 0.82 | 0.95 | 0.86 |
| 12644 | Metabolite - 3016 | 50 | 0.1309 | 0.1697 | 0.96 | 1.01 | 0.95 |
| 5628 | Metabolite - 1086 | 35 | 0.1387 | 0.1773 | 0.80 | 0.96 | 0.84 |
| 12625 | Metabolite - 3002 | 50 | 0.1391 | 0.1773 | 0.96 | 1.03 | 0.93 |
| 20675 | 1,5-anhydro-D-glucitol | 50 | 0.15 | 0.1881 | 0.83 | 0.93 | 0.90 |
| 1284 | threonine | 50 | 0.152 | 0.1891 | 0.98 | 1.08 | 0.91 |
| 1493 | ornithine | 50 | 0.1545 | 0.1906 | 0.96 | 1.09 | 0.88 |
| 15506 | choline | 35 | 0.1557 | 0.1906 | 1.01 | 1.07 | 0.95 |
| 1649 | valine | 50 | 0.1643 | 0.1968 | 0.94 | 1.03 | 0.91 |
| 15128 | Metabolite - 1002 | 35 | 0.1674 | 0.1974 | 1.01 | 1.13 | 0.90 |
| 10785 | Metabolite - 2506 | 35 | 0.1677 | 0.1974 | 0.85 | 1.03 | 0.82 |
| 1898 | proline | 35 | 0.1727 | 0.2017 | 1.01 | 1.07 | 0.95 |
| 14239 | Metabolite - 3474 | 35 | 0.1851 | 0.2126 | 0.83 | 0.91 | 0.91 |
| 1508 | pantothenic acid | 35 | 0.1865 | 0.2126 | 0.99 | 1.08 | 0.92 |
| 2730 | gamma-L-glutamyl-L-glutamine | 35 | 0.1913 | 0.2152 | 0.71 | 0.80 | 0.89 |
| 12720 | Metabolite - 3056 | 35 | 0.1941 | 0.2152 | 0.93 | 0.99 | 0.94 |
| 10461 | Metabolite - 2313 | 35 | 0.2233 | 0.2355 | 1.03 | 1.13 | 0.91 |
| 6138 | Metabolite - 1213 | 35 | 0.2247 | 0.2355 | 0.73 | 0.89 | 0.82 |
| 1123 | inosine | 35 | 0.2361 | 0.2431 | 0.77 | 0.91 | 0.85 |
| 6270 | Metabolite - 1288 | 35 | 0.2473 | 0.2463 | 0.74 | 0.84 | 0.88 |
| 12767 | Metabolite - 3087 | 50 | 0.2479 | 0.2463 | 0.95 | 1.02 | 0.93 |
| 5664 | Metabolite - 1215 | 35 | 0.2567 | 0.2534 | 0.72 | 0.91 | 0.79 |
| 20699 | meso-erythritol | 50 | 0.2611 | 0.2561 | 1.02 | 1.06 | 0.96 |
| 12658 | Metabolite - 3026 | 50 | 0.2638 | 0.2571 | 0.92 | 0.96 | 0.95 |
| 1299 | tyrosine | 35 | 0.2691 | 0.2602 | 0.99 | 1.03 | 0.96 |
| 1647 | glutamine | 50 | 0.2703 | 0.2602 | 0.96 | 1.06 | 0.91 |
| 11499 | Metabolite - 2753 | 35 | 0.2775 | 0.2621 | 0.97 | 1.01 | 0.96 |
| 5580 | Metabolite - 1067 | 35 | 0.2872 | 0.268 | 1.07 | 1.24 | 0.86 |
| 12790 | Metabolite - 3108 | 50 | 0.2944 | 0.273 | 0.98 | 1.02 | 0.96 |
| 10143 | Metabolite - 2255 | 35 | 0.3001 | 0.2761 | 0.65 | 0.81 | 0.81 |
| 10492 | Metabolite - 2320 | 35 | 0.3148 | 0.2817 | 0.83 | 0.92 | 0.90 |
| 12784 | Metabolite - 3102 | 50 | 0.3181 | 0.2826 | 1.00 | 1.04 | 0.97 |
| 12856 | Metabolite - 3123 | 35 | 0.3196 | 0.2826 | 0.79 | 0.91 | 0.87 |
| 14933 | Metabolite - 3739 | 35 | 0.3307 | 0.2876 | 0.65 | 0.74 | 0.87 |
| 1301 | lysine | 50 | 0.3373 | 0.2916 | 0.97 | 1.06 | 0.91 |
| 15609 | Metabolite - 3969 | 35 | 0.3456 | 0.2971 | 0.98 | 1.01 | 0.97 |
| 12754 | Metabolite - 3075 | 50 | 0.3639 | 0.3093 | 0.84 | 0.89 | 0.94 |
| 7933 | Metabolite - 1911 | 35 | 0.3703 | 0.3097 | 0.67 | 0.78 | 0.86 |
| 7096 | Metabolite - 1612 | 35 | 0.3703 | 0.3097 | 0.76 | 0.83 | 0.92 |

TABLE 4-continued

Compounds that vary based on gender.

| 6208 | Metabolite - 1254 | 35 | 0.3813 | 0.3171 | 0.84 | 1.01 | 0.83 |
|---|---|---|---|---|---|---|---|
| 13142 | Metabolite - 3165 | 35 | 0.3932 | 0.3218 | 0.94 | 0.98 | 0.96 |
| 12666 | Metabolite - 3033 | 50 | 0.3933 | 0.3218 | 0.93 | 0.97 | 0.96 |
| 6122 | Metabolite - 1206 | 35 | 0.3954 | 0.3218 | 0.53 | 0.60 | 0.88 |
| 1574 | histamine | 35 | 0.4008 | 0.3241 | 1.00 | 1.04 | 0.97 |
| 12650 | Metabolite - 3022 | 50 | 0.4024 | 0.3241 | 1.01 | 1.05 | 0.96 |
| 2129 | oxitryptan | 35 | 0.4062 | 0.3254 | 0.86 | 0.91 | 0.95 |
| 9748 | Metabolite - 2212 | 35 | 0.4252 | 0.3389 | 0.93 | 0.99 | 0.94 |
| 16071 | Metabolite - 4020 | 50 | 0.4403 | 0.3491 | 0.89 | 0.94 | 0.95 |
| 10083 | Metabolite - 2248 | 35 | 0.4445 | 0.3506 | 0.61 | 0.69 | 0.87 |
| 12770 | Metabolite - 3090 | 50 | 0.4499 | 0.353 | 0.65 | 0.78 | 0.84 |
| 14715 | Metabolite - 3653 | 35 | 0.4563 | 0.3549 | 0.96 | 1.11 | 0.87 |
| 13200 | Metabolite - 3180 | 35 | 0.4645 | 0.3572 | 0.79 | 0.84 | 0.94 |
| 12795 | Metabolite - 3113 | 50 | 0.4697 | 0.3594 | 0.83 | 0.89 | 0.93 |
| 527 | lactate | 50 | 0.477 | 0.3618 | 0.96 | 1.01 | 0.95 |
| 12780 | Metabolite - 3098 | 50 | 0.4776 | 0.3618 | 0.78 | 0.84 | 0.92 |
| 21025 | iminodiacetic acid | 50 | 0.4853 | 0.364 | 0.77 | 0.94 | 0.82 |
| 577 | fructose | 50 | 0.4883 | 0.3644 | 0.59 | 0.65 | 0.90 |
| 7029 | Metabolite - 1597 | 35 | 0.5036 | 0.3697 | 0.98 | 1.00 | 0.98 |
| 1648 | serine | 50 | 0.5098 | 0.3697 | 0.98 | 1.03 | 0.96 |
| 1591 | N-acetyl-L-valine | 35 | 0.5166 | 0.3721 | 0.86 | 0.89 | 0.97 |
| 11777 | glycine | 50 | 0.5249 | 0.3723 | 0.98 | 1.03 | 0.95 |
| 12647 | Metabolite - 3019 | 50 | 0.5256 | 0.3723 | 0.96 | 0.98 | 0.98 |
| 19934 | inositol | 50 | 0.5299 | 0.3737 | 1.01 | 1.03 | 0.98 |
| 10544 | Metabolite - 2329 | 35 | 0.5876 | 0.4042 | 0.71 | 0.78 | 0.91 |
| 13744 | Metabolite - 3364 | 35 | 0.5891 | 0.4042 | 0.79 | 0.85 | 0.93 |
| 12109 | Metabolite - 2853 | 35 | 0.5904 | 0.4042 | 0.64 | 0.69 | 0.94 |
| 59 | histidine | 50 | 0.6 | 0.4042 | 0.98 | 1.02 | 0.97 |
| 12639 | Metabolite - 3012 | 50 | 0.6049 | 0.4042 | 0.95 | 0.98 | 0.98 |
| 16135 | Metabolite - 4077 | 50 | 0.6101 | 0.4059 | 0.87 | 0.91 | 0.96 |
| 11053 | Metabolite - 2567 | 35 | 0.6164 | 0.4066 | 0.95 | 0.98 | 0.98 |
| 10501 | Metabolite - 2321 | 35 | 0.6288 | 0.4092 | 0.96 | 1.02 | 0.95 |
| 5727 | Metabolite - 1126 | 35 | 0.6316 | 0.4092 | 0.75 | 0.79 | 0.94 |
| 12099 | Metabolite - 2850 | 35 | 0.6338 | 0.4092 | 0.82 | 0.85 | 0.96 |
| 15677 | 3-methyl-L-histidine/1-methyl-L-histidine | 35 | 0.6626 | 0.4162 | 0.66 | 0.70 | 0.94 |
| 5652 | Metabolite - 1090 | 35 | 0.6639 | 0.4162 | 0.28 | 0.31 | 0.89 |
| 10476 | Metabolite - 2316 | 35 | 0.6658 | 0.4162 | 0.86 | 0.90 | 0.95 |
| 2734 | gamma-L-glutamyl-L-tyrosine | 35 | 0.6691 | 0.4162 | 0.82 | 0.85 | 0.97 |
| 6130 | Metabolite - 1208 | 35 | 0.6746 | 0.4162 | 0.63 | 0.67 | 0.94 |
| 10156 | Metabolite - 2259 | 35 | 0.6795 | 0.4175 | 0.99 | 1.03 | 0.96 |
| 9313 | Metabolite - 2172 | 35 | 0.6821 | 0.4175 | 0.52 | 0.55 | 0.94 |
| 12670 | Metabolite - 3037 | 50 | 0.6908 | 0.4195 | 1.00 | 1.03 | 0.97 |
| 15365 | sn-Glycerol-3-phosphate | 50 | 0.7012 | 0.42 | 0.99 | 1.01 | 0.97 |
| 16091 | Metabolite - 4031 | 35 | 0.705 | 0.42 | 0.95 | 0.97 | 0.98 |
| 12763 | Metabolite - 3083 | 50 | 0.7054 | 0.42 | 0.82 | 0.85 | 0.97 |
| 11323 | Metabolite - 2711 | 35 | 0.714 | 0.4216 | 1.01 | 1.04 | 0.97 |
| 12768 | Metabolite - 3088 | 50 | 0.7211 | 0.4216 | 0.85 | 0.87 | 0.98 |
| 10551 | Metabolite - 2347 | 35 | 0.7232 | 0.4216 | 0.91 | 0.96 | 0.95 |
| 1670 | urea | 50 | 0.7243 | 0.4216 | 1.02 | 1.04 | 0.98 |
| 15234 | Metabolite - 3821 | 35 | 0.7247 | 0.4216 | 0.83 | 0.84 | 0.98 |
| 7359 | Metabolite - 1713 | 35 | 0.738 | 0.4251 | 0.91 | 0.95 | 0.96 |
| 10092 | Metabolite - 2250 | 35 | 0.7438 | 0.4251 | 0.52 | 0.55 | 0.94 |
| 10245 | Metabolite - 2269 | 35 | 0.7485 | 0.4251 | 0.87 | 0.91 | 0.96 |
| 15991 | L-alpha-glycerophosphoryl choline | 35 | 0.751 | 0.4251 | 0.84 | 0.87 | 0.97 |
| 16229 | Isobar-2: arabitol/adonitol/xylitol | 35 | 0.7562 | 0.4251 | 0.94 | 0.97 | 0.97 |
| 14837 | Metabolite - 3707 | 35 | 0.7674 | 0.4251 | 0.89 | 0.92 | 0.96 |
| 10087 | Metabolite - 2249 | 35 | 0.7705 | 0.4251 | 0.99 | 1.01 | 0.98 |
| 5687 | Metabolite - 1110 | 35 | 0.7767 | 0.4251 | 0.88 | 0.91 | 0.96 |
| 6362 | Metabolite - 1323-possible-p-cresol-sulfate | 35 | 0.7811 | 0.4251 | 0.77 | 0.81 | 0.96 |
| 10317 | Metabolite - 2279 | 35 | 0.7826 | 0.4251 | 0.63 | 0.65 | 0.97 |
| 1519 | sucrose | 50 | 0.8046 | 0.4334 | 0.57 | 0.60 | 0.95 |
| 6231 | Metabolite - 1262 | 35 | 0.8069 | 0.4334 | 0.56 | 0.59 | 0.95 |
| 12645 | Metabolite - 3017 | 50 | 0.8095 | 0.4334 | 0.96 | 0.97 | 0.99 |
| 6579 | Metabolite - 1398- | 35 | 0.8101 | 0.4334 | 1.02 | 1.03 | 0.99 |
| 7002 | Metabolite - 1576 | 35 | 0.8167 | 0.4339 | 0.94 | 0.95 | 0.99 |

TABLE 4-continued

Compounds that vary based on gender.

| | | | | | | | |
|---|---|---|---|---|---|---|---|
| 6413 | Metabolite - 1342-possible-phenylacetylglutamine | 35 | 0.8466 | 0.4437 | 0.92 | 0.94 | 0.98 |
| 16496 | Metabolite - 4251 | 50 | 0.8582 | 0.4452 | 0.91 | 0.92 | 0.98 |
| 27728 | glycerol-2-phosphate | 50 | 0.8664 | 0.4466 | 0.84 | 0.85 | 0.99 |
| 12864 | Metabolite - 3124 | 35 | 0.8727 | 0.4466 | 0.91 | 0.92 | 0.99 |
| 5669 | Metabolite - 1104 | 35 | 0.8841 | 0.4477 | 0.99 | 1.00 | 0.99 |
| 10478 | Metabolite - 2317 | 35 | 0.8866 | 0.4477 | 0.62 | 0.64 | 0.98 |
| 12769 | Metabolite - 3089 | 50 | 0.8967 | 0.4513 | 0.56 | 0.57 | 0.98 |
| 15063 | Metabolite - 3772 | 35 | 0.9078 | 0.4555 | 1.02 | 1.03 | 0.99 |
| 10296 | Metabolite - 2273 | 35 | 0.917 | 0.4555 | 0.60 | 0.61 | 0.98 |
| 14840 | Metabolite - 3708 | 35 | 0.9497 | 0.4673 | 0.95 | 0.96 | 1.00 |
| 13775 | Metabolite - 3370 | 35 | 0.9666 | 0.4721 | 0.93 | 0.93 | 1.00 |
| 18392 | theobromine | 35 | 0.9691 | 0.4721 | 0.79 | 0.80 | 0.99 |
| 13545 | Metabolite - 3322 | 35 | 0.9718 | 0.4721 | 0.85 | 0.86 | 1.00 |

Race-Associated Changes

There were a total of 24 compounds that are statistically significantly different based on race in this study. Of the 24 compounds, 7 had differences of greater than 50% in relative concentration between Blacks, Whites, and Hispanics. One of these significant differences is a strictly dietary metabolite, caffeine, while the other 6 are potentially dietary or biologically synthesized. Table 5 provides a listing of metabolites that differed with race.

TABLE 5

Compounds that differ by race.

| Compound | p-value | q-value | Black | White | Hispanic |
|---|---|---|---|---|---|
| 3-phospho-glycerate | 4.0E−02 | 1.2E−01 | 0.72 | 0.88 | 0.86 |
| alanine | 2.2E−03 | 1.7E−02 | 0.87 | 1.08 | 1.07 |
| alpha-keto-glutarate | 4.7E−02 | 1.3E−01 | 0.83 | 0.72 | 1.05 |
| alpha-tocopherol | 2.2E−02 | 8.9E−02 | 0.90 | 0.97 | 1.09 |
| caffeine | 3.7E−08 | 1.0E−05 | 0.27 | 1.06 | 0.75 |
| citric acid | 4.4E−02 | 1.2E−01 | 1.09 | 1.34 | 0.98 |
| creatinine | 1.4E−03 | 1.2E−02 | 1.04 | 0.95 | 0.95 |
| alanyl-alanine | 1.8E−05 | 8.0E−04 | 0.54 | 1.00 | 0.84 |
| homocysteine | 2.4E−02 | 8.9E−02 | 0.93 | 1.14 | 1.14 |
| pipecolic acid | 3.7E−04 | 4.7E−03 | 0.96 | 1.26 | 1.24 |
| guanidineacetic acid | 8.0E−03 | 4.4E−02 | 0.63 | 0.38 | 0.46 |
| guanosine-5-diphosphate | 3.3E−03 | 2.2E−02 | 0.57 | 0.70 | 0.79 |
| hippuric acid | 4.2E−02 | 1.2E−01 | 0.89 | 1.07 | 1.17 |
| histamine | 1.3E−02 | 6.3E−02 | 0.94 | 1.07 | 1.04 |
| isobar: theobromine/theophylline | 1.5E−07 | 2.1E−05 | 0.44 | 1.19 | 0.82 |
| lactate | 1.4E−02 | 6.4E−02 | 0.87 | 1.03 | 1.05 |
| methionine | 1.9E−02 | 7.8E−02 | 1.07 | 0.96 | 0.99 |
| N-6-trimethyl-1-lysine | 8.7E−03 | 4.6E−02 | 1.03 | 0.90 | 0.86 |
| N-N-dimethylarginine | 2.7E−02 | 9.3E−02 | 0.15 | 0.26 | 0.25 |
| ornithine | 1.1E−02 | 5.4E−02 | 0.85 | 1.13 | 1.06 |
| palmitoleic acid | 2.8E−03 | 1.9E−02 | 0.75 | 1.11 | 1.02 |
| pantothenic acid | 5.6E−02 | 1.4E−01 | 0.97 | 1.16 | 0.96 |
| proline | 7.4E−04 | 8.0E−03 | 0.83 | 1.09 | 1.09 |
| tartaric acid | 2.4E−02 | 8.9E−02 | 0.56 | 0.67 | 0.71 |
| myristic acid | 1.6E−02 | 7.0E−02 | 0.94 | 1.09 | 1.10 |
| trans-2-3-4-trimethoxycinnamic acid | 2.5E−03 | 1.8E−02 | 0.79 | 0.51 | 0.68 |
| urea | 2.2E−02 | 8.9E−02 | 0.95 | 0.99 | 1.14 |
| Metabolite - 1911 | 1.3E−04 | 2.9E−03 | 0.98 | 0.81 | 0.45 |
| Metabolite - 2005 | 6.2E−05 | 2.1E−03 | 0.83 | 0.95 | 1.13 |
| Metabolite - 2150 | 1.2E−04 | 2.9E−03 | 0.84 | 0.51 | 0.57 |
| Metabolite - 2250 | 4.2E−05 | 1.6E−03 | 0.80 | 0.55 | 0.33 |

TABLE 5-continued

Compounds that differ by race.

| Compound | p-value | q-value | Black | White | Hispanic |
|---|---|---|---|---|---|
| Metabolite - 3088 | 7.9E−05 | 2.4E−03 | 1.04 | 0.77 | 0.84 |
| Metabolite - 3230 | 1.4E−04 | 2.9E−03 | 0.97 | 1.12 | 1.00 |

One of the more interesting metabolites is palmitoleic acid, which is significantly lower in Blacks as compared to Whites and Hispanics. Palmitoleic acid is one of the major fatty acids in blood and in addition to being synthesized in the liver it is also available from numerous food products including fish, red meat, peanuts, etc. This difference is likely due to diet, although a genetic linkage cannot be ruled out. In the plasma of Black subjects, we observed palmitoleic acid levels that were more than 25% lower relative to the levels observed in Whites and Hispanics. Interestingly, this observation is consistent with two previous studies (Bhattacharyya, A. K., et al., 1987, Am J Clin Nutr. 46(1):41-6; and Kokatnur, M. G., et al., 1979, Am J Clin Nutr. 32(11): 2198-205). In Bhattacharyya's study of 714 deceased Black and White men, aged 25-44, they showed significantly elevated levels of palmitoleic acid from fat stores in tissues from Whites compared to Blacks. In Kokatnur's study of 406 men, a similar result was observed.

The differences in caffeine levels as a function of race were even greater than for palmitoleic acid. In our study we observed that Blacks generally have significantly reduced levels of caffeine as compared to Whites and Hispanics. Although a dietary difference cannot be ruled out, previous studies have reported elevated levels of potential metabolism of caffeine in Blacks, either due to a less frequent mutation that causes lower levels of CYP2D6 (Evans, W. E., et al., 1993, J Clin Invest. 91(5):2150-4), or increased levels of either CYP1A or n-acetyltransferase (NAT) (Relling, M. V., et al., 1992, Clin Pharmacol Ther. 52(6):643-58; and Butler, M. A., et al., 1992, Pharmacogenetics, 2(3):116-27).

Summary

Metabolomic analysis was applied to the plasma from 270 human subjects. The factors considered were age, gender, and race. More than 700 compounds in the plasma had detected differences in levels. Based on our statistical criteria, more than 300 compounds showed statistically significant differences for either age, gender or race. No obviously strong interactions were observed for these three factors, with the possible exception of urea. Finally, many trends were observed within our single study that were consistent with previously published clinical studies.

Example 2

Analytical Characterization of Unnamed Compounds

Table 6 below includes analytical characteristics of each of the unnamed metabolites listed in Tables 2-5 above. The table includes, for each listed Metabolite, the retention time (RT), retention index (RI), mass, quant. mass, and polarity obtained using the analytical methods described above. "Mass" refers to the mass of the $C^{12}$ isotope of the parent ion used in quantification of the compound. The values for "Quant Mass" give an indication of the analytical method used for quantification: "Y" indicates GC-MS and "1" and "2" indicate LC-MS. "Polarity" indicates the polarity of the quantitative ion as being either positive (+) or negative (−).

TABLE 6

Analytical Characteristics of Unnamed Metabolites

| COMPOUND_NAME | RT | RI | MASS | QUANT MASS | Polarity |
|---|---|---|---|---|---|
| Metabolite - 4276 | 13.92 | 2262.9 | 223.1 | Y | + |
| Metabolite - 4275 | 10.68 | 1887.0 | 271.1 | Y | + |
| Metabolite - 4274 | 10.37 | 1857.0 | 158.1 | Y | + |
| Metabolite - 4273 | 10.34 | 1845.7 | 457.2 | Y | + |
| Metabolite - 4272 | 10.28 | 1840.2 | 669.3 | Y | + |
| Metabolite - 4271 | 9.69 | 1777.4 | 419.2 | Y | + |
| Metabolite - 4251 | 4.09 | 1130.7 | 217 | Y | + |
| Metabolite - 4164 | 1.36 | 1451.1 | 484 | 2 | + |
| Metabolite - 4163 | 1.35 | 1444.1 | 225.3 | 1 | + |
| Metabolite - 4080 | 14.02 | 2270.2 | 299 | Y | + |
| Metabolite - 4077 | 14.00 | 2266.5 | 227 | Y | + |
| Metabolite - 4046 | 10.80 | 1890.5 | 353.1 | Y | + |
| Metabolite - 4043 | 10.29 | 1838.6 | 317.2 | Y | + |
| Metabolite - 4031-possible-norlevorphenol-sobutylphendienamide-amprolium | 14.26 | 14607 | 244.2 | 1 | + |
| Metabolite - 4020 | 7.91 | 1561.5 | 220.1 | Y | + |
| Metabolite - 4019 | 7.68 | 1534.5 | 174 | Y | + |
| Metabolite - 4017 | 7.62 | 1527.3 | 174 | Y | + |
| Metabolite - 4012 | 7.02 | 1458.2 | 357 | Y | + |
| Metabolite - 4003 | 3.94 | 4397 | 205 | 1 | + |
| Metabolite - 3992-possible-Cl-adduct-of-Formate-dimer | 1.4 | 1400 | 127.2 | 1 | − |
| Metabolite - 3977 | 11.03 | 11312 | 187.1 | 1 | − |
| Metabolite - 3972 | 6.16 | 6304 | 432.6 | 1 | − |
| Metabolite - 3969 | 3.81 | 4302 | 269.1 | 1 | + |
| Metabolite - 3968 | 1.39 | 1436 | 327.8 | 1 | + |
| Metabolite - 3962 | 10.22 | 10459 | 564.1 | 1 | + |
| Metabolite - 3951 | 8.41 | 8705.4 | 367.1 | 1 | + |
| Metabolite - 3899 | 4.41 | 4818.2 | 189.1 | 1 | − |
| Metabolite - 3882 | 12.6 | 12949.2 | 343.1 | 1 | − |
| Metabolite - 3843 | 9.54 | 9721.9 | 263.1 | 1 | + |
| Metabolite - 3834 | 9.2 | 9410.2 | 372.2 | 1 | + |
| Metabolite - 3830 | 8.42 | 8725 | 189 | 1 | − |
| Metabolite - 3821 | 7.36 | 7642 | 282.1 | 1 | + |
| Metabolite - 3816 | 4.16 | 4350 | 173.1 | 1 | − |
| Metabolite - 3813 | 3.81 | 4312 | 212.1 | 1 | + |
| Metabolite - 3805 | 2.49 | 2794 | 229.1 | 1 | + |
| Metabolite - 3783 | 1.37 | 1464 | 271.1 | 1 | + |
| Metabolite - 3772 | 2.22 | 2274 | 109 | 1 | + |
| Metabolite - 3759 | 13.81 | 14203 | 309.2 | 1 | − |
| Metabolite - 3752 | 8.61 | 8750.4 | 276.1 | 1 | + |
| Metabolite - 3739 | 15.79 | 16200.3 | 256.4 | 1 | + |
| Metabolite - 3708 | 1.66 | 1625.3 | 159.9 | 1 | + |
| Metabolite - 3707 | 13.07 | 13339.5 | 241 | 1 | + |
| Metabolite - 3668 | 9.63 | 9536 | 379.1 | 1 | + |
| Metabolite - 3667 | 9.17 | 9410.6 | 301.1 | 1 | + |
| Metabolite - 3664 | 8.72 | 8784.7 | 264.8 | 1 | + |
| Metabolite - 3663 | 8.4 | 8649 | 180.1 | 1 | + |
| Metabolite - 3653-Possible-stachydrine-or-pipcolate | 4.05 | 4500 | 144.1 | 1 | + |
| Metabolite - 3623 | 10.9 | 11553.6 | 152.1 | 1 | + |
| Metabolite - 3604 | 8.99 | 9551.9 | 214.2 | 1 | − |
| Metabolite - 3603 | 8.41 | 8971 | 313.6 | 1 | + |
| Metabolite - 3498 | 7.8 | 8368.7 | 279.1 | 1 | + |
| Metabolite - 3487 | 8.94 | 9554 | 648.9 | 1 | + |
| Metabolite - 3474 | 15.67 | 16524.3 | 228.3 | 1 | + |
| Metabolite - 3436 | 8.91 | 9157.1 | 157 | 1 | − |
| Metabolite - 3377 | 8.86 | 8963.9 | 270.2 | 1 | + |
| Metabolite - 3370 | 8.11 | 8529.1 | 226.2 | 1 | + |
| Metabolite - 3364 | 9.06 | 9172.1 | 189 | 1 | − |
| Metabolite - 4868 | 9.38 | 9530 | 531 | 1 | + |
| Metabolite - 4491 | 13.34 | 13588 | 331.2 | 1 | − |
| Metabolite - 3327 | 11.56 | 11784 | 385.3 | 1 | − |
| Metabolite - 3322 | 11.82 | 12044 | 383.2 | 1 | − |
| Metabolite - 3310 | 8.58 | 8787.3 | 177.1 | 1 | + |
| Metabolite - 3249 | 3.28 | 3298.3 | 141 | 1 | + |
| Metabolite - 3230 | 3.1 | 3043.2 | 245 | 1 | + |
| Metabolite - 3218 | 2.2 | 2257 | 148.1 | 1 | + |
| Metabolite - 3216 | 1.68 | 1743.8 | 405.7 | 1 | + |
| Metabolite - 3215 | 1.67 | 1733.8 | 173.8 | 1 | + |
| Metabolite - 3184 | 10.28 | 10364.4 | 223 | 1 | + |
| Metabolite - 3183-possible-gamma-L-glutamyl-L-phenylalanine-or-aspartame | 9.37 | 9441 | 295.2 | 1 | + |
| Metabolite - 3180 | 4.14 | 4356 | 139 | 1 | + |
| Metabolite - 3178 | 3.15 | 3280 | 210 | 1 | + |
| Metabolite - 3176-possible-creatine | 1.42 | 1511.4 | 132 | 1 | + |
| Metabolite - 3166 | 8.69 | 8746.5 | 394.2 | 1 | + |
| Metabolite - 3165 | 8.38 | 8472.2 | 265 | 1 | + |
| Metabolite - 3160 | 12.11 | 12247.3 | 361 | 1 | + |
| Metabolite - 3143 | 9.81 | 10070 | 160.1 | 1 | + |
| Metabolite - 3139 | 8.82 | 8934.5 | 176.1 | 1 | + |
| Metabolite - 3132 | 10.14 | 10392 | 260.2 | 1 | + |
| Metabolite - 3131 | 10.49 | 10770 | 192.9 | 1 | + |
| Metabolite - 3130 | 9.09 | 9328 | 158.2 | 1 | + |
| Metabolite - 3129 | 8.8 | 9012 | 337.1 | 1 | + |
| Metabolite - 3125 | 11.88 | 12095 | 187.1 | 1 | + |
| Metabolite - 3124 | 4.17 | 4545.7 | 307.1 | 1 | + |
| Metabolite - 3123 | 8.97 | 9100 | 334.2 | 1 | + |
| Metabolite - 3113 | 12.73 | 2113.5 | 406.2 | Y | + |
| Metabolite - 3110-phthalate-ester | 12.68 | 2107.0 | 148.9 | Y | + |
| Metabolite - 3109 | 12.56 | 2092.6 | 202.1 | Y | + |
| Metabolite - 3108 | 12.24 | 2056.5 | 246 | Y | + |
| Metabolite - 3103 | 12.09 | 2039.8 | 290.1 | Y | + |
| Metabolite - 3102 | 11.99 | 2028.2 | 217.1 | Y | + |
| Metabolite - 3101 | 11.93 | 2022.2 | 290 | Y | + |
| Metabolite - 3100 | 11.85 | 2013.2 | 204 | Y | + |
| Metabolite - 3099 | 11.77 | 2005.2 | 204 | Y | + |
| Metabolite - 3098 | 11.75 | 2003.0 | 308 | Y | + |
| Metabolite - 3097 | 11.64 | 1990.4 | 204 | Y | + |
| Metabolite - 3094 | 11.55 | 1980.6 | 299 | Y | + |
| Metabolite - 3093 | 11.50 | 1975.6 | 204 | Y | + |
| Metabolite - 3091 | 11.41 | 1966.2 | 232.1 | Y | + |
| Metabolite - 3090 | 11.31 | 1955.0 | 243.1 | Y | + |
| Metabolite - 3089 | 11.28 | 1951.5 | 116.9 | Y | + |
| Metabolite - 3088 | 11.23 | 1946.1 | 372.2 | Y | + |
| Metabolite - 3087 | 11.19 | 1942.0 | 174.1 | Y | + |
| Metabolite - 3086 | 11.16 | 1938.5 | 221 | Y | + |
| Metabolite - 3083 | 10.94 | 1916.1 | 204 | Y | + |
| Metabolite - 3080 | 10.75 | 1897.0 | 116.9 | Y | + |
| Metabolite - 3078 | 10.65 | 1887.0 | 203.1 | Y | + |
| Metabolite - 3077 | 10.44 | 1866.2 | 308.1 | Y | + |
| Metabolite - 3075 | 10.36 | 1857.9 | 204 | Y | + |
| Metabolite - 3074 | 10.22 | 1844.5 | 204.1 | Y | + |
| Metabolite - 3073 | 10.17 | 1838.8 | 362.1 | Y | + |

TABLE 6-continued

Analytical Characteristics of Unnamed Metabolites

| COMPOUND_NAME | RT | RI | MASS | QUANT MASS | Polarity |
|---|---|---|---|---|---|
| Metabolite - 3058 | 9.70 | 1786.9 | 335.1 | Y | + |
| Metabolite - 3056 | 9.19 | 9432 | 185.2 | 1 | + |
| Metabolite - 3052 | 8.7 | 8913.4 | 426.2 | 1 | + |
| Metabolite - 3040 | 9.27 | 1735.7 | 274.1 | Y | + |
| Metabolite - 3037 | 9.16 | 1722.6 | 299 | Y | + |
| Metabolite - 3036 | 9.07 | 1712.5 | 119.1 | Y | + |
| Metabolite - 3034 | 8.92 | 1694.9 | 299 | Y | + |
| Metabolite - 3033 | 8.88 | 1689.4 | 116.9 | Y | + |
| Metabolite - 3030 | 8.62 | 1659.7 | 320 | Y | + |
| Metabolite - 3029 | 8.48 | 1642.8 | 117.1 | Y | + |
| Metabolite - 3027 | 8.21 | 1610.6 | 142 | Y | + |
| Metabolite - 3026 | 8.17 | 1606.1 | 274.1 | Y | + |
| Metabolite - 3025 | 8.11 | 1600.3 | 274.1 | Y | + |
| Metabolite - 3022 | 7.98 | 1584.9 | 142 | Y | + |
| Metabolite - 3020 | 7.81 | 1564.1 | 292 | Y | + |
| Metabolite - 3019 | 7.74 | 1556.4 | 260.1 | Y | + |
| Metabolite - 3018 | 7.69 | 1550.1 | 263.2 | Y | + |
| Metabolite - 3017 | 7.61 | 1541.4 | 246.1 | Y | + |
| Metabolite - 3016 | 7.58 | 1537.5 | 186 | Y | + |
| Metabolite - 3012 | 7.17 | 1489.8 | 232 | Y | + |
| Metabolite - 3003 | 6.79 | 1446.6 | 218.1 | Y | + |
| Metabolite - 3002 | 6.74 | 1440.8 | 296.1 | Y | + |
| Metabolite - 2986 | 5.56 | 1304.3 | 201.1 | Y | + |
| Metabolite - 2978 | 5.01 | 1244.1 | 261.8 | Y | + |
| Metabolite - 2973 | 4.74 | 1213.4 | 281 | Y | + |
| Metabolite - 2915 | 3.77 | 1099.0 | 174 | Y | + |
| Metabolite - 2895 | 10.33 | 10620 | 284.1 | 1 | + |
| Metabolite - 2894 | 9.94 | 10320 | 226.1 | 1 | − |
| Metabolite - 2871 | 4.52 | 5609.5 | 458.8 | 1 | − |
| Metabolite - 2853 | 8.74 | 8923.5 | 578.4 | 1 | + |
| Metabolite - 2850 | 3.53 | 3827 | 522 | 1 | + |
| Metabolite - 2849-related-to-citric acid | 3.17 | 3045.5 | 482.6 | 1 | − |
| Metabolite - 2810 | 9.18 | 9363 | 447.9 | 1 | + |
| Metabolite - 2809 | 8.74 | 8923.5 | 699.8 | 1 | + |
| Metabolite - 2774 | 3.53 | 3796 | 230.9 | 1 | + |
| Metabolite - 2753 | 3.38 | 3358 | 147 | 1 | + |
| Metabolite - 2711 | 2.22 | 2300 | 123 | 1 | + |
| Metabolite - 2703 | 8.86 | 9054.8 | 384.1 | 1 | + |
| Metabolite - 2688 | 1.42 | 1614 | 182 | 1 | − |
| Metabolite - 2592 | 10.59 | 10778.4 | 697.2 | 1 | − |
| Metabolite - 2568 | 8.54 | 8790.8 | 342.1 | 1 | + |
| Metabolite - 2567 | 7.79 | 8164.7 | 247.1 | 1 | + |
| Metabolite - 2560 | 14.43 | 14754 | 235.2 | 1 | + |
| Metabolite - 2558 | 8.14 | 8674 | 153.1 | 1 | + |
| Metabolite - 2548 | 5.97 | 6016 | 202.9 | 1 | − |
| Metabolite - 2546 | 1.63 | 1747.3 | 129.1 | 1 | + |
| Metabolite - 2507 | 14.44 | 14843 | 481.4 | 1 | − |
| Metabolite - 2506 | 14.05 | 14437.5 | 624.4 | 1 | − |
| Metabolite - 2486 | 1.52 | 1667 | 635.7 | 1 | − |
| Metabolite - 2469 | 15.99 | 16436 | 502.3 | 1 | + |
| Metabolite - 2466 | 9.19 | 9519.9 | 624.8 | 1 | + |
| Metabolite - 2398 | 13.07 | 13405.8 | 404 | 1 | + |
| Metabolite - 2395 | 10.13 | 10447.6 | 471.9 | 1 | + |
| Metabolite - 2393 | 15.02 | 15461.4 | 250.4 | 1 | − |
| Metabolite - 2392 | 13.08 | 13460.4 | 379 | 1 | − |
| Metabolite - 2390 | 6.09 | 6144.9 | 517.4 | 1 | + |
| Metabolite - 2389 | 1.49 | 1641.5 | 314.9 | 1 | − |
| Metabolite - 2388 | 16.16 | 16567 | 259.1 | 1 | − |
| Metabolite - 2387 | 8.55 | 8838.5 | 182.1 | 1 | + |
| Metabolite - 2386 | 11.94 | 12320.3 | 539.2 | 1 | − |
| Metabolite - 2370 | 16.13 | 16561.2 | 476.4 | 1 | − |
| Metabolite - 2366 | 8.47 | 8870.2 | 271 | 1 | + |
| Metabolite - 2348 | 13.91 | 14293.5 | 448.3 | 1 | + |
| Metabolite - 2347 | 13.65 | 14091 | 450.1 | 1 | + |
| Metabolite - 2329 | 11.76 | 12177.6 | 541.2 | 1 | − |
| Metabolite - 2326 | 11.39 | 11755.8 | 595.2 | 1 | + |
| Metabolite - 2321 | 13.44 | 13832.6 | 314.3 | 1 | + |
| Metabolite - 2320 | 12.27 | 12640 | 288.3 | 1 | + |
| Metabolite - 2317 | 9.1 | 9410 | 592.9 | 1 | + |
| Metabolite - 2316 | 8.82 | 9163.6 | 100.1 | 1 | + |
| Metabolite - 2313 | 1.56 | 1685.6 | 352.9 | 1 | − |
| Metabolite - 2292 | 2.4 | 2513.6 | 343.9 | 1 | − |
| Metabolite - 2291 | 10.55 | 10921 | 213.1 | 1 | − |
| Metabolite - 2287 | 12.95 | 13335.6 | 502.8 | 1 | + |
| Metabolite - 2285 | 2 | 2146 | 699.6 | 1 | − |
| Metabolite - 2281 | 13.93 | 14325.1 | 505.2 | 1 | − |
| Metabolite - 2279 | 12.38 | 12781 | 490.1 | 1 | + |
| Metabolite - 2277 | 10.07 | 10457 | 201.1 | 1 | − |
| Metabolite - 2276 | 9.78 | 10129.3 | 199 | 1 | − |
| Metabolite - 2273 | 9.28 | 9643.2 | 586.5 | 1 | + |
| Metabolite - 2271 | 12.95 | 13348.8 | 413.2 | 1 | − |
| Metabolite - 2269 | 10.36 | 10727 | 255.1 | 1 | − |
| Metabolite - 2267 | 10 | 10375.6 | 663.1 | 1 | + |
| Metabolite - 2259 | 11.25 | 11586 | 383.2 | 1 | − |
| Metabolite - 2258 | 11.09 | 11425 | 286.3 | 1 | + |
| Metabolite - 2257 | 10.07 | 10372 | 245.1 | 1 | − |
| Metabolite - 2256 | 9.93 | 10232 | 460.8 | 1 | + |
| Metabolite - 2255 | 9.08 | 9394 | 539.1 | 1 | + |
| Metabolite - 2250 | 14.26 | 14668.4 | 286.3 | 1 | + |
| Metabolite - 2249 | 14.21 | 14570.9 | 267.2 | 1 | − |
| Metabolite - 2248 | 14.2 | 14610.4 | 498.4 | 1 | − |
| Metabolite - 2247 | 14 | 14406 | 399.3 | 1 | − |
| Metabolite - 2237 | 10.14 | 10453.6 | 453.1 | 1 | + |
| Metabolite - 2231 | 14.31 | 14629 | 278.1 | 1 | + |
| Metabolite - 2212 | 15.96 | 16271 | 478.2 | 1 | + |
| Metabolite - 2193 | 8.39 | 8699 | 233.1 | 1 | + |
| Metabolite - 2185 | 9.22 | 9499.4 | 246.2 | 1 | + |
| Metabolite - 2172 | 1.53 | 1639 | 279.1 | 1 | + |
| Metabolite - 2150 | 13.27 | 13616.5 | 466.1 | 1 | + |
| Metabolite - 2139 | 8.09 | 8416.7 | 218.1 | 1 | + |
| Metabolite - 2100 | 1.33 | 1532.9 | 499 | 1 | + |
| Metabolite - 2074 | 2.24 | 2380.9 | 280.1 | 1 | + |
| Metabolite - 2056 | 1.37 | 1499 | 165.1 | 1 | − |
| Metabolite - 2055 | 1.37 | 1502 | 269.9 | 1 | + |
| Metabolite - 2026 | 1.36 | 1556.2 | 239.2 | 1 | + |
| Metabolite - 2005 | 8.62 | 9048 | 232.1 | 1 | + |
| Metabolite - 1988 | 11.14 | 11515 | 190.1 | 1 | + |
| Metabolite - 1979-Cl-adduct-of-C6H10O5 | 1.52 | 1690.3 | 199 | 1 | − |
| Metabolite - 1977 | 3.56 | 3815 | 260.9 | 1 | + |
| Metabolite - 1951 | 13.92 | 14318.6 | 397.3 | 1 | − |
| Metabolite - 1911 | 11.42 | 11799.6 | 464.1 | 1 | + |
| Metabolite - 5233 | 2.57 | 2624 | 138.1 | 1 | + |
| Metabolite - 1836 | 2.1 | 2215.5 | 205.9 | 1 | − |
| Metabolite - 1834 | 1.64 | 1794.5 | 104 | 1 | − |
| Metabolite - 1831-possible-Cl-adduct-of-citrulline | 1.46 | 1638.7 | 209.9 | 1 | − |
| Metabolite - 1829 | 1.43 | 1600 | 135 | 1 | − |
| Metabolite - 1819 | 1.36 | 1539.6 | 244.8 | 1 | − |
| Metabolite - 1718 | 8.43 | 8647 | 457.9 | 1 | + |
| Metabolite - 1713 | 2.73 | 2770 | 174 | 1 | − |
| Metabolite - 1693 | 14.98 | 15155 | 399.2 | 1 | + |
| Metabolite - 1656 | 1.46 | 1509 | 154.9 | 1 | + |
| Metabolite - 1638 | 15.45 | 15633 | 627.1 | 1 | + |
| Metabolite - 1613 | 8.83 | 9029.9 | 454.1 | 1 | + |
| Metabolite - 1612 | 8.64 | 8850.3 | 230.9 | 1 | + |
| Metabolite - 1597 | 3.66 | 3894 | 265.9 | 1 | + |
| Metabolite - 1596 | 3.66 | 3902 | 185 | 1 | + |
| Metabolite - 1576 | 2.51 | 2530 | 247.1 | 1 | + |
| Metabolite - 1575 | 2.25 | 2243.5 | 219.1 | 1 | + |
| Metabolite - 1573 | 1.63 | 1669 | 170.9 | 1 | − |
| Metabolite - 1498 | 1.56 | 1650 | 143.1 | 1 | − |
| Metabolite - 1465 | 3.45 | 3600 | 162.1 | 1 | + |
| Metabolite - 1398-possible-nonanoylmorpholine- | 13.21 | 13698.5 | 228.2 | 1 | + |
| Metabolite - 1380 | 14.43 | 14937.2 | 295.1 | 1 | + |
| Metabolite - 1376 | 13.93 | 14421 | 1487 | 1 | + |
| Metabolite - 1370 | 11.46 | 11912.3 | 362.2 | 1 | + |
| Metabolite - 1351 | 1.77 | 1936.5 | 177.9 | 1 | + |

TABLE 6-continued

Analytical Characteristics of Unnamed Metabolites

| COMPOUND_NAME | RT | RI | MASS | QUANT MASS | Polarity |
|---|---|---|---|---|---|
| Metabolite - 1350 | 13.75 | 14248.7 | 909.8 | 1 | + |
| Metabolite - 1346 | 1.27 | 1449.5 | 113 | 1 | − |
| Metabolite - 1345 | 13.27 | 13764.5 | 369.3 | 1 | − |
| Metabolite - 1342-possible-phenylacetylglutamine-or-formyl-N-acetyl-5-methoxykynurenamine | 9.04 | 9459.4 | 265.2 | 1 | + |
| Metabolite - 3832 | 8.28 | 8696 | 173 | 1 | − |
| Metabolite - 1335 | 8.74 | 9162.2 | 367.2 | 1 | + |
| Metabolite - 1333 | 3.05 | 3194.6 | 321.9 | 1 | + |
| Metabolite - 1327-possible-bilirubin | 13.22 | 13705.9 | 585.4 | 1 | + |
| Metabolite - 1323-possible-4-sulfobenzyl-alcohol | 9.31 | 9719.8 | 187 | 1 | − |
| Metabolite - 1305 | 14.23 | 14389.4 | 264.9 | 1 | + |
| Metabolite - 1303 | 9.01 | 9178 | 527.8 | 1 | + |
| Metabolite - 1289 | 8.96 | 9139.7 | 338.4 | 1 | + |
| Metabolite - 1288 | 2.11 | 2120.5 | 302 | 1 | − |
| Metabolite - 1287 | 14.2 | 14363.9 | 353.2 | 1 | + |
| Metabolite - 1286 | 14.41 | 14579.8 | 229 | 1 | + |
| Metabolite - 1284 | 9.71 | 9910 | 486.9 | 1 | + |
| Metabolite - 1264 | 10.69 | 10878.5 | 617.8 | 1 | − |
| Metabolite - 1983 | 10.25 | 10418.7 | 777 | 1 | + |
| Metabolite - 1262 | 9.97 | 10162.7 | 808.9 | 1 | + |
| Metabolite - 1261 | 10.73 | 10905.1 | 528.4 | 1 | + |
| Metabolite - 1254 | 9.8 | 9987.5 | 733.4 | 1 | + |
| Metabolite - 1252 | 8.12 | 8326 | 229.9 | 1 | + |
| Metabolite - 1249 | 9.02 | 9201.3 | 630.1 | 1 | + |
| Metabolite - 1245 | 9.28 | 9450.9 | 553.4 | 1 | + |
| Metabolite - 1244 | 15.28 | 15436.8 | 343.4 | 1 | − |
| Metabolite - 1243 | 8.97 | 9147.7 | 751.5 | 1 | + |
| Metabolite - 1242 | 8.43 | 8627.6 | 355.9 | 1 | + |
| Metabolite - 1221-possible-phthalate | 12.5 | 12665.8 | 221.1 | 1 | − |
| Metabolite - 1220 | 15.24 | 15402.5 | 319.2 | 1 | + |
| Metabolite - 1213 | 8.92 | 9101.8 | 244.8 | 1 | + |
| Metabolite - 1212 | 9.1 | 9284 | 584.9 | 1 | + |
| Metabolite - 1211: IHWESASLLR | 9.9 | 10083.7 | 606.5 | 1 | + |
| Metabolite - 1209 | 8.89 | 9077.8 | 426.9 | 1 | + |
| Metabolite - 1208 | 15.33 | 15494 | 319.4 | 1 | − |
| Metabolite - 1206-possible-methyltestosterone-and-others | 15.32 | 15475.1 | 303.2 | 1 | + |
| Metabolite - 1203-possible-acetylbrowniine-tricornine-germine-or-veracevine | 9.11 | 9288 | 510.2 | 1 | + |
| Metabolite - 1202 | 8.96 | 9142.5 | 501.7 | 1 | + |
| Metabolite - 1190 | 8.83 | 9130 | 928.5 | 1 | + |
| Metabolite - 1188 | 8.83 | 9017 | 619.9 | 1 | + |
| Metabolite - 1187 | 8.8 | 9017 | 559.9 | 1 | + |
| Metabolite - 1186 | 8.83 | 9000 | 529.6 | 1 | + |
| Metabolite - 1183 | 8.56 | 8765 | 365.8 | 1 | + |
| Metabolite - 1142-possible-5-hydroxypentanoate-or-beta-hydroxyisovaleric acid | 8.54 | 8739 | 117 | 1 | − |
| Metabolite - 1129 | 5.16 | 5419 | 260.1 | 1 | + |
| Metabolite - 1127 | 12.18 | 12369 | 363.1 | 1 | + |
| Metabolite - 1126 | 3.04 | 3188 | 175.1 | 1 | + |
| Metabolite - 1125 | 3.94 | 4202 | 221.1 | 1 | + |
| Metabolite - 1122 | 4.45 | 4701 | 233.1 | 1 | + |
| Metabolite - 1116 | 4.2 | 4480 | 103.4 | 1 | − |
| Metabolite - 1114 | 2.19 | 2198 | 104.1 | 1 | + |
| Metabolite - 1111-possible-methylnitronitro-soguanidine-or-ethyl-thiocarbamoylacetate | 2.69 | 2782 | 148.1 | 1 | + |
| Metabolite - 1110 | 11.66 | 11841 | 269.1 | 1 | − |
| Metabolite - 1105 | 11.35 | 11560 | 229 | 1 | − |
| Metabolite - 1104 | 2.43 | 2410 | 201 | 1 | − |
| Metabolite - 1215 | 9.39 | 9567 | 550 | 1 | + |
| Metabolite - 1090 | 11.26 | 11535 | 719 | 1 | + |
| Metabolite - 1089 | 2.01 | 2017 | 346.9 | 1 | + |
| Metabolite - 1088 | 13.12 | 13298 | 369.1 | 1 | − |
| Metabolite - 1086 | 4.56 | 4811 | 294.1 | 1 | + |
| Metabolite - 1085-possible-solobinine-or-4-aminoestra-1-3-5-10-triene-3-17beta-diol | 15.82 | 15964 | 288.1 | 1 | + |
| Metabolite - 1083 | 10.71 | 10905 | 723.5 | 1 | + |
| Metabolite - 1071-possible-type-of-phthalate | 15.23 | 15445 | 279.3 | 1 | + |
| Metabolite - 1069-possible-dehydroepiandrosterone-sulfate- | 12.55 | 12930 | 367.2 | 1 | − |
| Metabolite - 1067 | 10.03 | 10216 | 481.6 | 1 | + |
| Metabolite - 1065 | 9.66 | 9870 | 769 | 1 | + |
| Metabolite - 1062-possible-4-hydroxyphenyl-glyoxylate-or-phthalate-or-Formylsalicylic acid | 9.29 | 9491 | 165.1 | 1 | − |
| Metabolite - 1061-Possible-type-of-phthalate | 14.67 | 14885 | 279 | 1 | + |

Example 3

Application of Metabolomic Analysis to Predict Age and Generate a Biochemical Age Index (BAI)

This example describes how metabolic analysis is used to predict the metabolic age of an individual and generate a Biochemical Age Index (BAI) to be used to determine the MetaboScore for an individual.

Regression analysis was performed to evaluate the ability to predict age based upon the metabolomic results. The inclusion criterion for addition to the model was that the p-value was less than 0.05, which resulted in fewer total variables in the final model than using either the adjusted R-squared or the Akaike Information Criterion (AIC) for variable selection. Due to the number of gender differences, regressions were performed separately for each gender. Named compounds and unnamed compounds, excluding xenobiotics, were considered for the models. The regression results are shown in Table 7 and FIG. 3. Table 7 lists the biomarker compounds that comprise the model.

TABLE 7

Stepwise regression analysis for predicting age.

|  | Estimate | StdErr | t-value | p-value |
|---|---|---|---|---|
| FEMALE |  |  |  |  |
| Intercept | 13.63 | 5.46 | 2.50 | 0.01416 |
| glutamic acid | 2.44 | 0.73 | 3.34 | 0.001178 |
| histidine | −3.44 | 1.16 | −2.96 | 0.003788 |
| Metabolite - 3078 | 4.40 | 1.56 | 2.83 | 0.005643 |
| inositol | 4.79 | 1.60 | 3.00 | 3.36E−03 |
| Metabolite - 3087 | 4.97 | 1.16 | 4.28 | 4.14E−05 |
| Metabolite - 3094 | 4.86 | 1.28 | 3.80 | 0.000244 |
| lysine | −2.50 | 0.82 | −3.07 | 0.002757 |
| Metabolite - 4077 | −2.51 | 0.98 | −2.57 | 0.011502 |
| oxitryptan | −4.67 | 0.96 | −4.88 | 3.86E−06 |
| Dehydroepiandrosterone (DHEA-S) | −2.55 | 0.69 | −3.70 | 0.000342 |
| Metabolite - 1085 | 3.16 | 1.14 | 2.76 | 0.006751 |
| 3-indoxyl-sulfate | 2.54 | 0.64 | 4.00 | 0.000118 |
| Metabolite - 1264 | −0.36 | 0.08 | −4.38 | 2.85E−05 |
| Metabolite - 1288 | −1.52 | 0.62 | −2.43 | 0.01683 |
| Metabolite - 1656 | −3.72 | 0.83 | −4.46 | 2.07E−05 |
| Metabolite - 1831 | 5.04 | 0.92 | 5.45 | 3.38E−07 |
| Metabolite - 2074 | 2.31 | 0.35 | 6.52 | 2.59E−09 |
| Metabolite - 2231 | −7.25 | 1.12 | −6.45 | 3.63E−09 |
| Metabolite - 2257 | −1.17 | 0.22 | −5.28 | 7.10E−07 |
| Metabolite - 2259 | −1.09 | 0.37 | −2.92 | 0.004242 |
| gamma-glu-leu | 6.86 | 1.72 | 3.98 | 1.29E−04 |
| Metabolite - 2393 | −5.35 | 1.48 | −3.61 | 0.000475 |
| Metabolite - 2486 | 0.73 | 0.36 | 1.99 | 0.048984 |
| Metabolite - 2560 | 8.40 | 1.84 | 4.57 | 1.37E−05 |
| Metabolite - 2753 | −4.39 | 1.78 | −2.46 | 0.015458 |
| Metabolite - 2871 | 1.92 | 0.69 | 2.81 | 0.005975 |
| Metabolite - 3056 | −4.38 | 1.18 | −3.73 | 0.000317 |
| Metabolite - 3183 | −3.28 | 0.65 | −5.07 | 1.76E−06 |
| Metabolite - 3218 | 12.36 | 1.69 | 7.32 | 5.50E−11 |
| Metabolite - 3707 | 1.24 | 0.22 | 5.53 | 2.38E−07 |
| Metabolite - 3951 | 7.42 | 1.39 | 5.36 | 5.06E−07 |
| Metabolite - 3962 | 3.70 | 0.65 | 5.68 | 1.24E−07 |
| Metabolite - 3969 | −4.19 | 2.28 | −1.84 | 0.068653 |
| R2 = 91%. AdjR2 = 89% | AdjR2 = 89 |  |  |  |
| MALE |  |  |  |  |
| Intercept | 41.06 | 5.04 | 8.15 | 7.02E−13 |
| Metabolite - 3058 | −4.24 | 1.79 | −2.37 | 0.019657 |
| 1,5-anhydro-D-glucitol | −7.99 | 1.38 | −5.80 | 6.63E−08 |
| inositol | 11.62 | 1.79 | 6.50 | 2.55E−09 |
| Metabolite - 4272 | −10.96 | 1.71 | −6.41 | 3.83E−09 |
| succinate | −4.57 | 1.20 | −3.82 | 0.000227 |
| hypoxanthine | −0.27 | 0.10 | −2.59 | 0.010974 |
| gamma-L-glutamyl-L-tyrosine | −5.91 | 1.50 | −3.93 | 0.000148 |
| Metabolite - 1088 | −1.28 | 0.46 | −2.81 | 0.00594 |
| Metabolite - 1206 | 1.21 | 0.58 | 2.08 | 0.039735 |
| Metabolite - 1718 | 1.23 | 0.47 | 2.61 | 0.0104 |
| Metabolite - 2237 | −0.69 | 0.25 | −2.77 | 0.006514 |
| Metabolite - 2269 | 0.56 | 0.24 | 2.32 | 0.022002 |
| Metabolite - 2271 | −5.05 | 0.72 | −6.98 | 2.46E−10 |
| Metabolite - 2273 | 2.29 | 0.79 | 2.88 | 0.004846 |
| Metabolite - 2285 | 2.97 | 1.04 | 2.87 | 0.00498 |
| Metabolite - 2486 | −1.00 | 0.49 | −2.05 | 0.042362 |
| Metabolite - 2546 | 1.93 | 0.42 | 4.61 | 1.1E−05 |
| Metabolite - 3052 | 11.80 | 2.46 | 4.80 | 5.13E−06 |
| Metabolite - 3123 | −0.46 | 0.14 | −3.29 | 0.001353 |
| creatine | 5.51 | 1.01 | 5.43 | 3.57E−07 |

TABLE 7-continued

Stepwise regression analysis for predicting age.

|  | Estimate | StdErr | t-value | p-value |
|---|---|---|---|---|
| Metabolite - 4164 | 7.56 | 2.10 | 3.61 | 0.000472 |
| theobromine | −0.77 | 0.33 | −2.32 | 0.022258 |
| R2 = 85%, adj R2 = 82% |  |  |  |  |

Studentized residuals are used to identify the data points which do not appear to be consistent with the rest of the data (i.e. outliers). In this study, outliers represent the individuals that cannot be fitted well to the model; that is, the predicted metabolic age is significantly different from the actual chronological age. In this case, the studentized residuals were scaled to have variance equal to one (scaled by the "hat" matrix (Hoaglin, D. C. and R. E. Welsch (1978). "The Hat Matrix in Regression and ANOVA." *The American Statistician* 32(1): 17-22.)) and outliers were determined based on studentized residuals greater than absolute value of 2.0. Ten individuals, six females and four males, were identified as outliers. Of the six females, four had a predicted age younger than the actual chronological age, while two were predicted as older than the actual chronological age. For the males, two were chronologically older and two were chronologically younger than the predicted age. The data is presented graphically in FIG. 3 with the outlying points circled. The individuals that are chronologically older than the predicted age are the circled points below the solid diagonal line and the individuals that are chronologically younger than the predicted age are the circled points above the solid diagonal line.

To generate a Biochemical Age Index, the first step is to identify named compounds associated with age. Then remove the scores of the obvious outlier compounds. Confirm that the compounds are biologically reasonable (not an exogenous compound/xenobiotic, e.g. caffeine). Check for obvious gender and racial differences. Find the variables (i.e. compounds) that are correlated to the selected variables (i.e. compounds). That is, identify sets and/or groups of correlated compounds by searching for other compounds/metabolites that are correlated with the compounds/metabolites that are correlated with age. Build a simple index using these compound groups or sets.

Any of a number of statistical methods can be used to scan the compounds to find those that change with age. For example, polynomial fit analysis of compound concentration versus age, spline fit analysis of compound concentration versus age, simple 2-way scatter plot of compound concentration versus age, etc. In this example, linear regression was used to find compound levels that change with age. The compound levels in each individual(s) of each age were analyzed with programs for regression analysis using the Partionater, 4.1.0 (available on the worldwide web at GoldenHelix.com) and SAS JMP 6.0.2 (available on the worldwide web at sas.com). Table 8 lists a few of the named compounds from this regression analysis.

TABLE 8

Biomarker compounds that change with age

| Compound | Library | P | aP | FDR(aP) | bP | Var. # |
|---|---|---|---|---|---|---|
| normetanephrine- | 50 | 1.15E−15 | 1.15E−15 | 1.42E−13 | 1.42E−13 | 43 |
| valine | 50 | 4.86E−14 | 4.86E−14 | 2.99E−12 | 5.98E−12 | 128 |
| ornithine | 50 | 5.29E−14 | 5.29E−14 | 2.17E−12 | 6.51E−12 | 45 |
| alanine | 50 | 2.11E−13 | 2.11E−13 | 6.48E−12 | 2.59E−11 | 13 |
| glutamine | 50 | 6.42E−13 | 6.42E−13 | 1.58E−11 | 7.90E−11 | 28 |
| tyramine | 50 | 5.33E−12 | 5.33E−12 | 1.09E−10 | 6.55E−10 | 126 |
| leucine | 50 | 8.57E−12 | 8.57E−12 | 1.51E−10 | 1.05E−09 | 36 |
| L-arabitol | 35 | 1.55E−11 | 1.55E−11 | 2.38E−10 | 1.91E−09 | 171 |
| glutamic acid | 50 | 3.31E−11 | 3.31E−11 | 4.52E−10 | 4.07E−09 | 27 |
| glycine | 50 | 7.80E−11 | 7.80E−11 | 9.59E−10 | 9.59E−09 | 31 |
| lactate | 50 | 1.92E−10 | 1.92E−10 | 2.14E−09 | 2.36E−08 | 35 |
| serine | 50 | 2.25E−10 | 2.25E−10 | 2.31E−09 | 2.77E−08 | 120 |
| pyrophosphate | 50 | 2.34E−10 | 2.34E−10 | 2.21E−09 | 2.88E−08 | 119 |
| isoleucine | 50 | 4.48E−10 | 4.48E−10 | 3.94E−09 | 5.51E−08 | 34 |
| saccharopine | 35 | 6.14E−10 | 6.14E−10 | 5.03E−09 | 7.55E−08 | 443 |
| proline | 50 | 8.92E−10 | 8.92E−10 | 6.86E−09 | 1.10E−07 | 118 |
| dulcitol | 50 | 2.49E−09 | 2.49E−09 | 1.80E−08 | 3.06E−07 | 21 |
| benzoic acid | 50 | 1.07E−08 | 1.07E−08 | 7.33E−08 | 1.32E−06 | 17 |
| aspartate | 50 | 4.07E−08 | 4.07E−08 | 2.63E−07 | 5.00E−06 | 48 |
| threonine | 50 | 7.51E−08 | 7.51E−08 | 4.62E−07 | 9.23E−06 | 124 |
| aspartate | 35 | 2.44E−07 | 2.44E−07 | 1.43E−06 | 3.00E−05 | 143 |
| phosphate | 50 | 8.08E−07 | 8.08E−07 | 4.52E−06 | 9.93E−05 | 47 |
| uridine | 35 | 1.08E−06 | 1.08E−06 | 5.80E−06 | 1.33E−04 | 451 |
| 2-amino-butyrate | 50 | 1.56E−06 | 1.56E−06 | 7.99E−06 | 1.92E−04 | 6 |
| xanthine | 35 | 3.04E−06 | 3.04E−06 | 1.50E−05 | 3.74E−04 | 453 |
| histidine | 50 | 3.70E−06 | 3.70E−06 | 1.75E−05 | 4.55E−04 | 33 |
| urea | 50 | 5.45E−06 | 5.45E−06 | 2.48E−05 | 6.70E−04 | 127 |
| alpha-L-sorbopyranose | 50 | 5.47E−06 | 5.47E−06 | 2.40E−05 | 6.73E−04 | 14 |
| malic acid | 50 | 1.04E−05 | 1.04E−05 | 4.41E−05 | 1.28E−03 | 37 |

Many of these compounds that change in levels and that are correlated with age are also correlated with one another (FIG. 1). The first five on the list in Table 8 above were selected to illustrate this point. The correlations for those compounds are shown in Table 9.

TABLE 9

Compound correlations

| Correlations | alanine | glutamine | normetanephrine- | ornithine | valine |
|---|---|---|---|---|---|
| alanine | 1.0000 | 0.5112 | 0.6352 | 0.7723 | 0.8419 |
| glutamine | 0.5112 | 1.0000 | 0.4390 | 0.6075 | 0.5444 |
| normetanephrine | 0.6352 | 0.4390 | 1.0000 | 0.6198 | 0.6342 |
| ornithine | 0.7723 | 0.6075 | 0.6198 | 1.0000 | 0.8363 |
| valine | 0.8419 | 0.5444 | 0.6342 | 0.8363 | 1.000 |

Figure 4:
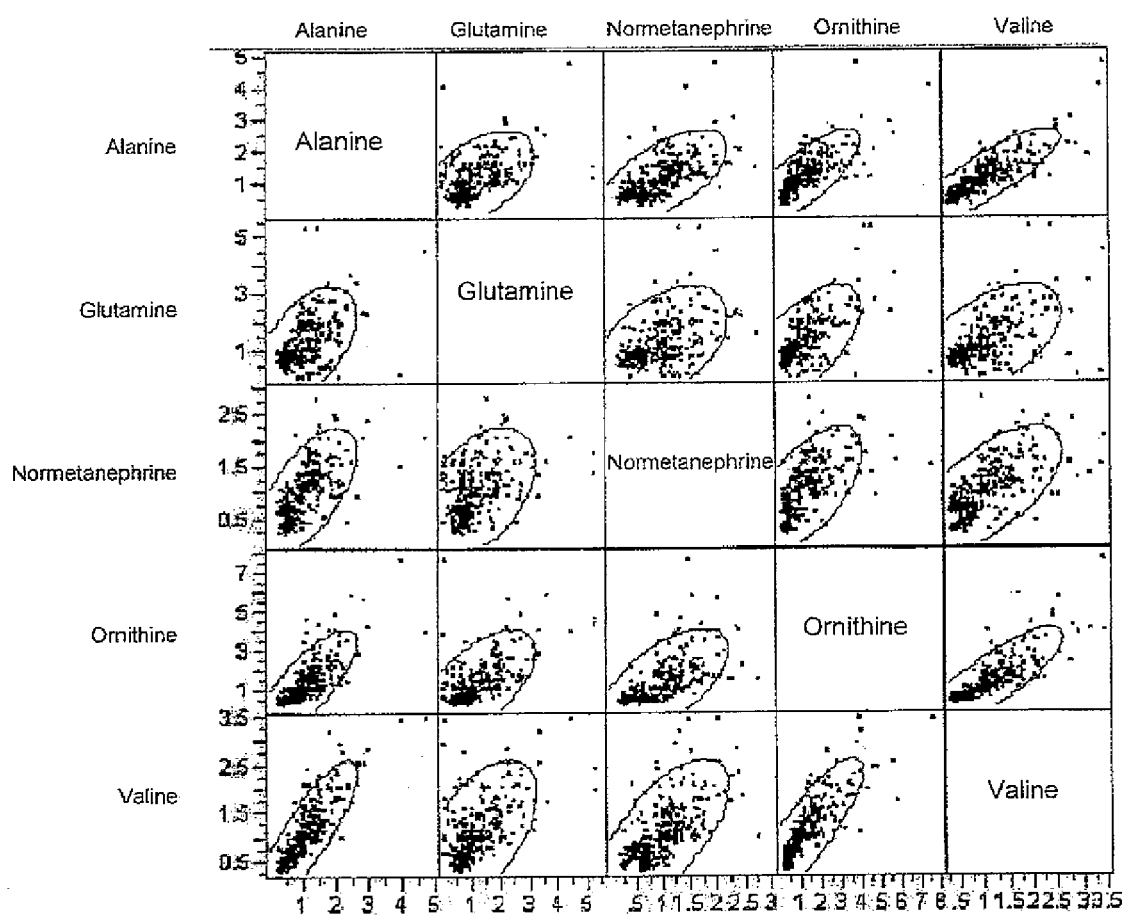
FIG. 4 is a matrix of scatterplots showing an example of compounds that are increased with age and that are also correlated with one another.

Scatter plots that illustrate the correlation between the pairs of compounds in Table 9 are shown in FIGS. 4 and 5. As shown in Table 10, some of these compounds are also correlated significantly with age.

TABLE 10

Some compounds with a significant correlation with age.

| Variable (Compound) | $R^2$ |
|---|---|
| Alanine | 0.183 |
| Glutamine | 0.155 |
| Normetanephrine | 0.234 |
| Ornithine | 0.196 |
| Valine | 0.192 |
| Index | 0.255 |

A quadratic curve was fit to each of the variables and the $R^2$ (proportion of variance explained) was computed (Table 10). For the individual compounds the $R^2$ ranged from 0.155 to 0.234. As expected, the $R^2$ for the Index, which is composed of the compounds listed in Table 8, was larger, $R^2=0.255$.

Thus, the Index reduces variability and provides a larger proportion of variance that can be explained.

Figure 5A:
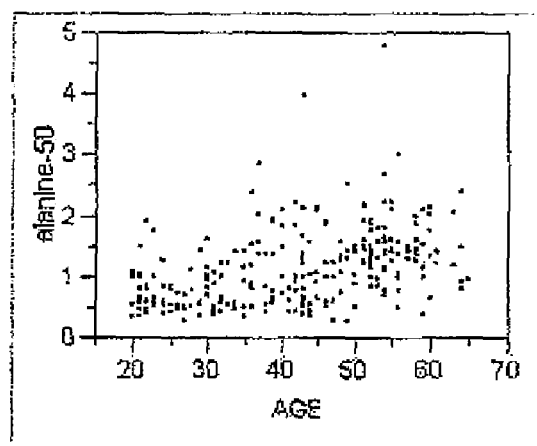
FIGS. 5A-F are scatterplots of the individual compounds and the index comprised of these compounds compared to age.
Figure 5B:
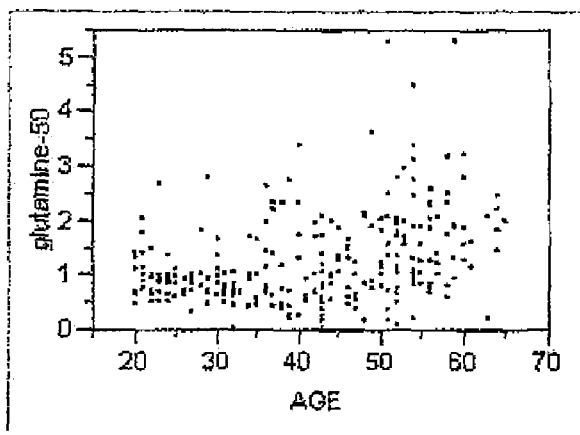
Figure 5C:
Figure 5D:
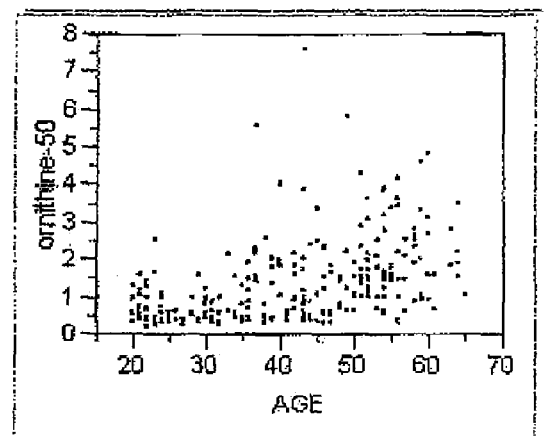
Figure 5E:
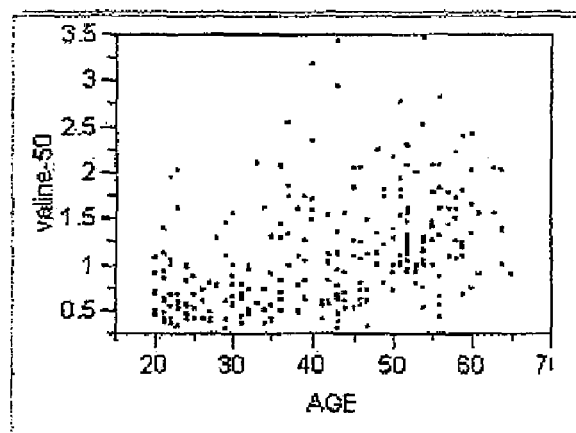
Figure 5F:
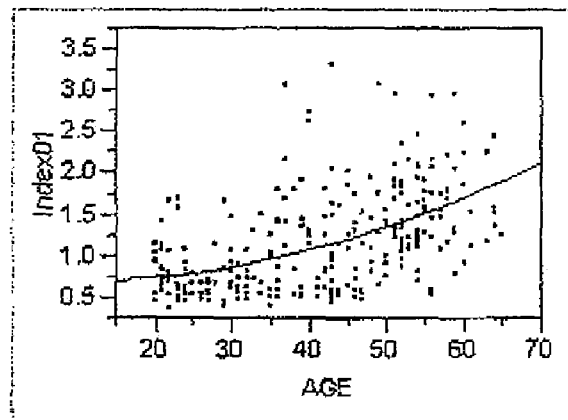

As illustrated in the Scatterplots of each of the compounds compared to age shown in FIGS. 5A-E, the increase in the level of each of the compounds in this example becomes more pronounced at around age 45. Also the variability appears to increase with age. The index derived from alanine, glutamine, normetanephrine, ornithine, and valine has been fit with a Quadratic curve (solid line) and is shown in FIG. 5F A number of sources of variability are responsible for variation in individual metabolites. About 19% of the variability in metabolite levels is due to aging, e.g. loss of biochemical control. The remaining variability may result from various sources. Some variability comes from the biochemical analytical process, although in our platform this is typically <5-8%. Some variability may be due to individual differences in genetics and environment. Some variability comes from life style differences among the people. For example, eating or exercise habits might influence the levels of metabolites or chemicals. People with lower levels of certain metabolites may be considered of younger biochemical age.

Figure 6:
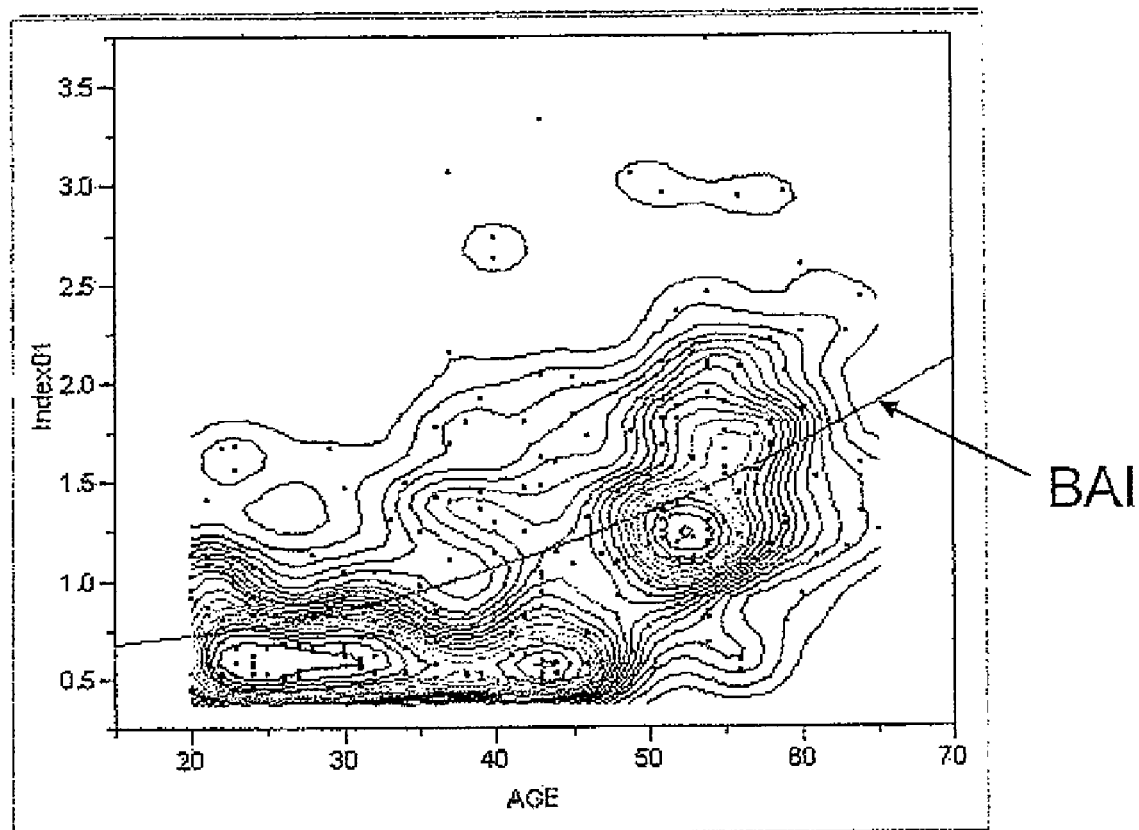
FIG. 6 is a density contour chart of Biochemical Age Index (BAI) versus age. The density of the data points in each region are illustrated by the contour lines. The BAI is indicated by the solid line.

As shown in Table 10, one way to reduce the analytical variation in assessing biochemical age is to average a number of compounds that are increasing (or decreasing, although only increasing compounds were used in this example, further it is possible to compute an index using both increasing and decreasing compounds) with age. The average can be considered a biochemical age index (BAI). FIG. 6 shows a density contour chart with BAI versus chronological age. The density of the data points in each region are illustrated by the contour lines. The BAI results from the quadratic curve fit to the variables and is indicated by the thick solid line.

Compounds can be selected for addition to the index in the following way. We start with named compounds that increase or decrease with age in a statistically significant manner. Compounds that are obviously associated with food, e.g. caffeine from tea or coffee, tartaric acid from wine, are removed from the list. (Although these xenobiotics can be used to determine a xenobiotic index in a similar manner). Unnamed compounds that are correlated with named compounds remaining on the list can be added to the list to help reduce the variability of the index.

Non-parametric density contours are helpful in representing the information in the data (see FIG. 6). The Index appears to be low, <0.75, for individuals, (ages 20-45), and then appears to increase markedly for individuals over 45. Even so, there are a few individuals over 45 that have a low Index. Also, it is clear that there are a large number of individuals under 45 with large values of the Index. These individuals might be considered prematurely old.

Many named and unnamed compounds have been identified that change with age, and by combining these compounds into an index, we get a more stable relationship of compounds associated with age. This information makes it possible to construct a Biochemical Age Index, BAI.

Example 4

Application of Index to Determine the Metabolic Age Score ("MetaboScore")

Figure 7:
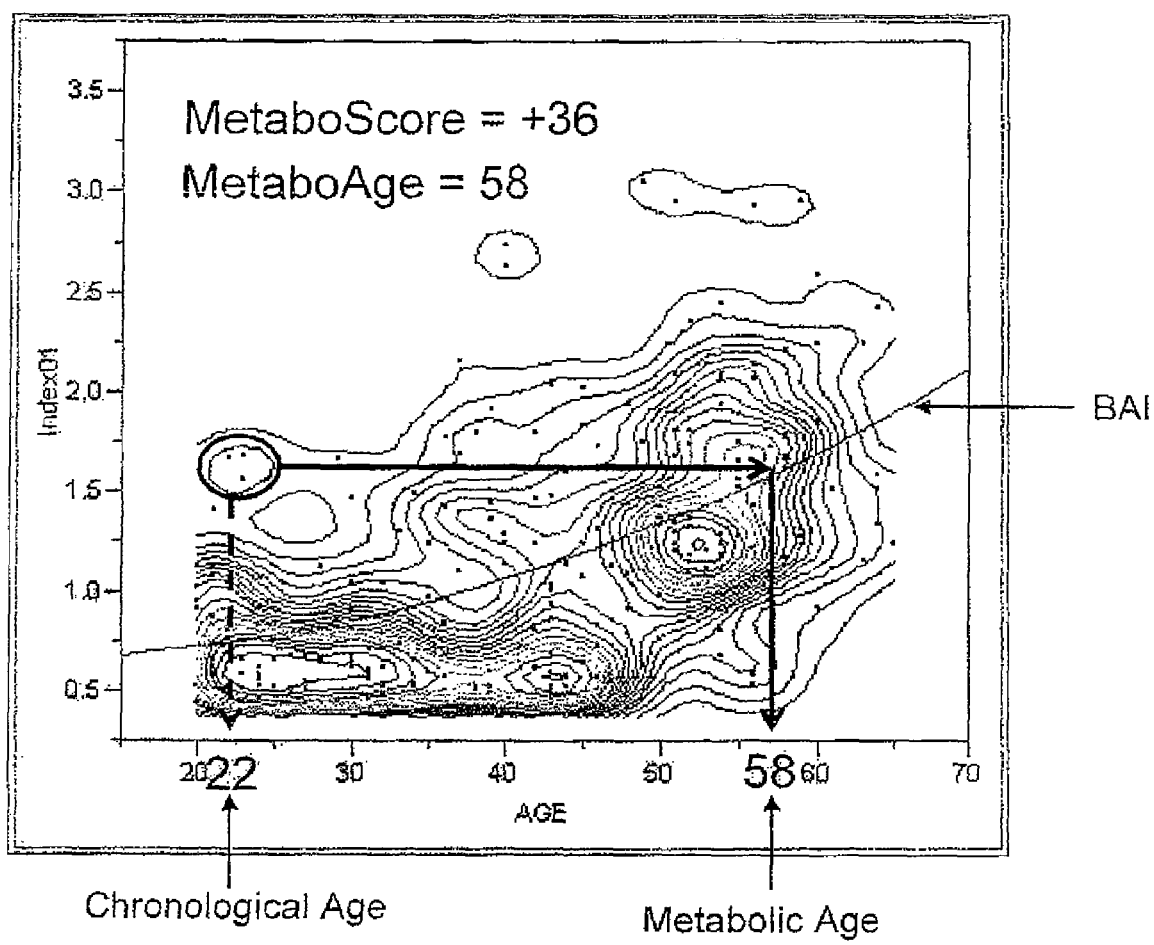
FIG. 7 is a density contour chart of BAI vs. chronological age and shows how determination of a positive MetaboScore is obtained. In the illustration the individual(s) in the black circle have a metabolic age (MetaboAge) of 58 and chronological age of 22 resulting in a MetaboScore of +36, indicating that the individual is biochemically older than the chronological age.

To determine the metabolic age of an individual, a biological sample (e.g. plasma, urine, saliva, etc.) is obtained from an individual (e.g. human, non-human primate, mammal, dog, horse, cat, etc.) and subjected to metabolomic analysis. The resulting metabolic profile is then used to compute the biochemical age index score for the individual (BAI-Score). The metabolic age (MetaboAge) of the individual then can be determined by locating the BAI-Score of the individual on the chart shown in FIG. 7. As shown in FIG. 7, each black dot on the chart indicates an individual BAI-score. A line is drawn from the individual to the BAI (diagonal line) and then a line is drawn to the X-axis to determine the metabolic age (or MetaboAge). A line is also drawn from the individual down to the X-axis to determine the chronological age. The difference between the chronological age and the metabolic age (or MetaboAge) is the "MetaboScore". In the illustration in FIG. 7 the individual(s) in the black circle have a metabolic age (MetaboAge) of 58 and chronological age of 22 resulting in a MetaboScore of +36, indicating that the individual is metabolically older than their chronological age.

Figure 8:
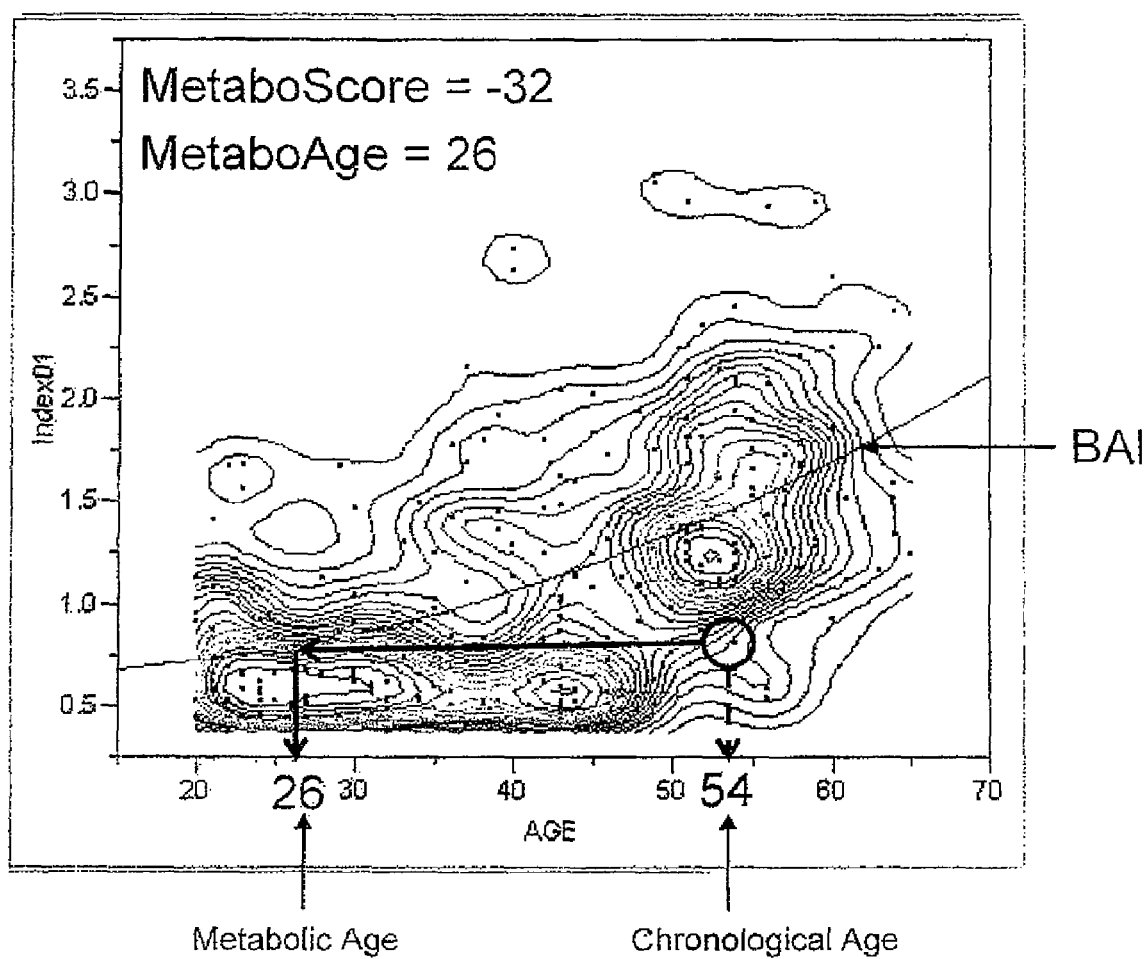
FIG. 8 is a density contour chart of BAI vs. chronological age and showing how determination of a negative MetaboScore is obtained. In this illustration the individual in the dark black circle has a metabolic age (MetaboAge) of 26 and chronological age of 54 resulting in a MetaboScore of −28, indicating that the individual is biochemically younger than the chronological age.

In a similar manner a negative MetaboScore can be determined. As shown in FIG. 8, a line is drawn from the individual to the BAI and then a line is drawn to the X-axis to determine the metabolic age (MetaboAge). A line is also drawn from the individual down to the X-axis to determine the chronological age. The difference between the chronological age and the metabolic age is the "MetaboScore". In this illustration in FIG. 8, the individual in the dark black circle has a metabolic age (MetaboAge) of 26 and chronological age of 54 resulting in a MetaboScore of −28, indicating that the individual is metabolically younger than the chronological age.

Example 5

Refining the Biochemical Age Index

This example describes experiments that analyze additional compounds in a variety of individuals under various conditions to enhance and refine the BAT as it relates to different conditions and age. A more stable relationship between age and metabolic profile will be obtained by combining additional named and unnamed compounds that are shown to change with age into an index such as the BAT. The present invention describes how this information was used to produce an indication of metabolic age and constructed a Biochemical Age Index. This BAI was used in combination with the metabolomic profile of the individual to get an indication of the metabolic age ("MetaboAge") of the individual and from this the individual's MetaboScore was determined.

With additional data, it is possible to construct a more robust Biochemical Age Index (BAI). To this end, experiments are conducted to identify and remove variability from the measured chemicals. Examples of these experiments are described below and listed in Table 11.

Biological samples will be obtained from groups of subjects as described in Table 11 and subjected to metabolomic analysis. For each age classification a factorial (intervention) study is conducted. Each group consists of for example, 100 individuals with 25 subjects in each of four age groups (e.g. young adult (18-30), adult (30-45), middle age (46-65), senior (>65)). A BAI is determined based upon the correlated compounds as described in Example 4.

TABLE 11

Example comparisons for further BAI studies

| Group 1 | Group 2 |
|---|---|
| Fasting individuals (various times of fast) | Non-fasting individuals |
| Vegetarian diet | Non-vegetarian diet |
| Vitamin supplements | Non-supplemented |
| Caffeine | No caffeine |
| Coffee | Tea |
| Alcohol | No alcohol |
| Exercise regime | No Exercise |

These treatments can be carried out independently and/or in combination (e.g. Alcohol and Vegetarian Diet vs. No Alcohol and Vegetarian Diet; Alcohol and Caffeine vs. No Alcohol and No Caffeine). Alternatively, metadata can be collected from individuals (e.g. enrollment questionnaire) in the simple 2-way experiments designed above to further stratify the cohort and thereby to provide additional discriminating power.

Example 6

Determination of Healthful Diets and Xenobiotic Content (e.g. the Xenobiotic Score)

This example describes the measurement of xenobiotic compounds from individuals and determines a correlation between xenobiotic compounds and age. Measurement of such xenobiotic compounds is used to calculate a xenobiotic score to determine dietary differences between individuals and according to age.

Figure 9:
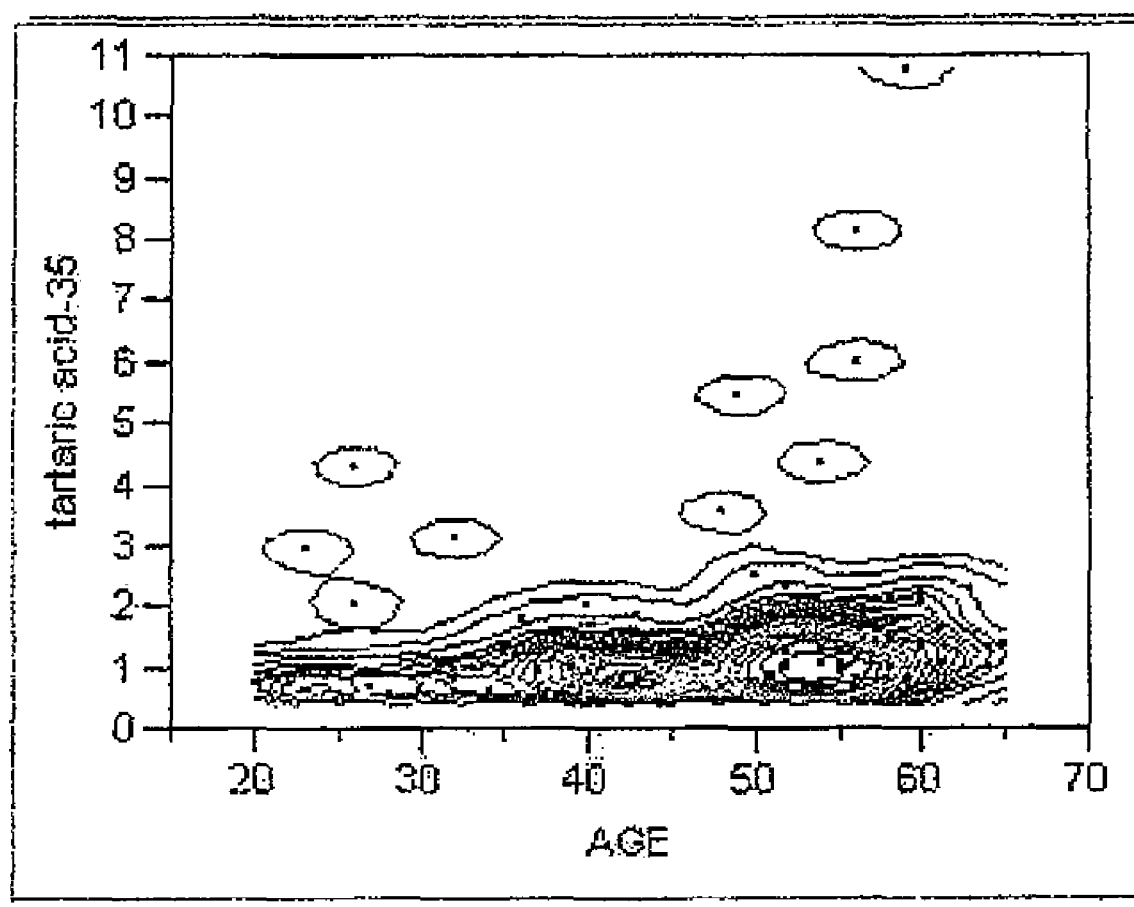
FIG. 9 is a density contour diagram of tartaric acid concentration versus chronological age. While the majority of individuals have values of tartaric acid <2, numerous outlying values (>3) can be seen at both younger and older ages.

Tartaric acid is a white crystalline organic acid. It occurs naturally in many plants, particularly grapes and tamarinds, and is one of the main acids found in wine. It is added to other foods to give a sour taste, and is used as an antioxidant. Salts of tartaric acid are known as tartrates. It is a dihydroxy derivative of dicarboxylic acid. FIG. 9 shows a density diagram of the concentration of tartaric acid versus chronological age. People with high levels of tartaric acid, presumably from wine, are older with an average age of 50. Note the outliers with very elevated levels of tartaric acid are presumably serious wine drinkers.

Benzoic acid (BA) levels were also measured. Benzoic acid is also a common food component. It is used as a preservative in packaged foods such as pickles and lunch meats, and it occurs naturally in cranberries. "Bacterial deamination of the amino acid phenylalanine produces benzoate, which is conjugated with glycine in the liver to form hippurate. This should be taken into account when interpreting elevated hippurate levels in urine. Whether the source is dietary intake or jejunal bacterial metabolism, benzoate is usually converted to hippurate by conjugation with glycine in the liver. Glycine and pantothenic acid are the limiting factors in this process. Therefore, elevated benzoate is a marker of inadequate levels of these nutrients." (See Brailey and Lord, 2001, *Laboratory Evaluations in Molecular Medicine: Nutrients, Toxicants, and Cell Regulators*, Chapter 6 Organic Acids, page 206, Institute for Advances in Molecular Medicine (IAMM) Norcross, Ga., USA)

Figure 10:
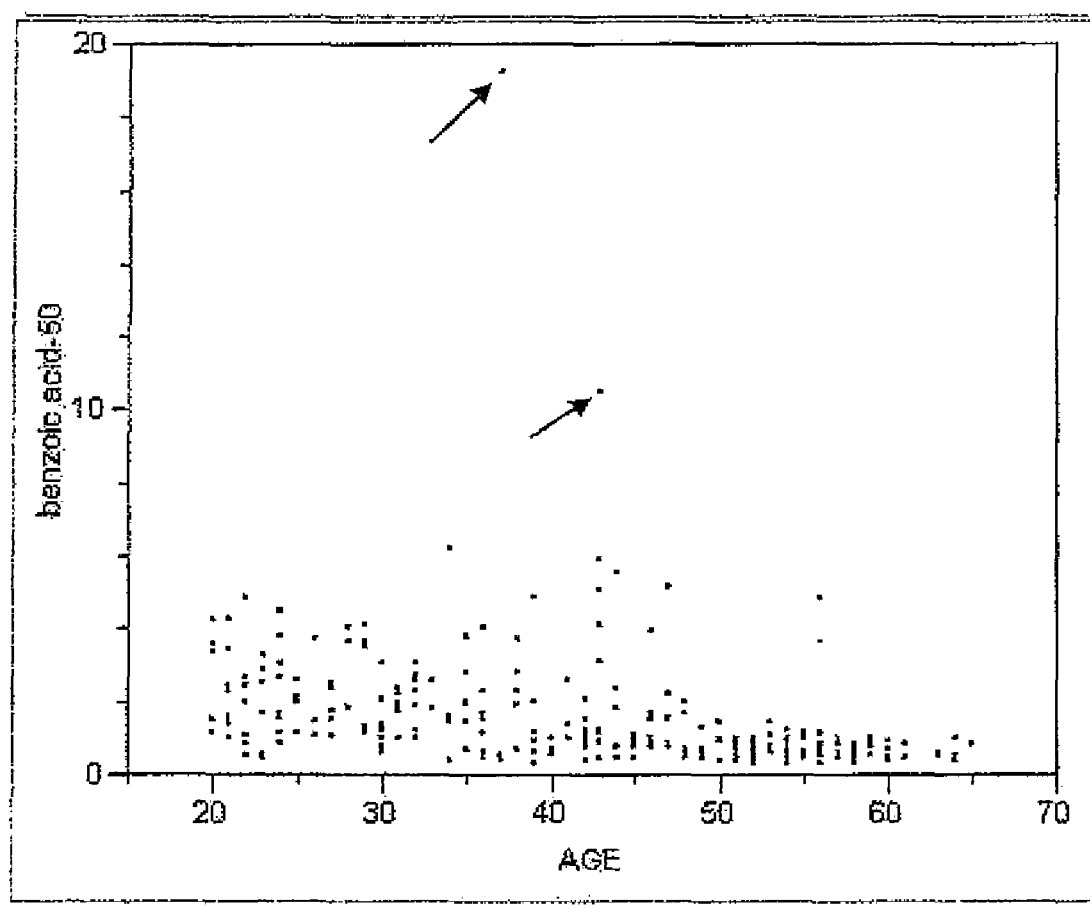
FIG. 10 is a scatterplot diagram of benzoic acid versus chronological age. While the majority of individuals have values of benzoic acid <6, two individuals with benzoic acid values >10 are observed.

FIG. 10 shows a scatterplot of levels of BA versus age. Note the two outlier values (see arrows) for BA; both happen to be females. Since BA is a component of diet soda, and since it is quite common for females to consume diet soft drinks, these results could indicate that the individuals are diet soda drinkers.

Figure 11:
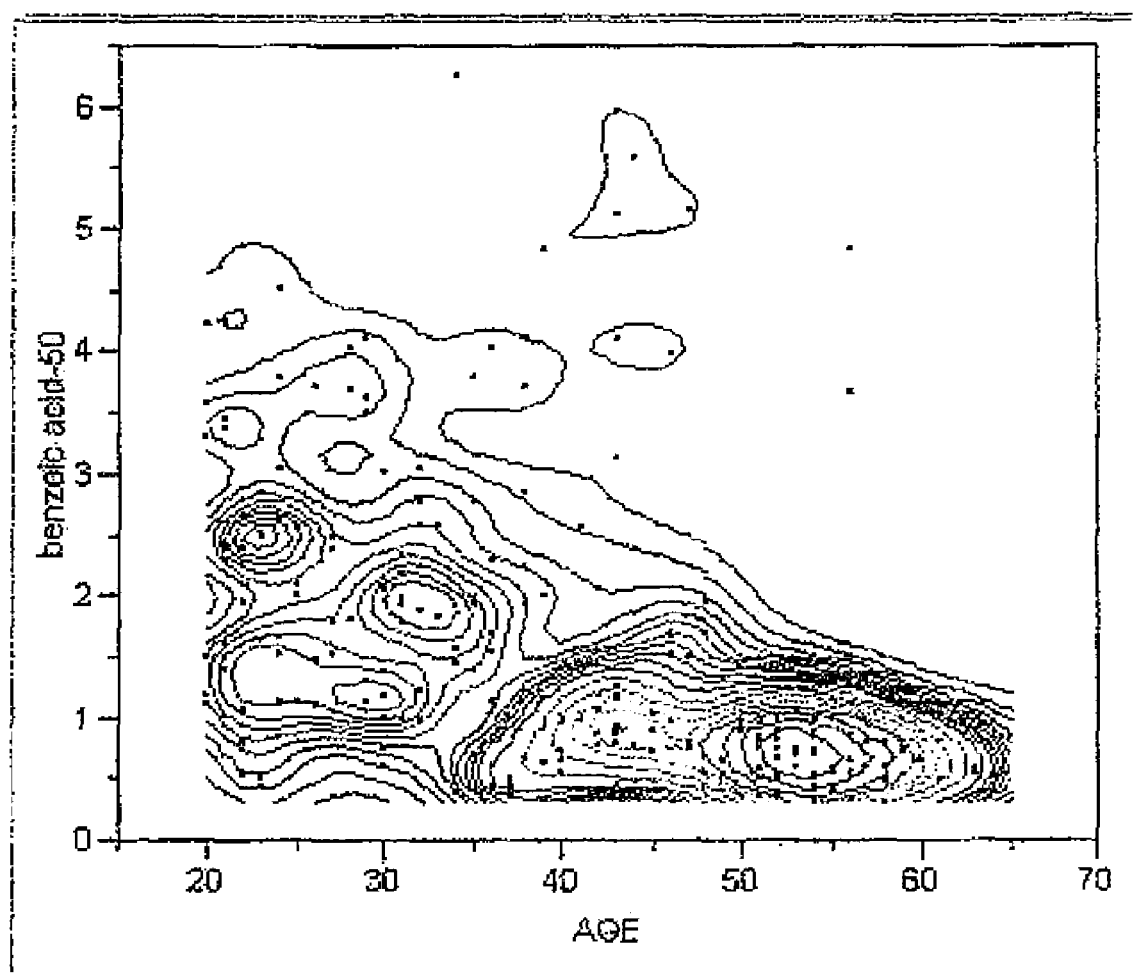
FIG. 11 is a density contour diagram of benzoic acid versus chronological age. A decrease in benzoic acid is illustrated and individuals with low levels (<0.5) of benzoic acid are observed.

FIG. 11 shows a density contour diagram of Benzoic acid compared to age. The levels of BA are somewhat reduced in older individuals, suggesting that older people might metabolize the BA more rapidly than younger people. Alternatively, the difference may be due to differences in the diets. These hypotheses can be verified experimentally; BA could be given to older and younger subjects in order to see if the older subjects get rid of it more efficiently than young people.

Example 7

Individual Metabolite Scores and Ratios

Figure 12:
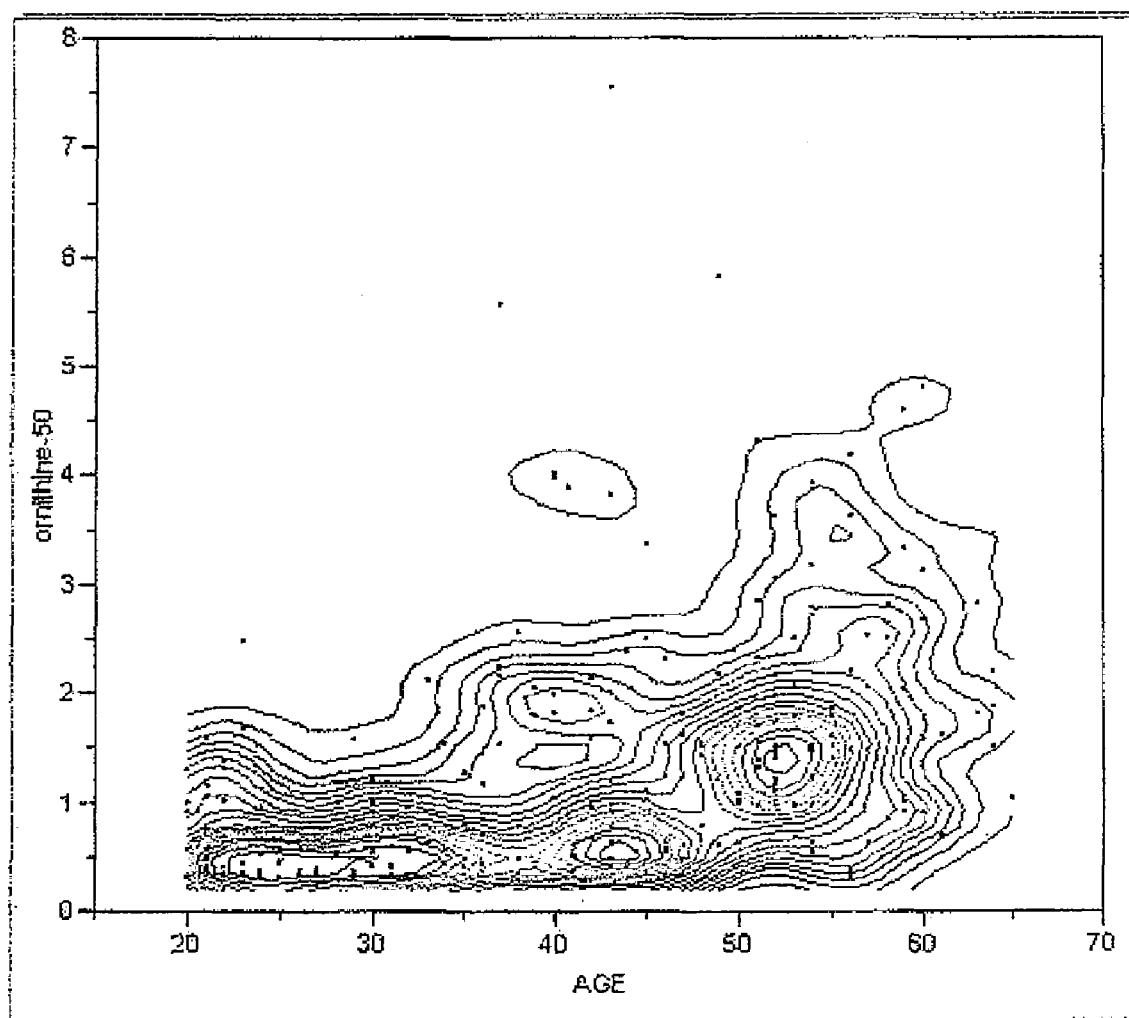
FIG. 12 is a density contour diagram of ornithine concentrations versus chronological age. An increase in ornithine with age is illustrated and individuals with high levels (>5) of ornithine are observed.

This example describes the measurement of certain metabolites and calculation of ratios between the metabolite ornithine versus age. FIG. 12 shows a density contour diagram of ornithine concentration versus age. The figure shows a shift in ornithine concentration in blood which increases after age 50 and is rather dramatic. The results suggest that there is an age effect that could be modified by diet. Alternatively, this could be an indication of lifestyle, disease, or disease susceptibility. This idea is supported by the observed wide distribution of ornithine from age 35 to 41. The very skewed distribution of ornithine at just about any age could indicate unhealthy effects due to unidentified causes. It has been shown that induced hepatic failure in pigs results in elevation of both ornithine and citrulline.

While the invention has been described in detail and with reference to specific embodiments thereof, it will be apparent to one skilled in the art that various changes and modifications can be made without departing from the spirit and scope of the invention.

What is claimed is:

1. A method for determining the metabolic age of a subject comprising the steps of:
   a) analyzing a biological sample from a subject to determine the level(s) of glycine and one or more biomarkers for metabolic age in the sample, wherein the one or more biomarkers are selected from the group consisting of alanine, glutamine, normetanephrine, ornithine and valine and
   b) comparing the level(s) of glycine and the one or more biomarkers in the sample to metabolic age reference levels of glycine and the one or more biomarkers to determine the subject's metabolic age.

2. The method of claim 1, wherein the level(s) of the one or more biomarkers in the sample are compared to a biochemical age index to determine the subject's metabolic age.

3. The method of claim 1, wherein levels of glycine and the one or more biomarkers in the sample are similar to metabolic age reference levels corresponding to an older chronological age are indicative of a negative metabolic age.

4. The method of claim 1, wherein levels of glycine and the one or more biomarkers in the sample are similar to metabolic age reference levels corresponding to a younger chronological age are indicative of a positive metabolic age.

5. The method of claim 1, wherein the biological sample is blood plasma.

6. The method of claim 1, wherein the reference level(s) are tailored to a population selected from the group consisting of gender, race and combinations thereof.

7. The method of claim 1, wherein said subject is a male subject.

8. The method of claim 1, wherein said subject is a female subject.

* * * * *

UNITED STATES PATENT AND TRADEMARK OFFICE
CERTIFICATE OF CORRECTION

PATENT NO. : 7,781,160 B2  Page 1 of 1
APPLICATION NO. : 11/871752
DATED : August 24, 2010
INVENTOR(S) : John Ryals et al.

It is certified that error appears in the above-identified patent and that said Letters Patent is hereby corrected as shown below:

Column 56, line 37, after "level(s) of" please insert --glycine and--.

Signed and Sealed this

Twenty-third Day of November, 2010

David J. Kappos
*Director of the United States Patent and Trademark Office*